United States Patent
Van Lommen et al.

(10) Patent No.: US 7,511,068 B2
(45) Date of Patent: Mar. 31, 2009

(54) MERCAPTOIMIDAZOLES AS CCR2 RECEPTOR ANTAGONISTS

(75) Inventors: Guy Rosalia Eugeen Van Lommen, Berlaar (BE); Julien Georges Pierre-Olivier Doyon, Turnhout (BE); Jean Pierre Frans Van Wauwe, Beerse (BE); Marina Lucie Louise Cools, Retie (BE); Erwin Coesemans, Nijlen (BE)

(73) Assignee: Janssen Pharmaceutica, N.V., Beerse (BE)

( * ) Notice: Subject to any disclaimer, the term of this patent is extended or adjusted under 35 U.S.C. 154(b) by 240 days.

(21) Appl. No.: 10/544,569

(22) PCT Filed: Jan. 30, 2004

(86) PCT No.: PCT/EP2004/000957

§ 371 (c)(1),
(2), (4) Date: Aug. 3, 2005

(87) PCT Pub. No.: WO2004/069810

PCT Pub. Date: Aug. 19, 2004

(65) Prior Publication Data

US 2006/0058289 A1    Mar. 16, 2006

(30) Foreign Application Priority Data

Feb. 3, 2003 (EP) .................................. 0301038

(51) Int. Cl.
*A61K 31/4164* (2006.01)
*C07D 233/04* (2006.01)

(52) U.S. Cl. ................. 514/392; 548/300.1; 548/316.4; 548/323.5; 548/324.1; 514/385; 514/386

(58) Field of Classification Search ............. 548/300.1, 548/318.4, 323.5, 324.1; 514/385, 386, 392
See application file for complete search history.

(56) References Cited

U.S. PATENT DOCUMENTS

| | | | | | |
|---|---|---|---|---|---|
| 4,835,154 | A | * | 5/1989 | Finkelstein et al. | 514/254.05 |
| 5,155,118 | A | * | 10/1992 | Carini et al. | 514/381 |
| 5,312,828 | A | * | 5/1994 | Finkelstein et al. | 514/381 |
| 5,354,867 | A | * | 10/1994 | Carini et al. | 548/252 |
| 6,028,091 | A | * | 2/2000 | Hill | 514/381 |
| 6,034,114 | A | * | 3/2000 | Hill | 514/381 |

FOREIGN PATENT DOCUMENTS

| | | |
|---|---|---|
| EP | 0294973 A | 12/1988 |
| WO | WO 99/40913 | 8/1999 |
| WO | WO 0012489 A | 3/2000 |
| WO | WO 01/05430 A1 | 1/2001 |
| WO | WO 01/51466 A1 | 7/2001 |

OTHER PUBLICATIONS

Loksha, et al., J. Heterocyclic Chem., vol. 39, 375-382 (2002).*
Yokomori et al (1991): STN International CAPLUS database, (Columbus, Ohio), Accession No. 1991:15274.*
Yokomori, Yoshinobu, Crystal Structure of 1-(4-Nitrobenzyl)-4-thiocarbamoyi-5-cyano-2-imidazolethione Monohydrate, Analytical Sciences, Oct. 1990, vol. 6, pp. 791-792.

* cited by examiner

*Primary Examiner*—Golam M Shameem

(57) ABSTRACT

The present invention relates to a compound of formula (I) having CCR2 receptor antagonistic properties, particularly anti-inflammatory properties.

12 Claims, No Drawings

MERCAPTOIMIDAZOLES AS CCR2 RECEPTOR ANTAGONISTS

This application is a national filing of WO2004/069810 A1 filed on Jan. 30, 2004, which claims priority of PCT/EP03/01038 filed on Feb. 3, 2003.

The present invention concerns mercaptoimidazole derivatives having CCR2 receptor antagonistic properties. The invention further relates to methods for their preparation and pharmaceutical compositions comprising them. The invention also relates to the use of said compounds for the manufacture of a medicament for the prevention or the treatment of diseases mediated through activation of the CCR2 receptor, in particular the CCR2B receptor.

EP 0,240,050 discloses 1-methyl-1H-imidazole-5-carboxylic acid derivatives for controlling weeds.

U.S. Pat. No. 3,354,173 discloses imidazole carboxylates as hypnotics.

U.S. Pat. No. 4,182,624 discloses benzhydryl-imidazole derivatives having carboxyl functions in the imidazole ring. The compounds are described as having valuable properties in plant protection and growth regulation in agriculture and horticulture.

EP 0,000,373 relates to imidazole carbonic acid derivatives and their use for plant protection.

WO 01/17974 and Organic Process Research and Development, 2002, 6(5), 674-676 relates to the synthesis of 1 substituted 5-(hydroxymethyl)imidazole derivatives.

WO 00/75135 describes biaryl inhibitors of prenyl-protein transferase.

Arzneimittel-Forschung, 1980, 30(7), 1051-1056 describes imidazole derivatives with potential biological activity.

U.S. Pat. No. 4,762,850 relates to 2-mercapto-1-(phenylalkyl)-1H-imidazole-5-carboxylic acid derivatives as dopamine β-hydroxylase inhibitors.

EP 294,973 relates to 1-aralkyl-5-(piperazinomethyl)-imidazole-2-thiols as dopamine, β-hydroxylase inhibitors.

DE 2,618,370 relates to imidazo[5,1-c](1,4)-benzoxazepines and their preparation.

EP 146,228 describes substituted 2-mercapto-imidazoles useful in the preparation of phenylethylimidazole derivatives of therapeutic interest.

WO 01/09127, WO 01/09124 and WO 99/41248 relates to condensed heterocyclic system derivatives as farnesyl transferase inhibitors.

WO 00/01674 relates to the preparation of 1-benzylimidazoles from benzylamines, hydroxyketones and thiocyanates.

WO 92/10182, WO 92/10186, WO 92/10188 and EP 437, 103 concern imidazole derivatives as intermediates in the preparation of angiotensin II receptor antagonists. J. Heterocyclic Chemistry, 1982, 19(3), 561-566 concerns the synthesis of imidazole derivatives with potential biological activity.

WO 02/066458 concerns 2-thio-substituted imidazole derivatives useful to treat diseases which are related to the dysfunction of the immune system.

FR 1487326 and FR 6751 discloses imidazole derivatives as sedatives and analgesics.

WO 01/05430 describes the preparation of 1-(3-chlorophenyl)-4-[1-(4-cyanobenzyl)-5-imidazolyl methyl]-2-piperazinone as model drug for sustained release in a drug delivery device.

WO 99/40913 provides substituted pyrroles which are inhibitors of monocyte chemoattractant protein-1 and WO 01/51466 relates to indole derivatives as MCP-1 receptor antagonists.

The compounds of the invention differ from the prior art compounds in structure, in that they exert a pharmaceutical activity, in their pharmacological activity and/or pharmacological potency.

One aspect of the present invention relates to a compound of formula

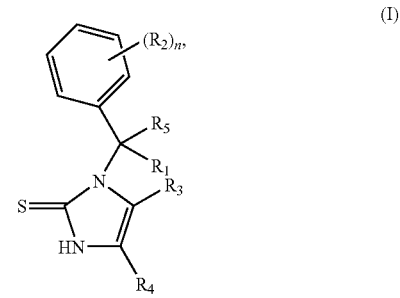

(I)

a N-oxide, a pharmaceutically acceptable addition salt, a quaternary amine and a stereochemically isomeric form thereof, wherein $R_1$ represents hydrogen, $C_{1-6}$alkyl, $C_{3-7}$cycloalkyl, $C_{1-6}$alkyloxy$C_{1-6}$alkyl, di($C_{1-6}$alkyl)amino$C_{1-6}$alkyl, aryl or heteroaryl;

each $R_2$ independently represents halo, $C_{1-6}$alkyl, $C_{1-6}$alkyloxy, $C_{1-6}$alkylthio, polyhalo$C_{1-6}$alkyl, polyhalo$C_{1-6}$alkyloxy, cyano, aminocarbonyl, amino, mono- or di($C_{1-4}$alkyl) amino, nitro, aryl or aryloxy;

$R_3$ represents hydrogen, cyano, $C_{1-6}$alkyl optionally substituted with hydroxy or $C_{1-6}$alkyloxy, $C(=O)-O-R_6$, $C(=O)-NR_{7a}R_{7b}$, $C(=S)-NR_{7a}R_{7b}$, $S(=O)_2-NR_{7a}R_{7b}$ or $C(=O)-R_8$;

$R_4$ represents hydrogen, cyano, $C_{1-6}$alkyl optionally substituted with hydroxy or $C_{1-6}$alkyloxy, $C(=O)-O-R_6$, $C(=O)-NR_{7a}R_{7b}$, $C(=S)-NR_{7a}R_{7b}$, $S(=O)_2-NR_{7a}R_{7b}$ or $C(=O)-R_8$;

or $R_3$ and $R_4$ taken together may form a bivalent radical of formula $-C(=O)-NH-NH-C(=O)-$;

$R_6$ represents hydrogen, $C_{1-6}$alkyl, hydroxy$C_{1-6}$alkyl, $C_{2-6}$alkenyl, $C_{2-6}$alkynyl, polyhalo$C_{1-6}$alkyl, $C_{1-6}$alkyloxy$C_{1-6}$alkyl, amino$C_{1-6}$alkyl, mono- or di($C_{1-4}$alkyl) amino$C_{1-6}$alkyl, aminocarbonyl$C_{1-6}$alkyl, mono- or di($C_{1-4}$ alkyl)aminocarbonyl$C_{1-6}$alkyl, aryl, pyrrolidinyl, imidazolidinyl, pyrazolidinyl, piperidinyl, piperazinyl, morpholinyl or thiomorpholinyl; wherein pyrrolidinyl, imidazolidinyl, pyrazolidinyl, piperidinyl, piperazinyl, morpholinyl or thiomorpholinyl may optionally be substituted with $C_{1-4}$alkyl;

$R_{7a}$ and $R_{7b}$ each independently represent hydrogen, $C_{1-4}$alkyl, amino, mono- or di($C_{1-4}$alkyl)amino, arylNH—, amino$C_{1-6}$alkyl, mono- or di($C_{1-4}$alkyl)amino $C_{1-6}$alkyl, $C_{1-6}$alkylcarbonylamino, aminocarbonylamino, $C_{1-6}$alkyloxy, —NH—C(O)—H or hydroxy$C_{1-6}$alkyl; or $R_{7a}$ and $R_{7b}$ taken together with the nitrogen to which they are attached form pyrrolidinyl, imidazolidinyl, pyrazolidinyl, piperidinyl, piperazinyl, morpholinyl, thiomorpholinyl or piperazinyl substituted with $C_{1-4}$alkyl;

$R_8$ represents hydrogen, $C_{1-6}$alkyl, hydroxy$C_{1-6}$alkyl, $C_{2-6}$alkenyl, $C_{2-6}$alkynyl, polyhalo$C_{1-6}$alkyl, $C_{1-6}$alkyloxy$C_{1-6}$alkyl, amino$C_{1-4}$alkyl, mono- or di($C_{1-4}$alkyl) amino$C_{1-6}$alkyl, aminocarbonyl$C_{1-6}$alkyl, mono- or di($C_{1-4}$ alkyl)aminocarbonyl$C_{1-6}$alkyl or aryl;

$R_5$ represents hydrogen or $C_{1-6}$alkyl;

n is 1, 2, 3, 4 or 5;

aryl represents phenyl or phenyl substituted with one, two, three, four or five substituents each independently selected from halo, $C_{1-6}$alkyl, $C_{1-4}$alkyloxy, polyhalo$C_{1-6}$alkyl, polyhalo$C_{1-6}$alkyloxy, cyano, aminocarbonyl, mono- or di($C_{1-4}$alkyl)aminocarbonyl, amino, mono- or di($C_{1-4}$alkyl)amino, phenyloxy or nitro;

heteroaryl represents furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, each of said heterocycles optionally being substituted with one or two substituents each independently selected from halo, $C_{1-6}$alkyl, $C_{1-6}$alkyloxy, polyhalo$C_{1-6}$alkyl, polyhalo$C_{1-6}$alkyloxy, cyano, aminocarbonyl, mono- or di($C_{1-4}$alkyl)aminocarbonyl, amino, mono- or di($C_{1-4}$alkyl)amino or nitro;

provided that at least one of $R_3$ or $R_4$ is other than hydrogen; and that if $R_3$ represents C(=O)—OH, C(=O)—O—$C_{1-6}$alkyl or C(=O)—O—$C_{2-4}$alkenyl, then $R_4$ is other than hydrogen; and that if $R_3$ represents $CH_2OH$ and $R_1$ and $R_5$ represent hydrogen, then $R_4$ is other than hydrogen; and that if $R_3$ represents C(=O)—NH—$C_{1-4}$alkyl-$NH_2$ and $R_1$ and $R_5$ represents hydrogen, then $R_4$ is other than hydrogen; and that if $R_3$ represents

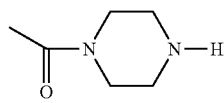

and $R_1$ and $R_5$ represents hydrogen, then $R_4$ is other than hydrogen.

The present invention also relates to a compound of formula (I) as defined above for use as a medicine provided that at least one of $R_3$ or $R_4$ is other than hydrogen; and that if $R_3$ represents C(=O)—OH or C(=O)—O—$C_{1-6}$alkyl; $R_1$ represents aryl and n is 1, then $R_4$ is other than hydrogen; and that if $R_3$ represents C(=O)—NH—$C_{1-4}$alkyl-$NH_2$ or C(=O)—OH and $R_1$ and $R_5$ represent hydrogen, then $R_4$ is other than hydrogen.

Thus, the present invention also relates to a compound for use as a medicine wherein the compound is a compound of formula

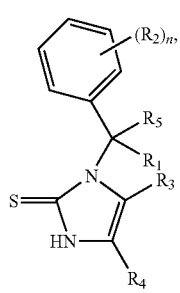

(I)

a N-oxide, a pharmaceutically acceptable addition salt, a quaternary amine and a stereochemically isomeric form thereof, wherein $R_1$ represents hydrogen, $C_{1-6}$alkyl, $C_{3-7}$cycloalkyl, $C_{1-6}$alkyloxy$C_{1-6}$alkyl, di($C_{1-6}$alkyl)amino$C_{1-6}$alkyl, aryl or heteroaryl;

each $R_2$ independently represents halo, $C_{1-6}$alkyl, $C_{1-6}$alkyloxy, $C_{1-6}$alkylthio, polyhalo$C_{1-6}$alkyl, polyhalo$C_{1-6}$alkyloxy, cyano, aminocarbonyl, amino, mono- or di($C_{1-4}$alkyl) amino, nitro, aryl or aryloxy;

$R_3$ represents hydrogen, cyano, $C_{1-6}$alkyl optionally substituted with hydroxy or $C_{1-6}$alkyloxy, C(=O)—O—$R_6$, C(=O)—$NR_{7a}R_{7b}$, C(=S)—$NR_{7a}R_{7b}$, S(=O)$_2$—$NR_{7a}R_{7b}$ or C(=O)—$R_8$;

$R_4$ represents hydrogen, cyano, $C_{1-6}$alkyl optionally substituted with hydroxy or $C_{1-6}$alkyloxy, C(=O)—O—$R_6$, C(=O)—$NR_{7a}R_{7b}$, C(=S)—$NR_{7a}R_{7b}$, S(=O)$_2$—$NR_{7a}R_{7b}$ or C(=O)—$R_8$;

or $R_3$ and $R_4$ taken together may form a bivalent radical of formula —C(=O)—NH—NH—C(=O)—;

$R_6$ represents hydrogen, $C_{1-6}$alkyl, hydroxy$C_{1-6}$alkyl, $C_{2-6}$alkenyl, $C_{2-6}$alkynyl, polyhalo$C_{1-6}$alkyl, $C_{1-6}$alkyloxy$C_{1-6}$alkyl, amino$C_{1-6}$alkyl, mono- or di($C_{1-4}$alkyl)amino$C_{1-6}$alkyl, aminocarbonyl$C_{1-6}$alkyl, mono- or di($C_{1-4}$alkyl)aminocarbonyl$C_{1-6}$alkyl, aryl, pyrrolidinyl, imidazolidinyl, pyrazolidinyl, piperidinyl, piperazinyl, morpholinyl or thiomorpholinyl; wherein pyrrolidinyl, imidazolidinyl, pyrazolidinyl, piperidinyl, piperazinyl, morpholinyl or thiomorpholinyl may optionally be substituted with $C_{1-4}$alkyl;

$R_{7a}$ and $R_{7b}$ each independently represent hydrogen, $C_{1-6}$alkyl, amino, mono- or di($C_{1-4}$alkyl)amino, arylNH—, amino$C_{1-6}$alkyl, mono- or di($C_{1-4}$alkyl)amino $C_{1-6}$alkyl, $C_{1-6}$alkylcarbonylamino, aminocarbonylamino, $C_{1-6}$alkyloxy, —NH—C(O)—H or hydroxy$C_{1-6}$alkyl; or $R_{7a}$ and $R_{7b}$ taken together with the nitrogen to which they are attached form pyrrolidinyl, imidazolidinyl, pyrazolidinyl, piperidinyl, piperazinyl, morpholinyl, thiomorpholinyl or piperazinyl substituted with $C_{1-6}$alkyl;

$R_8$ represents hydrogen, $C_{1-6}$alkyl, hydroxy$C_{1-6}$alkyl, $C_{2-6}$alkenyl, $C_{2-6}$alkynyl, polyhalo$C_{1-6}$alkyl, $C_{1-6}$alkyloxy$C_{1-6}$alkyl, amino$C_{1-6}$alkyl, mono- or di($C_{1-4}$alkyl)amino$C_{1-6}$alkyl, aminocarbonyl$C_{1-6}$alkyl, mono- or di($C_{1-4}$alkyl)aminocarbonyl$C_{1-6}$alkyl or aryl;

$R_5$ represents hydrogen or $C_{1-6}$alkyl;

n is 1, 2, 3, 4 or 5;

aryl represents phenyl or phenyl substituted with one, two, three, four or five substituents each independently selected from halo, $C_{1-6}$alkyl, $C_{1-6}$alkyloxy, polyhalo$C_{1-6}$alkyl, polyhalo$C_{1-6}$alkyloxy, cyano, aminocarbonyl, mono- or di($C_{1-4}$alkyl)aminocarbonyl, amino, mono- or di($C_{1-4}$alkyl)amino, phenyloxy or nitro;

heteroaryl represents furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, each of said heterocycles optionally being substituted with one or two substituents each independently-selected from halo, $C_{1-6}$alkyl, $C_{1-6}$alkyloxy, polyhalo$C_{1-6}$alkyl, polyhalo$C_{1-6}$alkyloxy, cyano, aminocarbonyl, mono- or di-($C_{1-4}$alkyl)aminocarbonyl, amino, mono- or di($C_{1-4}$alkyl)amino or nitro;

provided that at least one of $R_3$ or $R_4$ is other than hydrogen; and that if $R_3$ represents C(=O)—OH or C(=O)—O—$C_{1-6}$alkyl; $R_1$ represents aryl and n is 1, then $R_4$ is other than hydrogen; and that if $R_3$ represents C(=O)—NH—$C_{1-4}$alkyl-$NH_2$ or C(=O)—OH and $R_1$ and $R_5$ represent hydrogen, then $R_4$ is other than hydrogen.

Another aspect of the present invention is the use of the compounds of formula (I) as defined above for the manufacture of a medicament for preventing or treating diseases mediated through activation of the CCR2 receptor, in particular for preventing or treating inflammatory diseases.

Thus, the present invention also relates to the use of a compound for the manufacture of a medicament for preventing or treating diseases mediated through activation of the CCR2 receptor, in particular for preventing or treating inflammatory diseases, wherein said compound is a compound of formula (I)

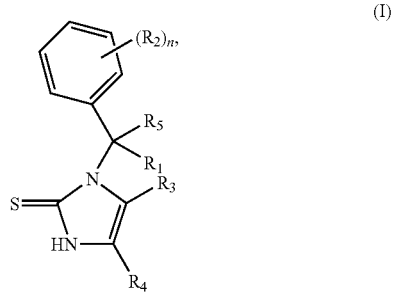

a N-oxide, a pharmaceutically acceptable addition salt, a quaternary amine and a stereochemically isomeric form thereof, wherein $R_1$ represents hydrogen, $C_{1-6}$alkyl, $C_{3-7}$cycloalkyl, $C_{1-6}$alkyloxy$C_{1-6}$alkyl, di($C_{1-4}$alkyl)amino$C_{1-6}$alkyl, aryl or heteroaryl;

each $R_2$ independently represents halo, $C_{1-6}$alkyl, $C_{1-6}$alkyloxy, $C_{1-6}$alkylthio, polyhalo$C_{1-6}$alkyl, polyhalo$C_{1-6}$alkyloxy, cyano, aminocarbonyl, amino, mono- or di($C_{1-4}$alkyl)amino, nitro, aryl or aryloxy;

$R_3$ represents hydrogen, cyano, $C_{1-6}$alkyl optionally substituted with hydroxy or $C_{1-6}$alkyloxy, C(=O)—O—$R_6$, C(=O)—N$R_{7a}R_{7b}$, C(=S)—N$R_{7a}R_{7b}$, S(=O)$_2$—N$R_{7a}R_{7b}$ or C(=O)—$R_8$;

$R_4$ represents hydrogen, cyano, $C_{1-6}$alkyl optionally substituted with hydroxy or $C_{1-6}$alkyloxy, C(=O)—O—$R_6$, C(=O)—N$R_{7a}R_{7b}$, C(=S)—N$R_7$,$R_{7b}$, S(=O)$_2$—N$R_{7a}R_{7b}$ or C(=O)—$R_8$;

or $R_3$ and $R_4$ taken together may form a bivalent radical of formula —C(=O)—NH—NH—C(=O)—;

$R_6$ represents hydrogen, $C_{1-6}$alkyl, hydroxy$C_{1-6}$alkyl, $C_{2-6}$alkenyl, $C_{2-6}$alkynyl, polyhalo$C_{1-6}$alkyl, $C_{1-6}$alkyloxy$C_{1-6}$alkyl, amino$C_{1-6}$alkyl, mono- or di($C_{1-4}$alkyl)amino$C_{1-6}$alkyl, aminocarbonyl$C_{1-6}$alkyl, mono- or di($C_{1-4}$ alkyl)aminocarbonyl$C_{1-6}$alkyl, aryl, pyrrolidinyl, imidazolidinyl, pyrazolidinyl, piperidinyl, piperazinyl, morpholinyl or thiomorpholinyl; wherein pyrrolidinyl, imidazolidinyl, pyrazolidinyl, piperidinyl, piperazinyl, morpholinyl or thiomorpholinyl may optionally be substituted with $C_{1-4}$alkyl;

$R_{7a}$ and $R_{7b}$ each independently represent hydrogen, $C_{1-6}$alkyl, amino, mono- or di($C_{1-4}$alkyl)amino, arylNH—, amino$C_{1-6}$alkyl, mono- or di($C_{1-4}$alkyl)amino $C_{1-6}$alkyl, $C_{1-6}$alkylcarbonylamino, aminocarbonylamino, $C_{1-6}$alkyloxy, —NH—C(O)—H or hydroxy$C_{1-6}$alkyl; or $R_{7a}$ and $R_{7b}$ taken together with the nitrogen to which they are attached form pyrrolidinyl, imidazolidinyl, pyrazolidinyl, piperidinyl, piperazinyl, morpholinyl, thiomorpholinyl or piperazinyl substituted with $C_{1-6}$alkyl;

$R_8$ represents hydrogen, $C_{1-6}$alkyl, hydroxy$C_{1-6}$alkyl, $C_{2-6}$alkenyl, $C_{2-6}$alkynyl, polyhalo$C_{1-6}$alkyl, $C_{1-6}$alkyloxy$C_{1-6}$alkyl, amino$C_{1-6}$alkyl, mono- or di($C_{1-4}$alkyl) amino$C_{1-6}$alkyl, aminocarbonyl$C_{1-6}$alkyl, mono- or di($C_{1-4}$ alkyl)aminocarbonyl$C_{1-6}$alkyl or aryl;

$R_5$ represents hydrogen or $C_{1-6}$alkyl;

n is 1, 2, 3, 4 or 5;

aryl represents phenyl or phenyl substituted with one, two, three, four or five substituents each independently selected from halo, $C_{1-6}$alkyl, $C_{1-6}$alkyloxy, polyhalo$C_{1-6}$alkyl, polyhalo$C_{1-6}$alkyloxy, cyano, aminocarbonyl, mono- or di($C_{1-4}$alkyl)aminocarbonyl, amino, mono- or di($C_{1-4}$ alkyl)amino, phenyloxy or nitro;

heteroaryl represents furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, each of said heterocycles optionally being substituted with one or two substituents each independently selected from halo, $C_{1-6}$alkyl, $C_{1-6}$alkyloxy, polyhalo$C_{1-6}$alkyl, polyhalo$C_{1-6}$alkyloxy, cyano, aminocarbonyl, mono- or di($C_{1-4}$alkyl)aminocarbonyl, amino, mono- or di($C_{1-4}$alkyl)amino or nitro;

provided that at least one of $R_3$ or $R_4$ is other than hydrogen.

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing or hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-6}$alkyl as a group or part of a group is defined as mono- or polyhalosubstituted $C_{1-6}$alkyl, for example, the groups defined in polyhalomethyl, 1,1-difluoro-ethyl and the like. In case more than one halogen atoms are attached to an alkyl group within the definition of polyhalomethyl or polyhalo$C_{1-6}$ alkyl, they may be the same or different.

The term heteroaryl in the definition of $R_1$ is meant to include all the possible isomeric forms of the heterocycles, for instance, pyrrolyl comprises 1H-pyrrolyl and 2H-pyrrolyl.

The aryl, heteroaryl or heterocyclic ring systems listed in the definitions of the substituents of the compounds of formula (I) (see for instance $R_1$ and $R_6$) as mentioned hereinabove or hereinafter may be attached to the remainder of the molecule of formula (I) through any ring carbon or heteroatom as appropriate, if not otherwise specified. Thus, for example, when heteroaryl is imidazolyl, it may be 1-imidazolyl, 2-imidazolyl, 4-imidazolyl and the like.

When any variable (eg. $R_{7a}$, $R_{7b}$) occurs more than one time in any constituent, each definition is independent.

Lines drawn from substituents into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen.

Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts; solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

For some of the compounds of formula (I), their N-oxides, salts, solvates, quaternary amines and the intermediates used in the preparation thereof, the absolute stereochemical configuration was not experimentally determined. In these cases the stereoisomeric form which was first isolated is designated as "A" and the second as "B", without further reference to the actual stereochemical configuration. However, said "A" and "B" stereoisomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the second as "A2" and "B2", without further reference to the actual stereochemical configuration.

Some of the compounds of formula (I) may also exist in their tautomeric form. Such forms although not explicitly indicated in the above formula (I) are intended to be included within the scope of the present invention. For instance, it is intended that formula (I) includes the tautomeric form of

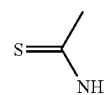

being

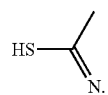

Thus, the compounds of the present invention include compounds of formula

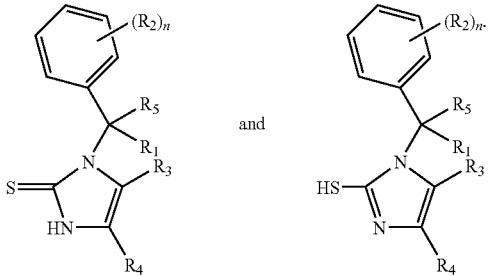

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

Whenever used hereinbefore or hereinafter that substituents can be selected each independently out of a list of numerous definitions, such as for example for $R_{7a}$ or $R_{7b}$, all possible combinations are intended which are chemically possible.

A first group of interesting compounds consists of those compounds of formula (I) wherein one or more of the following restrictions apply:
a) $R_1$ represents hydrogen, $C_{1-6}$alkyl, $C_{3-7}$cycloalkyl, aryl or heteroaryl;
b) $R_3$ represents hydrogen, cyano, $C_{1-6}$alkyl optionally substituted with hydroxy, C(=O)—O—$R_6$, C(=O)—$NR_{7a}R_{7b}$, S(=O)$_2$—$NR_{7a}R_{7b}$, C(=O)—$R_8$;
c) $R_4$ represents hydrogen, cyano, $C_{1-6}$alkyl optionally substituted with hydroxy, C(=O)—O—$R_6$, C(=O)—$NR_{7a}R_{7b}$, S(=O)$_2$—$NR_{7a}R_{7b}$, C(=O)—$R_8$;
d) $R_{7a}$ and $R_{7b}$ each independently represent hydrogen, $C_{1-6}$alkyl, amino, mono- or di($C_{1-4}$alkyl)amino, arylNH—, amino$C_{1-6}$alkyl or mono- or di($C_{1-4}$alkyl)amino $C_{1-6}$alkyl; or $R_{7a}$ and $R_{7b}$ taken together with the nitrogen to which they are attached form pyrrolidinyl, imidazolidinyl, pyrazolidinyl, piperidinyl, piperazinyl, morpholinyl or thiomorpholinyl; and
e) $R_5$ represents hydrogen;

A second group of interesting compounds consists of those compounds of formula (I) wherein one or more of the following restrictions apply:
a) each $R_2$ independently represents halo, $C_{1-6}$alkyl, $C_{1-6}$alkyloxy or polyhalo$C_{1-6}$alkyl;
b) $R_3$ represents hydrogen, cyano, $C_{1-6}$alkyl substituted with hydroxy, C(=O)—O—$R_6$, C(=O)—$NR_{7a}R_{7b}$, C(=S)—$NR_{7a}R_{7b}$ or C(=O)—$R_8$;
c) $R_4$ represents hydrogen, cyano, $C_{1-6}$alkyl optionally substituted with hydroxy or $C_{1-6}$alkyloxy, C(=O)—O—$R_6$ or C(=O)—$NR_{7a}R_{7b}$;
d) $R_3$ and $R_4$ taken together may form a bivalent radical of formula —C(=O)—NH—NH—C(=O)—;
e) $R_6$ represents hydrogen, $C_{1-6}$alkyl, hydroxy$C_{1-6}$alkyl or mono- or di($C_{1-4}$alkyl)aminocarbonyl$C_{1-6}$alkyl;
f) $R_{7a}$ and $R_{7b}$ each independently represent hydrogen, $C_{1-6}$alkyl, amino, $C_{1-6}$alkylcarbonylamino, aminocarbonylamino, $C_{1-6}$alkyloxy, —NH—C(O)—H or hydroxy$C_{1-6}$ alkyl; or $R_{7a}$ and $R_{7b}$ taken together with the nitrogen to which they are attached form pyrrolidinyl, piperidinyl, piperazinyl, morpholinyl or piperazinyl substituted with $C_{1-6}$alkyl;
g) $R_8$ represents $C_{1-6}$alkyl; and
h) n is 1, 2 or 3.

A third group of interesting compounds consists of those compounds of formula (I) wherein one or more of the following restrictions apply:
a) $R_1$ represents hydrogen, $C_{1-6}$alkyl, $C_{3-7}$cycloalkyl, aryl or heteroaryl;
b) each $R_2$ independently represents halo, $C_{1-6}$alkyl, $C_{1-6}$alkyloxy or polyhalo$C_{1-6}$alkyl;
c) $R_3$ represents hydrogen, cyano, $C_{1-6}$alkyl substituted with hydroxy, C(=O)—O—$R_6$, C(=O)—$NR_{7a}R_{7b}$ or C(=O)—$R_8$;
d) $R_4$ represents hydrogen, cyano, $C_{1-6}$alkyl optionally substituted with hydroxy, C(=O)—O—$R_6$ or C(=O)—$NR_{7a}R_{7b}$;
e) $R_6$ represents hydrogen, $C_{1-6}$alkyl, hydroxy$C_{1-6}$alkyl or mono- or di($C_{1-4}$alkyl)aminocarbonyl$C_{1-6}$alkyl;
f) $R_{7a}$ and $R_{7b}$ each independently represent hydrogen, $C_{1-6}$alkyl, amino; or $R_{7a}$ and $R_{7b}$ taken together with the nitrogen to which they are attached form pyrrolidinyl, piperidinyl, piperazinyl or morpholinyl;
g) $R_8$ represents $C_{1-6}$alkyl;
h) n is 1, 2 or 3; and
i) $R_5$ is hydrogen.

A fourth group of interesting compounds consists of those compounds of formula (I) wherein one or more of the following restrictions apply:
a) $R_1$ represents $C_{1-6}$alkyl, $C_{3-7}$cycloalkyl, $C_{1-6}$alkyloxy$C_{1-6}$alkyl, di($C_{1-6}$alkyl)amino$C_{1-6}$alkyl, aryl or heteroaryl;
b) $R_1$ represents hydrogen, $C_{1-6}$alkyl, $C_{3-7}$cycloalkyl, $C_{1-6}$alkyloxy$C_{1-6}$alkyl, di($C_{1-6}$alkyl)amino$C_{1-6}$alkyl or heteroaryl;
c) each $R_2$ independently represents halo, $C_{1-6}$alkyl, $C_{1-6}$alkyloxy, $C_{1-6}$alkylthio, polyhalo$C_{1-6}$alkyl, polyhalo$C_{1-6}$alkyloxy aminocarbonyl, amino, mono- or di($C_{1-4}$alkyl)amino, nitro, aryl or aryloxy;
d) $R_3$ represents hydrogen, cyano, $C_{1-6}$alkyl optionally substituted with $C_{1-6}$alkyloxy, C(=O)—O—$R_6$, C(=O)—$NR_{7a}R_{7b}$, C(=S)$NR_{7a}R_{7b}$, S(=O)$_2$—$NR_{7a}R_{7b}$ or C(=O)—$R_8$;
e) if $R_4$ is hydrogen then $R_3$ represents cyano, $C_{1-4}$alkyl optionally substituted with $C_{1-6}$alkyloxy, C(=O)—O—$R_6$, C(=O)—$NR_{7a}R_{7b}$, C(=S)—$NR_{7a}R_{7b}$, S(=O—$NR_{7a}R_{7b}$ or C(=O)—$R_8$;
f) $R_3$ and $R_4$ each independently represent hydrogen, cyano, hydroxy$C_{1-6}$alkyl, $C_{1-6}$alkyloxy$C_{1-6}$alkyl, C(=O)—O—$R_6$, C(=O)—$NR_{7a}R_{7b}$, C(=S)—$NR_{7a}R_{7b}$, S(=O)$_2$—$NR_{7a}R_{7b}$ or C(=O)—$R_8$; g) if $R_3$ represents C(=O)—O—$R_6$ or C(=O)—$NR_{7a}R_{7b}$ then $R_1$ is hydrogen, $C_{1-6}$alkyl, $C_{3-7}$cycloalkyl, $C_{1-6}$alkyloxy$C_{1-6}$alkyl, di($C_{1-6}$alkyl)amino$C_{1-6}$alkyl or heteroaryl.

A fifth group of interesting compounds consists of those compounds of formula (I) wherein one or more of the following restrictions apply:
a) $R_1$ represents hydrogen, $C_{1-6}$alkyl, cyclopropyl, cyclohexyl, $C_{1-6}$alkyloxy$C_{1-6}$alkyl, di($C_{1-6}$alkyl)amino$C_{1-6}$alkyl, phenyl or phenyl substituted with two substituents each independently selected from halo; in particular $C_{1-6}$alkyl;
b) n is 1, 2 and 3; in particular n is 2 and said two $R_2$ substituents are placed in position 3 and 4;
c) each $R_2$ independently represents halo or polyhalo$C_{1-6}$alkyl, in particular halo;
d) $R_3$ represents hydrogen, cyano, C(=O)—O—$R_6$, C(=O)—$NR_{7a}R_{7b}$ or C(=O)—$R_8$; in particular C(=O)—O—$R_6$;

e) $R_4$ represents hydrogen, cyano, $C_{1-6}$alkyl optionally substituted with hydroxy or $C_{1-6}$alkyloxy, C(=O)—O—$R_6$ or C(=O)—N$R_{7a}R_{7b}$; in particular C(=O)—O—$R_6$;

f) $R_3$ and $R_4$ taken together may form a bivalent radical of formula —C(=O)—NH—NH—C(=O)—;

g) $R_6$ represents hydrogen, $C_{1-6}$alkyl or hydroxy$C_{1-6}$alkyl; in particular $C_{1-6}$alkyl;

h) $R_{7a}$ represent hydrogen or $C_{1-6}$alkyl; and $R_{7b}$ represents hydrogen, $C_{1-6}$alkyl, amino, $C_{1-6}$alkylcarbonylamino, $C_{1-6}$alkyloxy or hydroxy$C_{1-6}$alkyl; or $R_{7a}$ and $R_{7b}$ taken together with the nitrogen to which they are attached form piperidinyl;

i) $R_8$ represents $C_{1-6}$alkyl;

j) $R_5$ is hydrogen.

A sixth group of interesting compounds consists of those compounds of formula (I) wherein one or more of the following restrictions apply:

a) $R_1$ represents hydrogen, $C_{1-6}$alkyl, cyclopropyl, cyclohexyl, phenyl or phenyl substituted with two substituents each independently selected from halo; in particular $C_{1-6}$alkyl;

b) n is 1, 2 and 3; in particular n is 2 and said two $R_2$ substituents are placed in position 3 and 4;

c) each $R_2$ independently represents halo or polyhalo$C_{1-6}$alkyl, in particular halo;

d) $R_3$ represents hydrogen, cyano, C(=O)—O—$R_6$, C(=O)—N$R_{7a}R_{7b}$ or C(=O)—$R_8$; in particular C(=O)—O—$R_6$;

e) $R_4$ represents hydrogen, cyano, $C_{1-6}$alkyl optionally substituted with hydroxy, C(=O)—O—$R_6$ or C(=O)—N$R_{7a}R_{7b}$; in particular C(=O)—O—$R_6$;

f) $R_6$ represents hydrogen, $C_{1-6}$alkyl or hydroxy$C_{1-6}$alkyl; in particular $C_{1-6}$alkyl;

g) $R_{7a}$ represent hydrogen or $C_{1-6}$alkyl; and $R_{7b}$ represents hydrogen, $C_{1-6}$alkyl or amino; or $R_{7a}$ and $R_{7b}$ taken together with the nitrogen to which they are attached form piperidinyl;

h) $R_8$ represents $C_{1-6}$alkyl and i) $R_5$ is hydrogen.

A seventh group of interesting compounds Consists of those compounds of formula (I) wherein both $R_3$ and $R_4$ are other than hydrogen.

An eight group of interesting compounds consists of those compounds of formula (I) wherein $R_4$ is hydrogen and $R_3$ is other than hydrogen; in particular $R_3$ represents cyano, C(=O)—O—$R_6$, C(=O)—N$R_{7a}R_{7b}$ or C(=O)—$R_8$.

A ninth group of interesting compounds consists of those compounds of formula (I) wherein $R_3$ is hydrogen and $R_4$ is other than hydrogen, in particular $R_4$ is cyano, $C_{1-6}$alkyl optionally substituted with hydroxy or $C_{1-6}$alkyloxy, C(=O)—O—$R_6$ or C(=O)—N$R_{7a}R_{7b}$.

A tenth group of interesting compounds consists of those compounds of formula (I) wherein $R_3$ is other than C(=O)—O—$R_6$ when $R_4$ is hydrogen.

An eleventh group of interesting compounds consists of those compounds of formula (I) wherein $R_3$ is hydrogen.

A group of preferred compounds consists of those compounds of formula (I) wherein $R_1$ represents hydrogen, $C_{1-6}$alkyl, $C_{3-7}$cycloalkyl, aryl or heteroaryl; $R_3$ represents hydrogen, cyano, $C_{1-6}$alkyl optionally substituted with hydroxy, C(=O)O—$R_6$, C(=O)—N$R_{7a}R_{7b}$, S(=O)$_2$—N$R_{7a}R_{7b}$, C(=O)—$R_8$; $R_4$ represents hydrogen, cyano, $C_{1-6}$alkyl optionally substituted with hydroxy, C(=O)—O—$R_6$, C(=O)—N$R_{7a}R_{7b}$, S(=O)$_2$—N$R_{7a}R_{7b}$, C(=O)—$R_8$; $R_{7a}$ and $R_{7b}$ each independently represent hydrogen, $C_{1-6}$alkyl, amino, mono- or di($C_{1-4}$alkyl)amino, arylNH—, amino$C_{1-6}$alkyl or mono- or di($C_{1-4}$alkyl)amino$C_{1-6}$alkyl; or $R_{7a}$ and $R_{7b}$ taken together with the nitrogen to which they are attached form pyrrolidinyl, imidazolidinyl, pyrazolidinyl, piperidinyl, piperazinyl, morpholinyl or thiomorpholinyl; and $R_5$ represents hydrogen.

Another group of preferred compounds consists of those compounds of formula (I) wherein each $R_2$ independently represents halo, $C_{1-6}$alkyl, $C_{1-6}$alkyloxy or polyhalo$C_{1-6}$alkyl; $R_3$ represents hydrogen, cyano, $C_{1-6}$alkyl substituted with hydroxy, C(=O)—O—$R_6$, C(=O)—N$R_{7a}R_{7b}$, C(=S)—N$R_{7a}R_{7b}$ or C(=O)—$R_8$; $R_4$ represents hydrogen, cyano, $C_{1-6}$alkyl optionally substituted with hydroxy or $C_{1-6}$alkyloxy, C(=O)—O—$R_6$ or C(=O)—N$R_{7a}R_{7b}$; $R_3$ and $R_4$ taken together may form a bivalent radical of formula —C(=O)—NH—NH—C(=O)—; $R_6$ represents hydrogen, $C_{1-6}$alkyl, hydroxy$C_{1-6}$alkyl or mono- or di($C_{1-4}$alkyl)aminocarbonyl$C_{1-6}$alkyl; $R_{7a}$ and $R_{7b}$ each independently represent hydrogen, $C_{1-6}$alkyl, amino, $C_{1-6}$alkylcarbonylamino, aminocarbonylamino, $C_{1-6}$alkyloxy, —NH—C(O)—H or hydroxy$C_{1-6}$alkyl; or $R_{7a}$ and $R_{7b}$ taken together with the nitrogen to which they are attached form pyrrolidinyl, piperidinyl, piperazinyl, morpholinyl or piperazinyl substituted with $C_{1-6}$alkyl; $R_8$ represents $C_{1-6}$alkyl; and n is 1, 2 or 3.

A further group of preferred compounds consists of those compounds of formula (I) wherein $R_1$ represents hydrogen, $C_{1-6}$alkyl, $C_{3-7}$cycloalkyl, aryl or heteroaryl; each $R_2$ independently represents halo, $C_{1-6}$alkyl, $C_{1-6}$alkyloxy or polyhalo$C_{1-6}$alkyl; $R_3$ represents hydrogen, cyano, $C_{1-6}$alkyl substituted with hydroxy, C(=O)—O—$R_6$, C(=O)—N$R_{7a}R_{7b}$ or C(=O)—$R_8$; $R_4$ represents hydrogen, cyano, $C_{1-6}$alkyl optionally substituted with hydroxy, C(=O)—O—$R_6$ or C(=O)—N$R_{7a}R_{7b}$; $R_6$ represents hydrogen, $C_{1-6}$alkyl, hydroxy$C_{1-6}$alkyl or mono- or di($C_{1-4}$alkyl)aminocarbonyl$C_{1-6}$alkyl; $R_{7a}$ and $R_{7b}$ each independently represent hydrogen, $C_{1-6}$alkyl, amino; or $R_{7a}$ and $R_{7b}$ taken together with the nitrogen to which they are attached form pyrrolidinyl, piperidinyl, piperazinyl or morpholinyl; $R_8$ represents $C_{1-6}$alkyl; n is 1, 2 or 3; and $R_5$ represents hydrogen.

A group of more preferred compounds consists of those compounds of formula (I) wherein $R_1$ represents hydrogen, $C_{1-6}$alkyl, cyclopropyl, cyclohexyl, $C_{1-6}$alkyloxy$C_{1-6}$alkyl, di($C_{1-6}$alkyl)amino$C_{1-6}$alkyl, phenyl or phenyl substituted with two substituents each independently selected from halo; n is 1, 2 and 3; each $R_2$ independently represents halo or polyhalo$C_{1-6}$alkyl; $R_3$ represents hydrogen, cyano, C(=O)—O—$R_6$, C(=O)—N$R_{7a}R_{7b}$ or C(=O)—$R_8$; $R_4$ represents hydrogen, cyano, $C_{1-6}$alkyl optionally substituted with hydroxy or $C_{1-6}$alkyloxy, C(=O)—O—$R_6$ or C(=O)—N$R_{7a}R_{7b}$; $R_3$ and $R_4$ taken together may form a bivalent radical of formula —C(=O)—NH—NH—C(=O)—; $R_6$ represents hydrogen, $C_{1-6}$alkyl or hydroxy$C_{1-6}$alkyl; $R_{7a}$ represent hydrogen or $C_{1-6}$alkyl; and $R_{7b}$ represents hydrogen, $C_{1-6}$alkyl, amino, $C_{1-6}$alkylcarbonylamino, $C_{1-6}$alkyloxy or hydroxy$C_{1-6}$alkyl; or $R_{7a}$ and $R_{7b}$ taken together with the nitrogen to which they are attached form piperidinyl; $R_8$ represents $C_{1-6}$alkyl; and $R_5$ represents hydrogen.

A group of more preferred compounds consists of those compounds of formula (I) wherein $R_1$ represents hydrogen, $C_{1-6}$alkyl, cyclopropyl, cyclohexyl, phenyl or phenyl substituted with two substituents each independently selected from halo; n is 1, 2 and 3; $R_3$ represents hydrogen, cyano, C(=O)—O—$R_6$, C(=O)—N$R_{7a}R_{7b}$ or C(=O)—$R_8$; $R_4$ represents hydrogen, cyano, $C_{1-6}$alkyl optionally substituted with hydroxy, C(=O)—O—$R_6$ or C(=O)—N$R_{7a}R_{7b}$; $R_6$ represents hydrogen, $C_{1-6}$alkyl or hydroxy$C_{1-6}$alkyl; $R_{7a}$ represent hydrogen or $C_{1-6}$alkyl; and $R_{7b}$ represents hydrogen, $C_{1-6}$alkyl or amino; or $R_{7a}$ and $R_{7b}$ taken together with the nitrogen to which they are attached form piperidinyl; $R_8$ represents $C_{1-6}$alkyl and $R_5$ represents hydrogen.

A group of even more preferred compounds consists of those compounds of formula (a) wherein $R_1$ represents $C_{1-6}$alkyl; n is 2; each $R_2$ independently represents halo; $R_3$ represents C(=O)—O—$R_6$; $R_6$ represents $C_{1-6}$alkyl; and $R_5$ represents hydrogen.

The most preferred compounds are compound No 37, compound No 39 and compound No 46.

In general compounds of formula (I) wherein $R_3$ is other than hydrogen, said $R_3$ being represented by $R_{3'}$ and $R_4$ is hydrogen, said compounds being represented by formula (I-a), can be prepared by reacting an intermediate of formula (II) with HC(=O)—O—$CH_3$ (formic acid, methyl ester) in the presence of a suitable base, such as for example $NaOCH_3$ or $NaOC(CH_3)_3$, followed by treatment with a suitable acid, such as for example hydrochloric acid (36%) and the like, and KSCN in the presence of a suitable solvent, such as for example tetrahydrofuran.

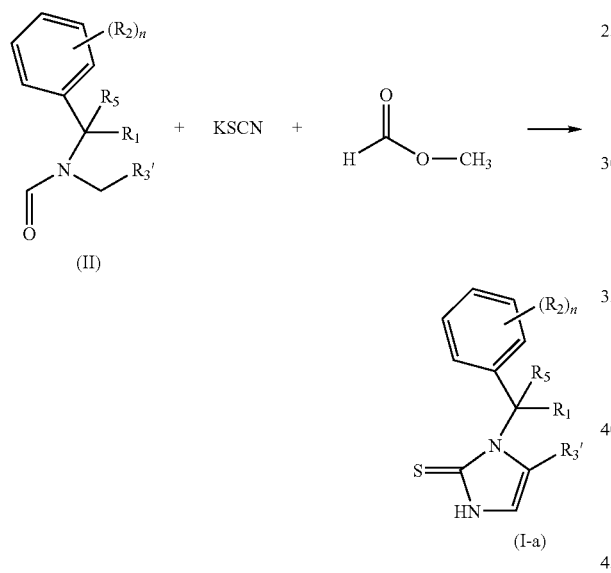

When starting from a stereoisomeric pure intermediate of formula (II), the above reaction results in the preparation of a stereoisomeric pure compound of formula (I-a).

When $R_{3'}$ in the intermediates of formula (II) represents CN, said intermediates being represented by formula (II-a), the above reaction may result in a compound of formula (I-a-1) and (I-a-2) as represented below.

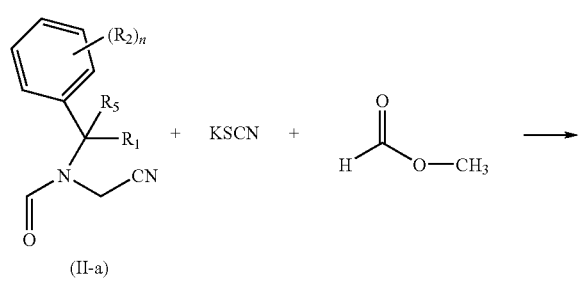

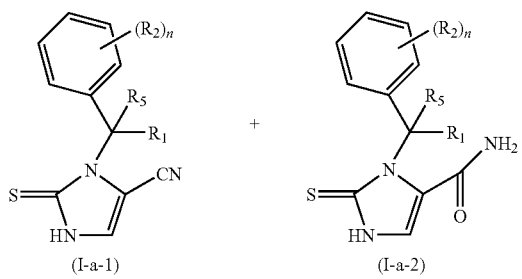

Compounds of formula (I) wherein $R_3$ and $R_4$ are both other than hydrogen, said $R_3$ and $R_4$ substituents being represented by $R_{3'}$ and $R_{4'}$, and said compounds being represented by formula (I-b), can be prepared by reacting an intermediate of formula (II) with an intermediate of formula (III) in the presence of a suitable base, such as for example $NaOCH_3$ or $NaOC(CH_3)_3$, followed by treatment with a suitable acid, such as for example hydrochloric acid (36%) and the like, and KSCN in the presence of a suitable solvent, such as for example tetrahydrofuran.

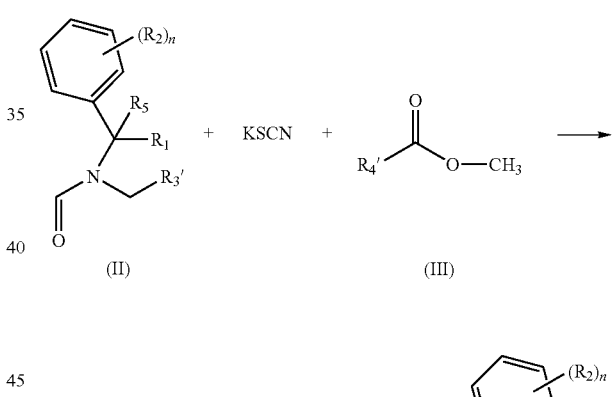

The above reaction can also be performed by using $R_{4'}$—C(=O)—Cl or $R_{4'}$—C(=O)—O—$C(CH_3)_3$ instead of an intermediate of formula (III).

When $R_{3'}$ and $R_{4'}$ in the intermediates of formula (II) and (II) represent C(=O)—O—$C_{1-6}$alkyl, said intermediates being represented by formula (I-b) and (III-b), the above reaction may result in a compound of formula (I-b-1) and (I-b-2) as represented below.

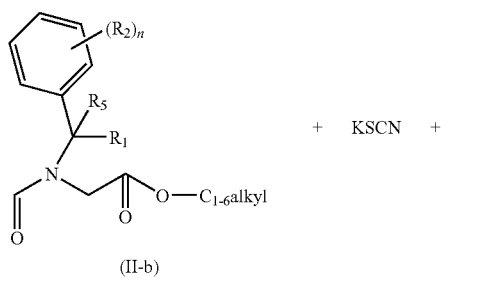

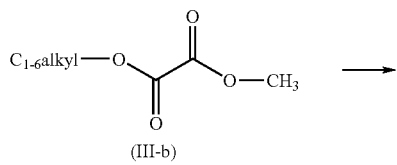

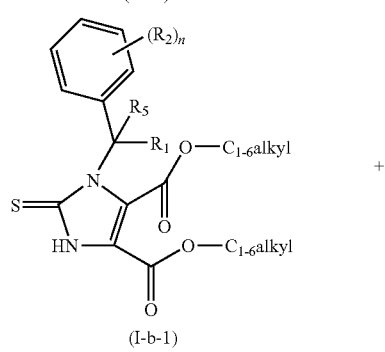

Compounds of formula (I) wherein $R_3$ represents $R_{3'}$, said compounds being represented by formula (I-c), can also be prepared by reacting an intermediate of formula (IV) with KSCN in the presence of a suitable acid, such as for example hydrochloric acid and the like, and a suitable solvent, such as for example an alcohol, e.g. ethanol.

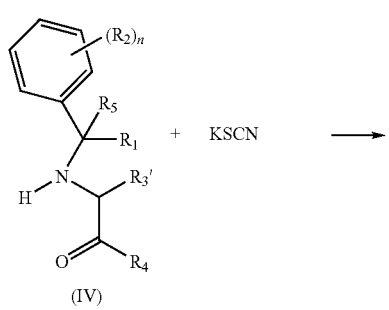

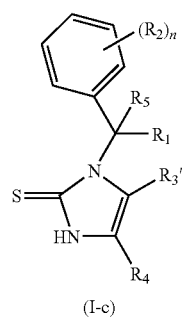

Compounds of formula (I) wherein both $R_3$ and $R_4$ are cyano and $R_5$ is hydrogen, said compounds being represented by formula (I-b-3), can be prepared by reacting an intermediate of formula (V) with Cl—C(=S)—Cl in the presence of a suitable base, such as for example N,N-diethylethanamine, and a suitable solvent, such as for example methylene chloride.

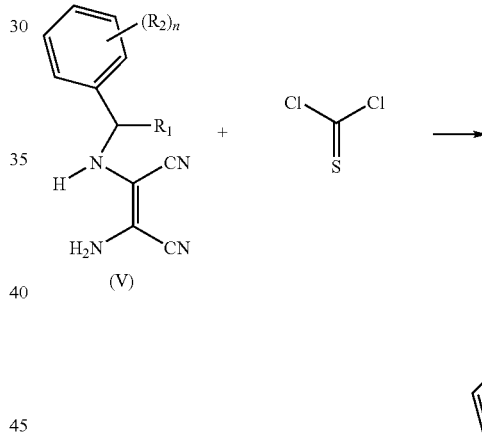

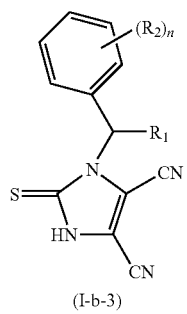

Compounds of formula (I-a) wherein $R_{3'}$ represents C(=O)—$NR_{7a}R_{7b}$, said compounds being represented by formula (I-a-3), can be prepared by reacting an intermediate of formula (VI) wherein $W_1$ represents a suitable leaving group, such as for example a halogen, e.g. chloro and the like, with an intermediate of formula (VII), such as for example $NH_3$ (or acetic acid ammonium salt), pyrrolidine and the like, in the presence of a suitable solvent, such as for example acetone, tetrahydrofuran, N,N-dimethylformamide and the like.

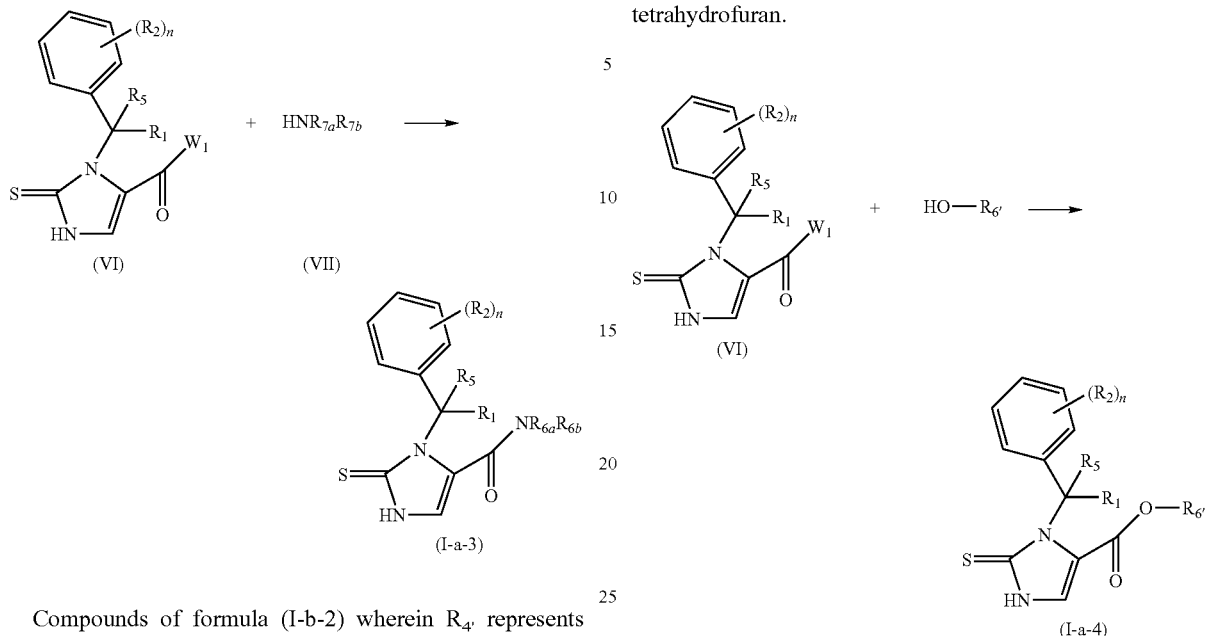

Compounds of formula (I-b-2) wherein $R_{4'}$ represents $C(=O)-NR_{7a}R_{7b}$, said compounds being represented by formula (I-b-4), can be prepared by reacting an intermediate of formula (XX) with an intermediate of formula (VII), such as for example $NH_3$ (or acetic acid ammonium salt) pyrrolidine and the like, in the presence of a suitable solvent, such as for example acetone, tetrahydrofuran, N,N-dimethylformamide and the like.

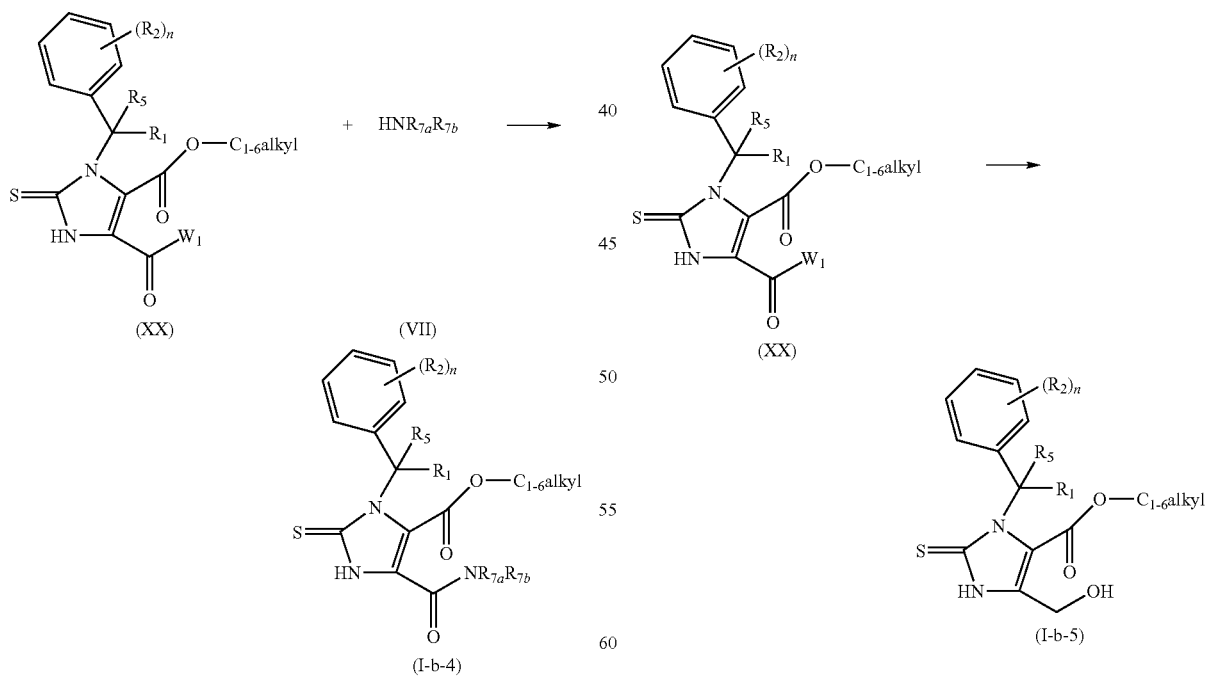

Compounds of formula (I-a) wherein $R_{3'}$ represents $C(=O)-O-R_{6'}$, wherein $R_{6'}$ represents $C_{1-6}$alkyl or hydroxy$C_{1-6}$alkyl, said compounds being represented by formula (I-a-4), can be prepared by reacting an intermediate of formula (VI) with an appropriate alcohol of formula $HO-R_{6'}$ in the presence of a suitable solvent, such as for example tetrahydrofuran.

Compounds of formula (I-b-2) wherein $R_{4'}$ represents $CH_2-OH$, said compounds being represented by formula (I-b-5), can be prepared by reacting an intermediate of formula (XX) with a suitable reducing agent, such as for example $NaBH_4$ in the presence of a suitable solvent, such as for example tetrahydrofuran.

Compounds of formula (I) wherein $R_3$ is hydrogen and $R_4$ is $C(=O)-O-C_{1-6}$alkyl, said compounds being represented by formula (I-d), can be prepared by reacting an intermediate of formula (VIII) wherein $W_2$ represents a suitable leaving group, such as for example $C_{1-6}$alkylthio, $C_{1-6}$alkyloxy or $C_6H_5$—$CH_2$—S—, with an alcoholate base, such as for example $NaOC_{1-6}$alkyl, in the presence of the corresponding alcohol $C_{1-6}$alkyl-OH.

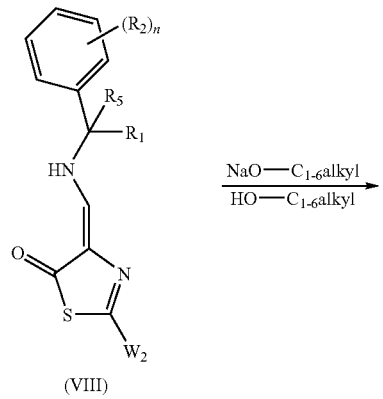

(VIII)

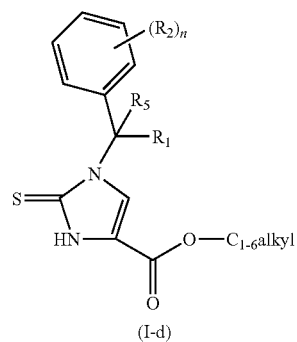

(I-d)

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert. butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I-a), (I-b) or (I-d) wherein $R_{3'}$ and/or $R_{4'}$ represent C(=O)—O—$C_{1-6}$alkyl, may be converted into a compound of formula (I-a), (I-b) or (I-d) wherein $R_{3'}$ and/or $R_{4'}$ represent $CH_2$—OH by reaction with a suitable reducing agent, such as for example $LiHBEt_3$ in the presence of a suitable solvent, such as for example tetrahydrofuran.

Compounds of formula (I-a), (I-b) or (I-d) wherein $R_{3'}$ and/or $R_{4'}$ represent C(=O)—O—$C_{1-6}$alkyl, can also be converted into a compound of formula (I-a), (I-b) or (I-d) wherein $R_{3'}$ and/or $R_{4'}$ represent C(=O)—OH by reaction with a suitable base, such as NaOH, in the presence of a suitable solvent, such as for example $H_2O$, tetrahydrofuran or an appropriate alcohol, e.g. methanol and the like.

Compounds of formula (I-a), (I-b) or (I-d) wherein $R_{3'}$ and/or $R_{4'}$ represent C(=O)—O—$C_{1-6}$alkyl, can also be converted into a compound of formula (I-a), (I-b) or (I-d) wherein $R_{3'}$ and/or $R_{4'}$ represent C(=O)—$NR_{7a}R_{7b}$, by reaction with the appropriate base of formula $NHR_{7a}R_{7b}$ in a suitable solvent, such as for example $H_2O$.

Compounds of formula (I-a), (I-b) or (I-d) wherein $R_{3'}$ or $R_{4'}$ represent cyano or C(=O)—O—$C_{1-6}$alkyl, can be converted into a compound of formula (I-a), (I-b) or (I-d) wherein $R_{3'}$ or $R_{4'}$ represent aminocarbonyl by reaction with $NH_4OH$.

Compounds of formula (I-a), (I-b) or (I-d) wherein $R_{3'}$ or $R_{4'}$ represent cyano, can be converted into a compound of formula (I-a), (I-b) or (I-d) wherein $R_{3'}$ or $R_{4'}$ represent C(=S)$NR_{7a}R_{7b}$ by reaction with hydrogen sulfide in the presence of N-ethyl-N-(1-methylethyl)-2-propanamine in a suitable solvent such as pyridine.

Compounds of formula (I-a), (I-b) or (I-d) wherein $R_{3'}$ and/or $R_{4'}$ represent C(=O)—$NR_{7a}R_{7b}$ can be converted into compounds of formula (I-a), (I-b) or (I-d) wherein $R_{3'}$ and/or $R_{4'}$ represent C(=O)—$C_{1-6}$alkyl by reaction with chloro$C_{1-6}$alkyl-magnesium in a suitable solvent such as tetrahydrofuran.

Compounds of formula (I-a), (I-b) or (I-d) wherein $R_{3'}$ and/or $R_{4'}$ represent C(=O)—$C_{1-6}$alkyl can be converted into compounds of formula (I-a), (I-b) or (I-d) wherein $R_{3'}$ and/or $R_{4'}$ represent hydroxy$C_{1-6}$alkyl by reaction with a suitable reducing agent such as $NaBH_4$ in the presence of a suitable solvent such as methanol.

Compounds of formula (I-b) wherein $R_{3'}$ and $R_{4'}$ represent C(=O)—O—$C_{1-6}$alkyl, can be converted into a compound of formula (I-b) wherein $R_{3'}$ and $R_{4'}$ taken together form a bivalent radical of formula —C(=O)—NH—NH—C(=O)—, by reaction with hydrazine monohydrate in a suitable solvent, such as for example $H_2O$.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures.

Intermediates of formula (II) can be prepared by reacting an intermediate of formula (IX) with a H—C(=O)— introducing agent, such as for example formic acid or n-butyl formate, in the presence of a suitable solvent, such as for example xylene.

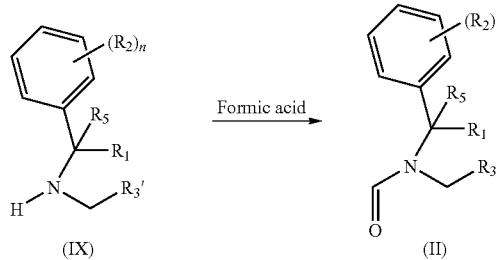

The above reaction may result in stereochemically pure intermediates of formula (II) when starting from stereochemically pure intermediates of formula (IX).

Intermediates of formula (IX) can be prepared by reacting an intermedtae of formula (X) with an intermediate of formula (XI) wherein $W_3$ represents a suitable leaving group, such as for example a halogen, e.g. bromo and the like, in the presence of a suitable base, such as for example N,N-diethylethanamine or N,N-diisopropylethanamine, and in the presence of a suitable solvent, such as for example N,N-dimethylformamide.

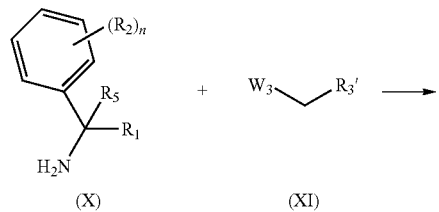

The above reaction may result in stereochemically pure intermediates of formula (IX) when starting from stereochemically pure intermediates of formula (X).

Intermediates of formula (X) wherein $R_5$ represents hydrogen herein referred to as intermediates of formula (X-a) can be prepared by reducing an intermediate of formula (XII) in the presence of a suitable reducing agent, such as $H_2$, a suitable catalyst, such as for example Raney Nickel, a suitable catalyst poison, such as for example a thiophene solution, and a suitable solvent, such as for example an alcohol, e.g. methanol, in the presence of a suitable base, e.g. $NH_3$. Alternatively, said reaction can also be performed in the presence of Zn and a suitable acid, such as for example acetic acid.

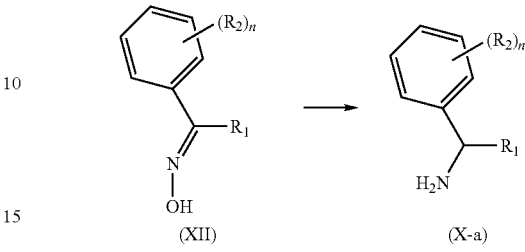

Intermediates of formula (XII) can be prepared by reacting an intermediate of formula (XIII) with $NH_2$—OH in the presence of a suitable base, such as for example $NaOC(=O)CH_3$, and a suitable solvent, such as for example an alcohol, e.g. methanol.

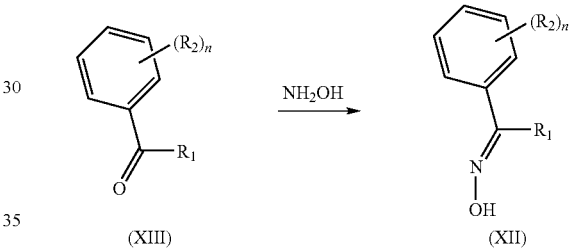

Alternatively to the methods described above, intermediates of formula (X) can also be prepared from an azido derivative of formula (XIV) by reaction with triphenylphosphine in the presence of a suitable solvent, such as for example tetrahydrofuran and $H_2O$.

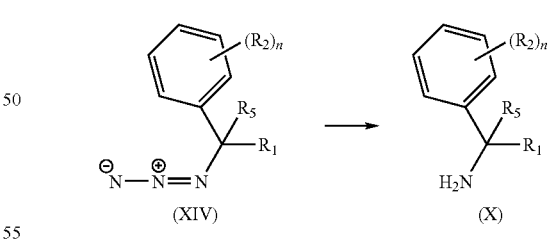

Intermediates of formula (X) can also be prepared from an intermediate of formula (XIV) by catalytic hydrogenation in the presence of $H_2$, a suitable catalyst, such as for example Pt/C (5%), and a suitable solvent, such as for example an alcohol, e.g. methanol.

Intermediates of formula (XIV) can be prepared by reacting an intermediate of formula (XV) with phosphorazidic acid diphenylester in the presence of 2,3,4,6,7,8,9,10-Octahydropyrimido[1,2-a]azepine and a suitable solvent, such as for example toluene.

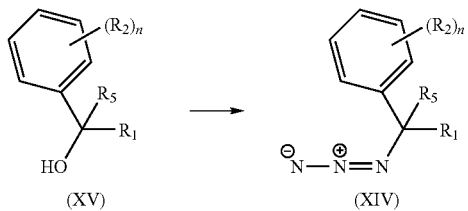
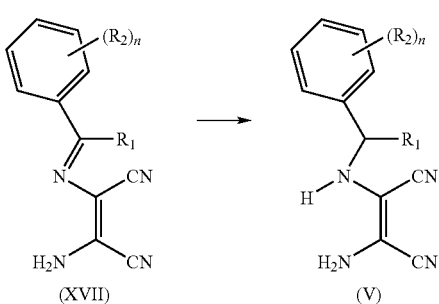

Intermediates of formula (XV) wherein $R_1$ is $C_{1-6}$alkyl and wherein $R_5$ is hydrogen, said intermediates being represented by formula (XV-a), can be prepared by reacting an intermediate of formula (XIII) wherein $R_1$ represents hydrogen, said intermediates being represented by formula (XIII-a), with $(C_{1-6}alkyl)_2Zn$, N,N'-1,2-cyclohexanediylbis[1,1,1-trifluoro]methanesulfonamide, Ti(i-PrO)$_4$ and toluene.

Intermediates of formula (XVII) can be prepared by reacting an intermediate of formula (XIII) with 2,3-diamino-2-butenedinitrile in the presence of $P_2O_5$ (phosphorus anhydride) and a suitable solvent.

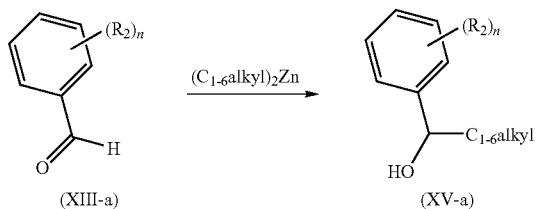
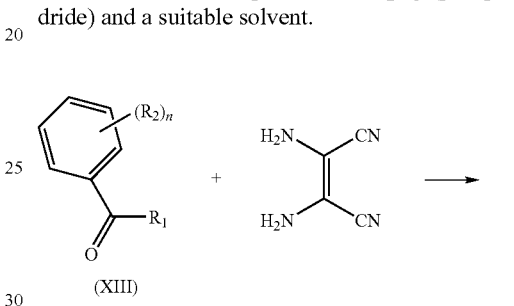

Intermediates of formula (IV) can be prepared by reacting an intermediate of formula (X) with an intermediate of formula (XVI) wherein $W_4$ represents a suitable leaving group, such as for example a halogen, e.g. chloro and the like, in the presence of a suitable base, such as for example N,N-diethylethanamine or N,N-diisopropylethylamine, and a suitable solvent, such as for example N,N-dimethylformamide or tetrahydrofuran.

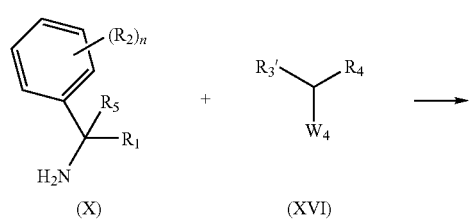

Intermediates of formula (V) can be prepared by reducing an intermediate of formula (XVII) in the presence of a suitable reducing agent, such as for example NaBH$_4$, and a suitable solvent, such as for example tetrahydrofuran and an alcohol, e.g. methanol.

Intermediates of formula (VI) wherein $W_1$ represents chloro, said intermediates being represented by formula (VI-a), can be prepared by reacting a compound of formula (I-a) wherein $R_3$' represents C(=O)—OH, said compound being represented by formula (I-a-5), with SOCl$_2$.

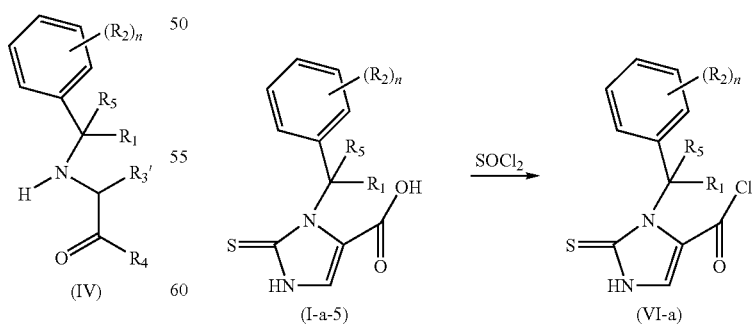

Intermediates of formula (XX) wherein $W_1$ represents chloro, said intermediates being represented by formula (XX-a), can be prepared by reacting a compound of formula (I-b-2) with SOCl$_2$.

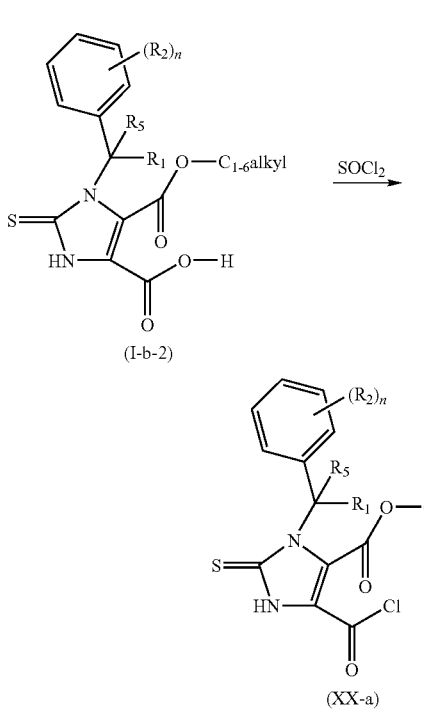

(I-b-2)

SOCl₂ →

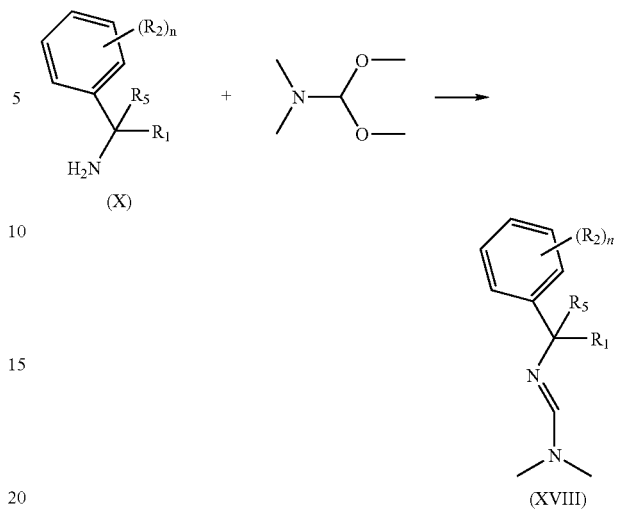

(X)

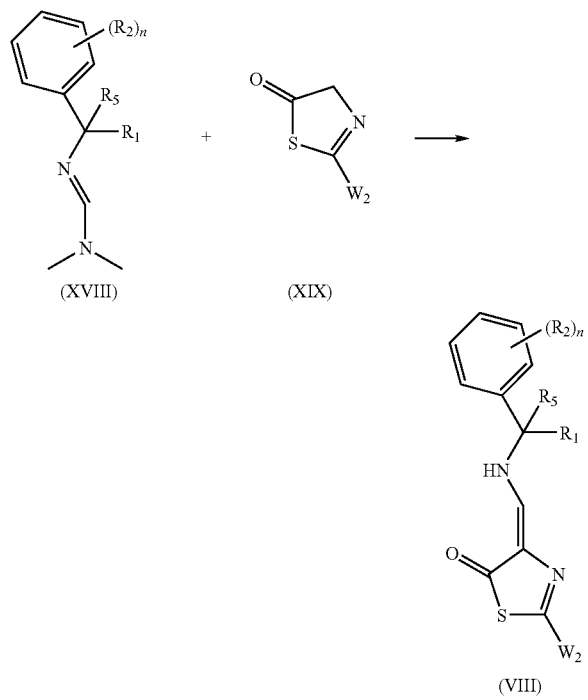

Intermediates of formula (VIII) can be prepared by reacting an intermediate of formula (XVIII) with an intermediate of formula (XIX) in the presence of a suitable solvent, such as for example toluene.

Intermediates of formula (XVIII) can be prepared by reacting an intermediate of formula (X) with 1,1-dimethoxy-N,N-dimethylmethanamine.

The compounds of formula (I) show CCR2 receptor antagonistic properties.

The C—C chemokine receptor 2 (CCR2) and its ligand monocyte chemoattractant (chemotactic) protein (MCP-1; in new chemokine nomenclature also called CCL2) are recognized to be implicated in both acute and chronic inflammatory processes.

Chemokines (contraction of "chemotactic cytokines") are most important regulators of leukocyte trafficking. This biological role is exerted by interacting—on target cells—with seven-transmembrane-domain receptors that are coupled to heterodimeric G proteins. Chemokines are mainly grouped into 2 families (C—C or C—X—C family) dependent on the presence of an amino acid (represented by X) between the two conserved cysteine residues (represented by C) near the amino terminus. In general, chemokines from the C—C family attract monocytes, macrophages, T cells and NK cells.

A chemokine, which acts through the CCR2 receptor, is MCP-1 as indicated above. Therefore, the CCR2 receptor is also known as the Chemoattractant protein-1 receptor. MCP-2 and MCP-3 may also act, at least in part, through this receptor.

It is recognized that the CCR2 receptor and MCP-1 play a role in the pathophysiology of various inflammatory diseases. Therefore, CCR2 receptor antagonists, which block the CCR2 receptor, have potential as pharmaceutical agents to combat inflammatory conditions such as arthritis, osteoarthritis, rheumatoid arthritis, glomerular nephritides, lung fibrosis, sarcoidosis, vasculitis, hepatitis, inflammatory conditions of the brain such as Alzheimer's disease, restenosis, alveolitis, asthma, atherosclerosis, psoriasis, delayed-type hypersensitivity reactions of the skin, inflammatory bowel disease, multiple sclerosis, chronic obstructive pulmonary disease (COPD), uveitis. CCR2 receptor antagonists may also be useful to treat autoimmune diseases such as diabetes or transplant rejection, stroke, reperfusion injury, ischemia and myocardial infraction.

The compounds of the present invention may also be used to inhibit the entry of Human Immunodeficiency Virus (IV) into monocytes and lymphocytes, thereby having a therapeutic role in the treatment of AIDS (Acquired Immunodeficiency Syndrome).

The CCR2 receptor exists in two isoforms, namely the CCR2A and the CCR2B receptor.

Due to their CCR2 receptor antagonistic activity, in particular their CCR2B receptor antagonistic activity, the compounds of formula (I), their N-oxides, pharmaceutically acceptable addition salts, quaternary amines and stereochemically isomeric forms are useful in the treatment or prevention of diseases or conditions mediated through the activation of the CCR2 receptor, in particular the CCR2B receptor. Diseases or conditions related to an activation of the CCR2 receptor comprise arthritis, osteoarthritis, rheumatoid arthritis, glomerular nephritides, lung fibrosis, sarcoidosis, vasculitis, hepatitis, inflammatory conditions of the brain such as Alzheimer's disease, restenosis, alveolitis, asthma, atherosclerosis, psoriasis, delayed-type hypersensitivity reactions of the skin, inflammatory bowel disease, multiple sclerosis, chronic obstructive pulmonary disease (COPD), uveitis, auto-immune diseases (diabetes, transplant rejection), stroke, reperfusion injury, ischemia, myocardial infraction. In particular, the compounds of formula (I) are useful in the treatment or prevention of inflammatory diseases and autoimmune diseases, especially rheumatoid arthritis, atherosclerosis, multiple sclerosis, inflammatory bowel disease and chronic obstructive pulmonary disease (COPD).

In view of the above-described pharmacological properties, the compounds of formula (I), their N-oxides, pharmaceutically acceptable addition salts, quaternary amines and stereochemically isomeric forms, may be used as a medicine. In particular, the present compounds can be used for the manufacture of a medicament for treating or preventing diseases mediated through activation of the CCR2 receptor, in particular the CCR2B receptor. More in particular, the compounds of the invention can be used for the manufacture of a medicament for treating or preventing inflammatory diseases, especially rheumatoid arthritis, atherosclerosis, multiple sclerosis, inflammatory bowel disease and chronic obstructive pulmonary disease (COPD).

In view of the utility of the compounds of formula (I), there is provided a method of treating warm-blooded animals, including humans, suffering from or a method of preventing warm-blooded animals, including humans, to suffer from diseases mediated through activation of the CCR2 receptor, in particular mediated through the CCR2B receptor. Said methods comprise the administration of an effective amount of a compound of formula (I), a N-oxide form, a pharmaceutically acceptable addition salt, a quaternary amine or a possible stereoisomeric form thereof, to warm-blooded animals, including humans.

The blockade of the CCR2 receptor by the present compounds of formula (I) inhibits the normal function of MCP-1. Therefore, the present compounds can also be described as MCP-1 inhibitors and hence can be used to prevent or treat diseases mediated through MCP-1.

The present invention also provides compositions for preventing or treating diseases mediated through activation of the CCR2 receptor, in particular the CCR2B receptor. Said compositions comprise a therapeutically effective amount of a compound of formula (I) and a pharmaceutically acceptable carrier or diluent.

The compounds of the present invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The compounds of the present invention may also be topically administered in the form of drops, in particular eye drops. Said eye drops may be in the form of a solution or a suspension. Any system developed for the delivery of solutions or suspensions as eye drops are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of formula (I) may also be used in combination with other conventional anti-inflammatory or immunosuppressive agents, such as steroids, cyclooxygenase-2 inhibitors, non-steroidal-anti-inflammatory drugs, TNF-α antibodies, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, valdecoxib, infliximab, leflunomide, etanercept, CPH 82, methotrexate, sulfasalazine, antilymphocytory immunoglobulines, antithymocytory immunoglobulines, azathioprine, cyclosporine, tacrolimus substances, ascomycin, rapamycin, muromonab-CD3.

Thus, the present invention also relates to the combination of a compound of formula (I) and another anti-inflammatory or immunosuppressive agent. Said combination may be used as a medicine. The present invention also relates to a product containing (a) a compound of formula (I), and (b) another anti-inflammatory or immunosuppressive compound, as a combined preparation for simultaneous; separate or sequential use in the treatment of diseases mediated through activation of the CCR2 receptor, in particular mediated through the CCR2B receptor. The different drugs in such products may be combined in a single preparation together with pharmaceutically acceptable carriers. Alternatively, such products may comprise, for example, a kit comprising a container with a suitable composition containing a compound of formula (I) and another container with a composition containing another anti-inflammatory or immunosuppressive compound. Such a product may have the advantage that a physician can select on the basis of the diagnosis of the patient to be treated the appropriate amounts of each component and the sequence and timing of the administration thereof.

The following examples are intended to illustrate the present invention.

Experimental Part

Hereinafter, "DIPE" is defined as diisopropyl ether, "DMA" is defined as N,N-dimethylacetamide, "DMF" is defined as N,N-dimethylformamide and "THF" is defined as tetrahydrofuran, 'SOCl$_2$' means thionyl chloride, 'EtOH' means ethanol, 'EtOAc' means ethyl acetate, 'Et$_2$O' means diethyl ether, 'Ti(iPrO)$_4$' means tetrakis(isopropanolato)titanium, 'P(Ph)$_3$' means triphenyl-phosphine, and 'Et$_3$N' means triethylamine.

A. Preparation of the Intermediates

EXAMPLE A1 a. Preparation of Intermediate 1

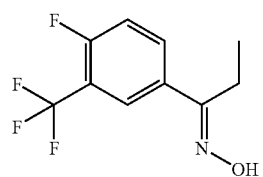

1-[4-fluoro-3-(trifluoromethyl)phenyl]-1-propanone (0.0441 mol) in methanol p.a. (200 ml) was stirred on an ice bath. NaOAc (0.0883 mol) was added, then hydroxylamine-.hydrochloride (0.0574 mol) was added. The reaction mixture was stirred at 0° C. for 90 minutes and at room temperature for 18 hours. The solvent was evaporated, the residue was stirred in CH$_2$Cl$_2$ and washed with a 10% aq. NaHCO$_3$ solution. The organic layer was separated, dried (MgSO$_4$), filtered and the solvent was evaporated, then co-evaporated with toluene (2×). Yield: intermediate 1.

b. Preparation of Intermediate 2

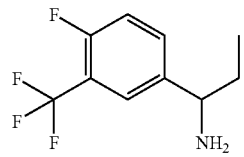

A solution of intermediate 1 (0.044 mol) in CH$_3$OH/NH$_3$ (7N) (250 ml) was hydrogenated at 14° C. with Raney Nickel (cat. quant.) as a catalyst in the presence of thiophene solution (1 ml). After uptake of H$_2$ (2 equiv., gas), the catalyst was filtered off and washed with CH$_3$OH. The filtrate was evaporated, then co-evaporated 2 times with toluene. The residue was dissolved in 2-propanol (75 ml) and converted into the hydrochloric acid salt (1:1) with HCl/2-propanol (25 ml, 6N). The solvent was evaporated and the precipitate (salt) was stirred in DIPE (100 ml), filtered off, washed, then dried (vac., 50° C.). Yield: 9.67 g of intermediate 2 (85.3%).

c. Preparation of Intermediate 3

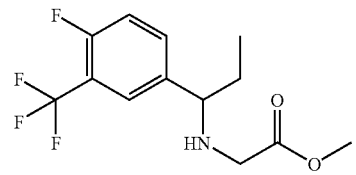

A solution of intermediate 2 (0.373 mol) and 2-bromoacetic acid methyl ester (0.045 mol) in DMF (p.a., dried on molecular sieves) (100 ml) was stirred under N$_2$-flow, then Et$_3$N (0.112 mol) was added and the reaction mixture was stirred for 20 hours at room temperature. Extra 2-bromoacetic acid methyl ester (1.25 ml) was added and the mixture was stirred for 68 hours at room temperature. The resulting precipitate was filtered off and washed with DMF. The precipitate/DMF mixture was filtered and the filtrate was treated with Et$_2$O (600 ml) and washed with H$_2$O (3 times 300 ml). The organic layer was separated, dried (MgSO$_4$), filtered and the solvent was evaporated, then co-evaporated 2 times with toluene. Yield: 10.94 g of intermediate 3.

d. Preparation of Intermediate 4

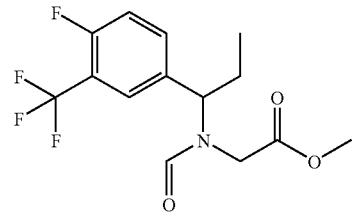

A solution of intermediate 3 (0.0372 mol) in formic acid (3.75 ml) and xylene, p.a. (110 ml) was stirred and refluxed for 6 hours, then the reaction mixture was stirred overnight, washed 2 times with H₂O, with a saturated aq. NaHCO₃ solution and with brine. The organic layer was separated, dried (MgSO₄), filtered and the solvent was evaporated. Yield: 11.3 g of intermediate 4.

EXAMPLE A2 a. Preparation of Intermediate 5

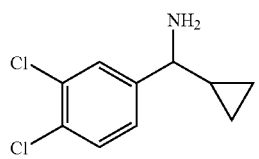

A mixture of cyclopropyl(3,4-dichlorophenyl)methanone oxime (0.16 mol) and Zn (75 g) in acetic acid (750 ml) was stirred at room temperature for 18 hours, then the reaction mixture was filtered over celite and the filtrate was evaporated. The residue was stirred in H₂O and dissolved, then the solution was treated with Na₂CO₃ and extracted with CH₂Cl₂. The organic layer was separated, dried, filtered and the solvent was evaporated. The residue was dissolved in 2-propanol and converted into the hydrochloric acid salt (1:1) with HCl/2-propanol. The precipitate was filtered off, washed with DIPE, then dried. Yield: 26.8 g of intermediate 5.

b. Preparation of Intermediate 6 and 7

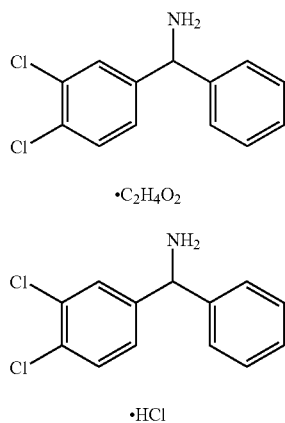

A mixture of (3,4-dichlorophenyl)phenylmethanone oxime (0.132 mol) and Zn (70 g) in acetic acid (700 ml) was stirred at room temperature for 18 hours, then the reaction mixture was filtered over decalite (to remove Zn) and the filtrate was evaporated. The residue was dissolved in H₂O (±150 ml) and converted into the acetic acid salt (1:1). The precipitate was filtered off and dried. Yield: 31 g of intermediate 6. The filtrate was treated with Na₂CO₃ and extracted with CH₂Cl₂. The organic layer was separated, dried, filtered and the solvent was evaporated. The residue was dissolved in 2-propanol and converted into the hydrochloric acid salt (1:1) with HCl/2-propanol. The precipitate was filtered off and dried. Yield: 5 g of intermediate 7.

EXAMPLE A3

Preparation of Intermediate 8

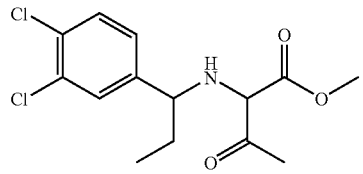

A mixture of 3,4-dichloro-α-ethylbenzenemethanamine (0.0098 mol) and 2-chloro-3-oxo-butanoic acid methyl ester (0.0166 mol) in Et₃N (5 ml) was stirred in DMF (50 ml) at room temperature for 18 hours, then the reaction mixture was poured out into H₂O (200 ml) and extracted with diethyl ether (150 ml). The ether layer was washed 3 times with H₂O (200 ml), dried (MgSO₄), filtered and the solvent was evaporated. Yield: intermediate 8.

EXAMPLE A4 a. Preparation of Intermediate 9

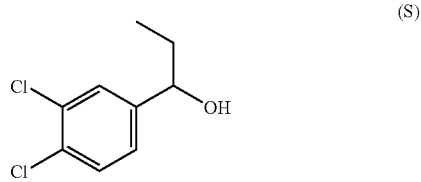

(S)

A mixture of N,N'-1,2-cyclohexanediylbis[1,1,1-trifluoromethanesulfonamide] (1R-trans) (0.189 g) and Ti(iPrO)₄ (0.030 mol) in toluene was degassed, placed under Ar flow, then stirred for 20 minutes at 40° C. The mixture was cooled to −78° C. and Et₂Zn (0.03 mol) was added dropwise. After 20 minutes, 3,4-dichlorobenzaldehyde (0.0250 mol) in toluene was added dropwise and the reaction mixture was allowed to warm up to 0° C. The mixture was stirred overnight at room temperature, then quenched with 2 N HCl. This mixture was extracted with CH₂Cl₂. The separated organic layer was washed, dried, filtered and the solvent evaporated. Yield: 5.1 g of intermediate 9 (S-isomer).

b. Preparation of Intermediate 10

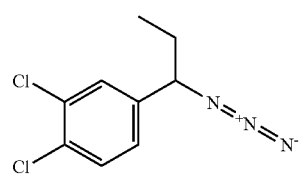

(R)

A mixture of intermediate 9 (0.025 mol) and phosphorazidic acid diphenyl ester (0.030 mol) in toluene (50 ml) was stirred at 0° C. 2,3,4,6,7,8,9,10-octahydropyrimido [1,2-a] azepine (0.030 mol) was added and the reaction mixture was stirred for 2 hours at 0° C., then overnight at room temperature. The reaction mixture was diluted with water and toluene. The organic layer was separated, washed once with water, once with 5% HCl, and the solvent was evaporated. Yield: intermediate 10 (R-isomer).

c. Preparation of Intermediate 11

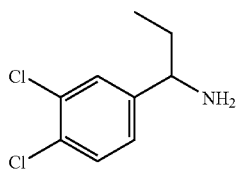

(R)

A mixture of intermediate 10 (0.025 mol), P(Ph)₃ (0.027 mol) in THF (70 ml) and H₂O (20 ml) was stirred overnight at room temperature. The solvent was evaporated. The residue was treated with 10% HCl. The acidic layer was washed with DIPE, then alkalized, followed by an extraction with CH₂Cl₂. The separated organic layer was dried, filtered and the solvent evaporated. The residue was purified by column chromatography over silica gel. The product fractions were collected and the solvent was evaporated. Yield: 1.1 g of intermediate 11 (R-isomer).

d. Preparation of Intermediate 12

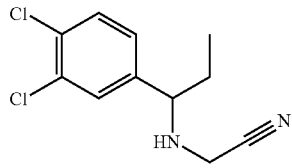

A solution of intermediate 11 (0.0116 mol) in Et₃N (0.013 mol) and DMF p.a. (20 ml) was stirred on an ice bath. A solution of chloroacetonitrile (0.0128 mol) in DMF p.a. (2.5 ml) was added dropwise. The reaction mixture was stirred at room temperature for 6 hours. Three more portions of chloroacetonitrile were added over the next 68 hours until the reaction was complete. The precipitate was filtered off. The filtrate was poured out into Et₂O (200 ml) and washed with H₂O/NaHCO₃ (10%; 100 ml) and H₂O (2×). The separated organic layer was dried (MgSO₄), filtered and the solvent was evaporated and coevaporated with toluene. The residue was purified over silica gel (eluent: CH₂Cl₂/MeOH 99:1). The desired fractions were collected and the solvent was evaporated and coevaporated with toluene. Yield: 2.3 g of intermediate 12 (81.6%).

e. Preparation of Intermediate 13

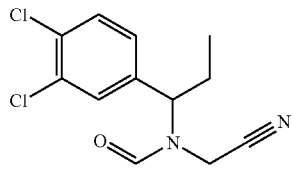

A mixture of intermediate 12 (0.00946 mol) and n-butylformate (15 ml) was stirred and refluxed for 4 days. The solvent was evaporated, then co-evaporated with toluene. Yield: 2.68 g of intermediate 13.

EXAMPLE A5

Preparation of Intermediate 14

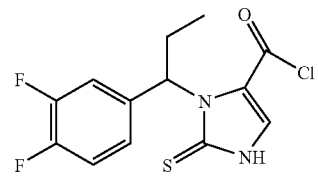

Compound 22 (prepared according B14) (0.0107 mol) was treated with SOCl₂ (20 ml) and the reaction mixture was stirred at 60° C. for 2 hours. Excess of SOCl₂ was evaporated, then the residue was co-evaporated 2 times with toluene (2×30 ml). Yield: intermediate 14.

EXAMPLE A6 a. Preparation of Intermediate 15

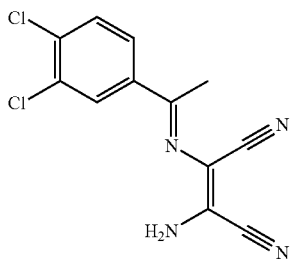

A mixture of 1-(3,4-dichlorophenyl)ethanone (0.0278 mol) and 2,3-diamino-2-butenedinitrile (0.0278 mol) was stirred in EtOH (p.a) (75 ml) under N₂-atm., then P₂O₅ (phosphorus anhydride) (0.0106 mol) was added portionwise, the reaction mixture was stirred for 2 hours and stood overnight. The resulting precipitate was filtered off, washed with EtOH, with DIPE and with H₂O, then dried. Yield: 2.85 g of intermediate 15 (36.7%)

b. Preparation of Intermediate 16

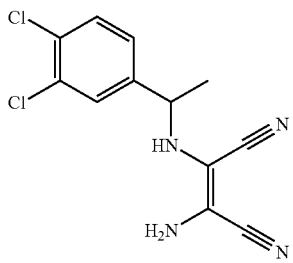

NaBH₄ (0.013 mol) was added portionwise to a solution of intermediate 15 (0.01 mol) in CH₃OH (30 ml) and THF, p.a. (40 ml), then the reaction mixture was stirred for 2 hours. The mixture was diluted with H₂O (275 ml) and extracted with CH₂Cl₂. The organic layer was separated, dried (MgSO₄), filtered and the solvent was evaporated. The residue was stirred in CH₂Cl₂/CH₃OH (99.5/0.5), then the precipitate was filtered off, washed with CH₂Cl₂, with DIPE and dried (vac., 45° C.). Yield: 0.86 g of intermediate 16.

EXAMPLE A7 a. Preparation of Intermediate 17

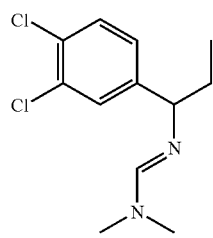

A mixture of 3,4-dichloro-α-ethylbenzenemethanamine (0.04 mol) in 1,1-dimethoxy-N,N-dimethylmethanamine (80 ml) was stirred and refluxed for 3 hours, then the solvent was evaporated and co-evaporated 2 times with toluene. Yield: intermediate 17.

b. Preparation of Intermediate 18

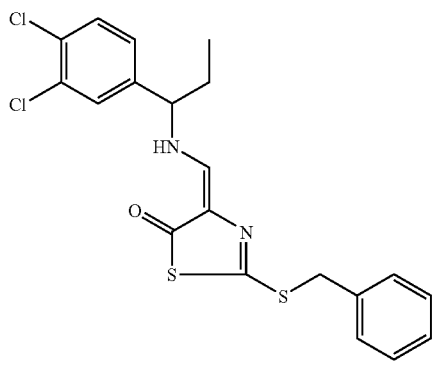

A solution of intermediate 17 (0.035 mol) and 2-[(phenylmethyl)thio]-5(4H)-thiazolone (0.035 mol) in toluene, p.a. (200 ml) was stirred at 60° C. for 2.5 hours, stirred overnight at room temperature, then stirred at 60° C. for 2 hours. The solvent was evaporated and the residue was purified by filtration over silica gel (eluent: CH$_2$Cl$_2$/Hexane 50/50). The product fractions were collected and the solvent was evaporated, then co-evaporated with CH$_3$OH. Yield: 5.9 g of intermediate 18.

EXAMPLE A8 a. Preparation of Intermediate 19

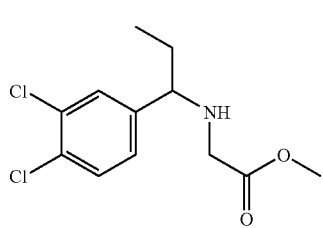

A mixture of intermediate 11 (prepared according to A4.c) (0.0054 mol), bromo-acetic acid methyl ester (0.0055 mol) and Et$_3$N (0.006 mol) in DMF (q.s.) was stirred overnight at room temperature, then poured out into water. This mixture was extracted with CH$_2$Cl$_2$. The separated organic layer was dried, filtered and the solvent evaporated. Yield: 1.3 g of intermediate 19 (R-isomer).

b. Preparation of Intermediate 20

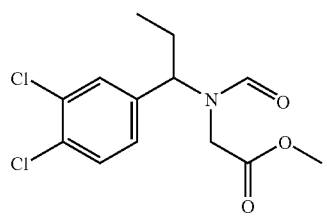

A mixture of intermediate 19 (0.0054 mol) in formic acid (3 ml) and xylene (50 ml) was stirred and refluxed for 20 hours. The reaction mixture was cooled, washed with water, dried, filtered and the solvent evaporated. Yield: 1.3 g of intermediate 20 (R-isomer).

EXAMPLE A9 a. Preparation of Intermediate 21

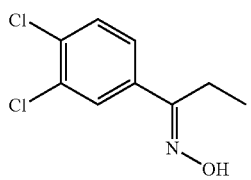

A solution of Na$_2$CO$_3$ (part of 0.52 mol) in water (150 ml) was added to a stirring mixture of 1-(3,4-dichlorophenyl)-1-propanone (0.345 mol) in ethanol p.a. (150 ml), then the remainder of Na$_2$CO$_3$ was added and hydroxylamine hydrochloride (0.345 mol) was added portionwise while stirring vigorously. The reaction mixture was heated to reflux temperature and extra water (75 ml) was added (to improve solubility of inorganic material), then the resulting mixture was stirred and refluxed for 6 hours. Extra hydroxylamine hydrochloride (2.4 g) was added and the mixture was refluxed further for 18 hours. Again extra hydroxylamine hydrochloride (3 g) was added; the reaction mixture was refluxed for 24 hours and stirred for 2 days at room temperature. The solids were filtered off, washed with ethanol/water (1/1) and dried (vacuum, stream of air) at 56° C. Yield: 71.8 g (95.4%) of intermediate 21.

b. Preparation of Intermediate 22

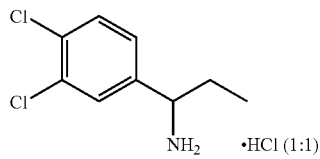

A mixture of intermediate 21 (0.3 mol) in CH$_3$OH/NH$_3$ 7N (500 ml) was hydrogenated at 14° C. with raney nickel (cat. quant.) as a catalyst in the presence of thiophene solution (6 ml). After uptake of H$_2$ (2 equiv.), the catalyst was filtered off and the filtrate was evaporated, then co-evaporated 2 times with toluene. The residue was stirred in boiling 2-propanol (250 ml) and the mixture was filtered off hot. The filtrate was allowed to reach room temperature and HCl/2-propanol (6N, 150 ml) was added slowly while stirring vigorously. The solvent was evaporated and the residue was stirred in DIPE, then filtered off, washed and dried vacuum) at 60° C. Yield: 53 g (73.4%) of intermediate 22, isolated as a hydrochloric acid salt.

c. Preparation of Intermediate 23

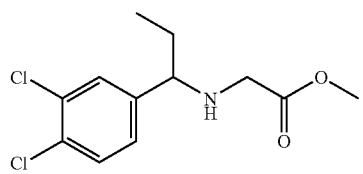

A solution of intermediate 22 (0.0748 mol) and chloro-acetic acid, methyl ester (0.08 mol) in DMF, p.a. dried on molecular sieves (150 ml) was stirred at room temperature under $N_2$ and $Et_3N$ (0.224 mol) was slowly added, then the reaction mixture was stirred for 20 hours at room temperature and extra chloro-acetic acid, methyl ester (3.3 ml) was added. The mixture was stirred for another 20 hours at room temperature and again extra chloro-acetic acid, methyl ester (2 ml) was added. The resulting mixture was stirred for 24 hours and then the solids were filtered off and washed with DMF. $Et_2O$ (800 ml) was added and the mixture was washed 3 times with water (500 ml). The organic layer was separated, dried ($MgSO_4$), filtered off and the solvent was evaporated, then co-evaporated with toluene. The residual oil (23.4 g) was filtered over silica gel (eluent: $CH_2Cl_2/CH_3OH$ 99/1). The product fractions were collected and the solvent was evaporated, finally co-evaporated with toluene. Yield: 20.6 g (99.7%) of intermediate 23.

d. Preparation of Intermediate 24

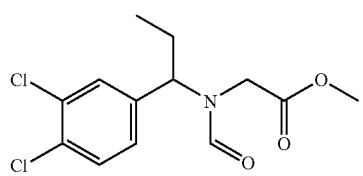

A solution of formic acid (7.5 ml) and intermediate 23 (0.0746 mol) in xylene p.a. (225 ml) (biphasic) was stirred and refluxed for 4 hours and then the reaction mixture was allowed to reach room temperature. The mixture was washed 2 times with water (2×200 ml), with a saturated aqueous $NaHCO_3$ solution (200 ml) and with a saturated NaCl solution (200 ml), then the separated organic layer was dried ($MgSO_4$) and filtered off. Finally, the solvent was evaporated. Yield: 21.3 g (93.9%) of intermediate 24.

EXAMPLE A10 a. Preparation of Intermediate 25

(R)

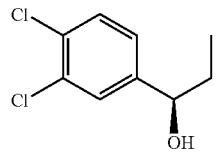

A mixture of N,N'-(1S,2S)-1,2-cyclohexanediylbis[1,1,1-trifluoro-methanesulfonamide (0.060 g) and $Ti(iPrO)_4$ (8.5 g) in toluene was degassed, placed under Ar flow, then stirred for 20 minutes at 40° C. The mixture was cooled to −78° C. and diethylzinc (q.s.) was addded dropwise. After 20 minutes, 3,4-dichloro-benzaldehyde (0.025 mol) in toluene (q.s.) was added dropwise and the reaction mixture was allowed to warm up to 0° C., then was stirred overnight at room temperature, quenched with 2 N HCl and extracted with $CH_2Cl_2$. The separated organic layer was washed, dried, filtered and the solvent evaporated. The residue was purified by column chromatography over silica gel (eluent: $CH_2Cl_2/CH_3OH$ 98/2). The product fractions were collected and the solvent was evaporated. Yield: 5 g of intermediate 25 (R).

b. Preparation of Intermediate 26

S-(−)

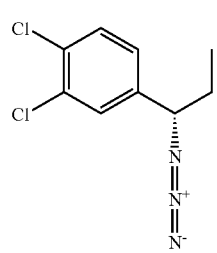

A mixture of intermediate 25 (0.127 mol) and phospho-razidic acid, diphenyl ester (0.153 mol) in toluene (q.s.) was stirred at 0° C. 2,3,4,6,7,8,9,10-octahydro-pyrimido[1,2-a]azepine (0.153 mol) was added dropwise and the reaction mixture was stirred for 1 hour at 0° C., then for 2 hours at room temperature, then for 3 hours at 50° C. The reaction mixture was cooled, washed with water, with 0.5 M HCl, with water, dried, filtered and the solvent evaporated. The residue was purified by flash column chromatography over silica gel (eluent: $CH_2Cl_2/CH_3OH$ 99.5/0.5). The product fractions were collected and the solvent was evaporated. Yield: 23.5 g of intermediate 26, S-(−).

c. Preparation of Intermediate 27

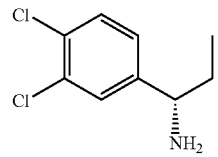

A mixture of intermediate 26 (0.122 mol) in methanol (q.s.) was hydrogenated at 50° C. with $Pt/C_5\%$ (5 g) as a catalyst. After uptake of $H_2$, the catalyst was filtered off and the filtrate was evaporated. Yield: intermediate 27.

d. Preparation of Intermediate 28

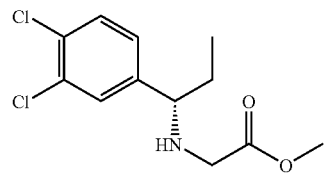

A mixture of intermediate 27 (0.050 mol), methyl bromoacetate (0.060 mol) and $Et_3N$ (15 ml) in DMF (100 ml) was stirred overnight at room temperature. More methyl bromoacetate was added, and the reaction mixture was stirred overnight at room temperature, then poured out into water.

This mixture was extracted with CH$_2$Cl$_2$. The separated organic layer was dried, filtered and the solvent evaporated. Yield: 12 g of intermediate 28.

e. Preparation of Intermediate 29

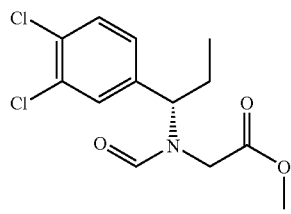

A mixture of intermediate 28 (0.05 mol) in formic acid (100 ml) and xylene (150 ml) was stirred and refluxed for 48 hours. The reaction mixture was cooled, poured out into water, then extracted with toluene. The separated organic layer was washed with water, treated with NaHCO$_3$, dried, filtered and the solvent evaporated. Yield: 13.2 g of intermediate 29.

EXAMPLE A11 a. Preparation of Intermediate 30

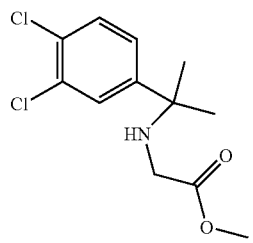

A mixture of 3,4-dichloro-α,α-dimethyl-benzenemethanamine (0.032 mol) in methyl bromoacetate (6 ml), DMF (50 ml) and Et$_3$N. (15 ml) was reacted overnight at room temperature and after partial conversion, the reaction mixture was heated to 45° C. for 6 hours. The mixture was filtered, diluted with CH$_2$Cl$_2$ and washed 5 times with water, then dried and the solvent was evaporated. Yield: intermediate 30.

b. Preparation of Intermediate 31

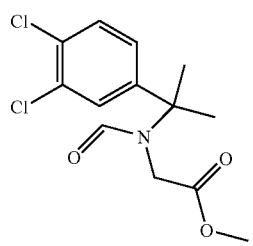

A mixture of intermediate 30 (residue) in formic acid (50 ml) and xylene (50 ml) was stirred and refluxed for 18 hours, then the reaction mixture was cooled and partitioned between water and toluene. The organic layer was separated, dried (MgSO$_4$), filtered off and the solvent was evaporated. The residue was purified by column chromatography over silica gel (eluent: CH$_2$Cl$_2$/CH$_3$OH 95/5). The product fractions were collected and the solvent was evaporated. The impure residue was purified by high-performance liquid chromatography. The pure product fractions were collected and the solvent was evaporated. Yield: 2.1 g of intermediate 31.

B. Preparation of the Final Compounds of Formula (I)

EXAMPLE B1 a. Preparation of Compound 1

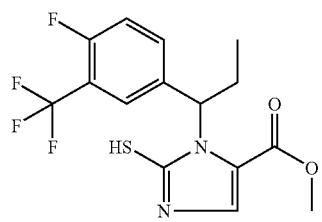

A solution of intermediate 4 (prepared according to A1.d) (0.0177 mol), formic acid methyl ester (0.05 mol) and THF (p.a., dried on molecular sieves) (30 ml) was stirred under N$_2$-flow, then NaOMe (prepared in situ; see note below) (0.0185 mol) was added and the reaction mixture was stirred at room temperature for 20 hours. The solvent was evaporated, the residue was stirred in H$_2$O (40 ml) and washed 2 times with Et$_2$O. MeOH (35 ml), then HCl (36%, p.a.) (4.2 ml) was added to the separated aqueous layer. KSCN (0.03 mol) was added and the resulting solution was stirred at 50° C. for 6 hours, then for 20 hours at room temperature, at 80° C. for 3 hours and finally stirred overnight at room temperature. The resulting precipitate was filtered off, washed with CH$_3$OH/H$_2$O (1/2) and dried (vac., 60° C.). Yield: 4.25 g of compound 1.

Note: NaOMe was generated in situ with NaH (0.74 g, 60% in mineral oil) and MeOH (0.74 ml) in THF (15 ml; p.a., dry).

b. Preparation of Compound 2

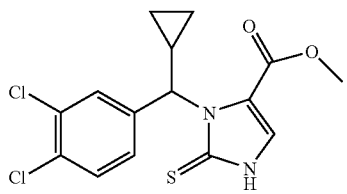

A mixture of

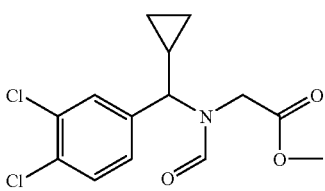

(prepared according to A1.d) (0.02 mol) and formic acid methyl ester (0.06 mol) in THF (100 ml) was stirred at room temperature, then 2-methyl-2-propanol sodium salt (0.025 mol) was added and the reaction mixture was stirred for 3 hours at room temperature. The solvent was evaporated, the residue was stirred in H$_2$O (±100 ml) for 15 minutes and washed with Et$_2$O. The aqueous layer was separated, then HCl (conc.) (0.06 mol) was added. CH$_3$OH (±100 ml) was added, then KSCN (0.03 mol) was added and the reaction mixture was stirred for 18 hours at 60° C. The mixture was stirred at room temperature for 2 hours, then stirred in hexane. The precipitate was filtered off and dried. Yield: 6A4 g of compound 2.

EXAMPLE B2

Preparation of Compound 3

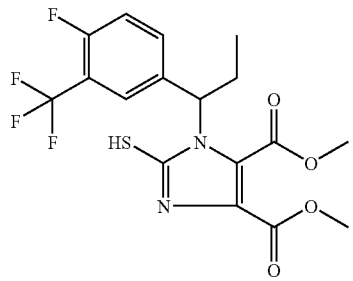

A solution of intermediate 4 (prepared according to A1.d) (0.0174-mol), ethanedioic acid dimethyl ester (0.03 mol) and THF (p.a., dried on molecular sieves) (30 ml) was stirred, then NaOMe (prepared in situ; see note below) (0.0185 mol) was added and the reaction mixture was stirred at room temperature for 18 hours. The solvent was evaporated, the residue was stirred in H₂O (50 ml) and washed with Et₂O (2 times). MeOH (35 ml), then HCl (36%, p.a.) (4.2 ml) was added to the separated aqueous layer. KSCN (0.03 mol) was added and the resulting solution was stirred at 50° C. for 18 hours. The mixture was allowed to reach room temperature, then extra H₂O was added and the mixture was extracted with CH₂Cl₂. The organic layer was separated, dried (MgSO₄), filtered and the solvent was evaporated. The residue was purified by column chromatography over silica gel (eluent: CH₂Cl₂/CH₃OH 98.5/1.5). The purest product fractions were collected and the solvent was evaporated. The residue was further purified by flash column chromatography on Flash Tubes (eluent: CH₂Cl₂/THF 95/5). The product fractions were collected and the solvent was evaporated, then the resiude was filtered off and dried. Yield: 0.0186 g of compound 3.

Note: NaOMe was generated in situ with NaH (0.74 g, 60% in mineral oil) and MeOH (0.74 ml) in THF (15 ml; p.a., dry).

b. Preparation of Compound 4

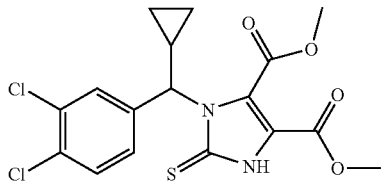

A mixture of

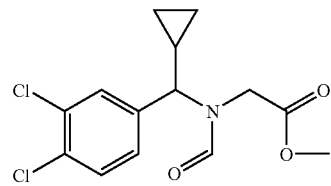

(prepared according to A1.d) (0.02 mol) and ethanedioic acid dimethyl ester (0.04 mol) in THF (100 ml) was stirred at room temperature, then 2-methyl-2-propanol sodium salt (0.025 mol) was added in one portion and the reaction mixture was stirred for 18 hours at 60° C. Extra 2-methyl-2-propanol sodium salt (0.025 mol) was added portionwise at 60° C. and the reaction mixture was stirred overnight at 60° C. Again, extra 2-methyl-2-propanol sodium salt (0.005 mol) was added at 60° C. and the mixture was stirred further at 60° C. for 3 hours. The solvent was evaporated, the residue was stirred in H₂O and washed with Et₂O. The aqueous layer was separated, then HCl (conc.) (5 ml) was added. A solid was precipitated and CH₃OH was added (until the solution was clear), then KSCN (0.03 mol) was added and the reaction mixture was stirred for 20 hours at 60° C. The organic solvent (CH₃OH) was evaporated and the aqueous concentrate was extracted with CH₂Cl₂. The organic layer was separated, dried, filtered and the solvent was evaporated. The residue was purified by filtration over silica gel (eluent: CH₂Cl₂/CH₃OH 98/2). The product fractions were collected and the solvent was evaporated. The residue was crystallised from DIPE, filtered off and dried. Yield: 2 g of compound 4.

c. Preparation of Compound 5

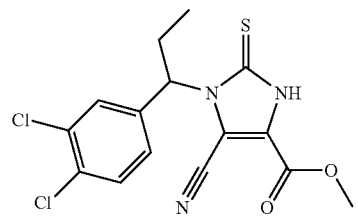

Intermediate 13 (prepared according to A4.e) (0.0136 mol) was added to a mixture of NaH (60%) (0.6 g) in THF (50 ml), then ethanedioic acid dimethyl ester (0.0152 mol) was added and the reaction mixture was stirred for 5 hours at room temperature. The mixture was poured out into H₂O and the aqueous layer was extracted with CH₂Cl₂. The organic layer was separated and acidified, then the aqueous layer was extracted with CH₂Cl₂. The organic layer was filtered and the solvent was evaporated. The residue was treated with CH₃OH (20 ml), with H₂O (20 ml) and with HCl (5 ml, 1N). A mixture of KSCN (1 g) in H₂O (10 ml) was added and the reaction mixture was stirred at 60° C. for 18 hours. The resulting precipitate was filtered off and purified by column chromatography over silica gel (eluent: CH₂Cl₂/CH₃OH 90/10). The product fractions were collected and the solvent was evaporated. Yield: 0.700 g of compound 5.

d. Preparation of Compounds 37 and 68 compound 37

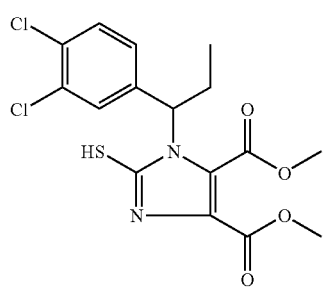

-continued compound 68

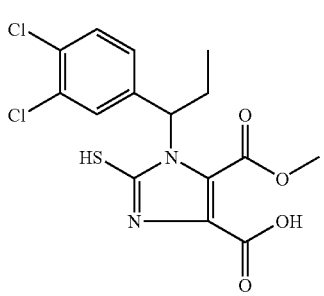

A solution of

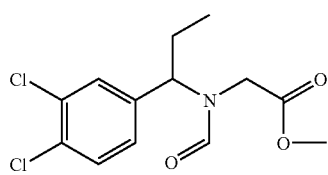

(0.0618 mol) and ethanedioic acid dimethyl ester (0.11 mol) in THF (p.a., dried on molecular sieves) (100 ml) was stirred under $N_2$-atm., then 2-methyl-2-propanol sodium salt (0.066 mol) was added and the reaction mixture was stirred at room temperature for 18 hours and another for 24 hours. Finally the mixture was stirred at 60° C. for 4 hours. Extra 2-methyl-2-propanol sodium salt (4 g) and extra ethanedioic acid dimethyl ester (6 g) were added and the reaction mixture was stirred over the weekend at room temperature. The solvent was evaporated, the residue was dissolved in $H_2O$ (250 ml) and washed 2 times with $Et_2O$. The aqueous layer was separated and $CH_3OH$ (200 ml), KSCN (10 g) and HCl (36%, p.a.) (q.s.) were added, then the mixture was stirred for 18 hours at 60° C. The solvent was partly evaporated and the concentrate was extracted with $CH_2Cl_2$. The organic layer was separated, dried ($MgSO_4$), filtered and the solvent was evaporated. The residue (5 g) was purified by filtration over silica gel (eluent: $CH_2Cl_2/CH_3OH$ 99/1). The product fractions were collected and the solvent was evaporated. The residue was triturated under Hexane, filtered off, washed, then dried (vac., 50° C.) Yield: 5.2 g of compound 37. The fractions containing a side-product were combined and the solvent was evaporated, then co-evaporated with Hexane/DIPE. The residue was stirred in $Et_2O$/Hexane and the resulting precipitate was filtered off, washed with hexane, then dried (vac., 50° C.). Yield: 0.28 g of compound 68.

EXAMPLE B3

Preparation of Compound 6

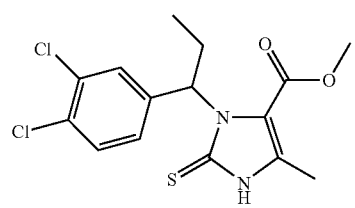

A mixture of intermediate 8 (prepared according to A3) (0.0079 mol) and KSCN (0.031 mol) in HCl (1N) (5 ml) was stirred in EtOH (50 ml) at 80° C. for 4 hours. The reaction mixture was poured out into $H_2O$ and extracted with $CH_2Cl_2$. The organic layer was separated, dried ($MgSO_4$), filtered and the solvent was evaporated. The residue was purified by reversed phase chromatography. The produce fractions were collected and the solvent was evaporated to fifty percent less of the initial volume. The residue was extracted with $CH_2Cl_2$, then the organic layer was separated, dried, filtered and the solvent was evaporated. Yield: 0.3 g of compound 6.

EXAMPLE B4

Preparation of Compounds 7 and 8

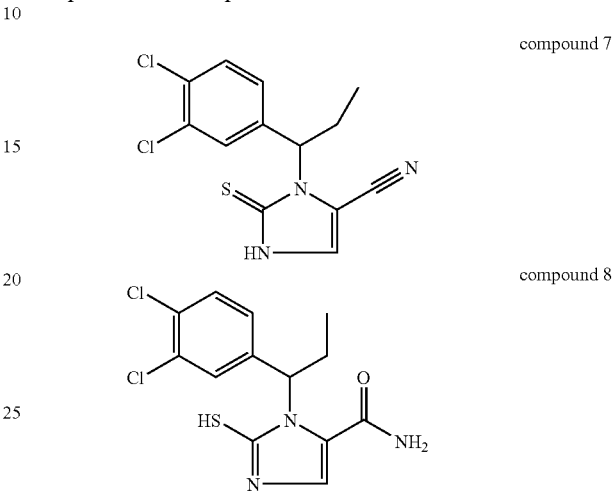

A solution of intermediate 13 (prepared according to A4.e) (0.0094 mol), formic acid methyl ester (0.027 mol) and THF (p.a., dried on molecular sieves) (15 ml) was stirred under $N_2$ flow. NaOMe (prepared in situ; see note) (0.01 mol) was added and the reaction mixture was stirred at room temperature for 20 hours. The solvent was evaporated. The residue was dissolved in $H_2O$ (20 ml) and washed with $Et_2O$ (2×2 0 ml). MeOH (15 ml) was added to the separated aqueous layer. Then HCl (36%, p.a.) (2.25 ml) was added. KSCN (1.52 g) was added and the reaction mixture was stirred at 50° C. for 5 hours, at room temperature for 16 hours and refluxed for 5 hours. Then it was allowed to cool to room temperature. The liquid layer was decanted. The oily layer was dissolved in $CH_2Cl_2$/MeOH (95:5) and washed with $H_2O$. The separated organic layer was dried ($MgSO_4$), filtered and the solvent was evaporated. The residue was purified by flash column chromatography over silica gel (eluent: $CH_2Cl_2$/MeOH gradient). The desired fractions were collected and the solvent was evaporated. Yield Fraction 1: 0.065 g of compound 7 and yield Fraction 2: 0.063 g of compound 8 Note: NaOMe was generated in situ with NaH (0.4 g, 60% in mineral oil) and MeOH (0.4 ml) in THF (10 ml; p.a., dry).

EXAMPLE B5 a. Preparation of Compound 9

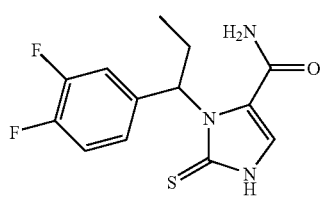

A mixture of intermediate 14 (prepared according to A5) (0.00158 mol) and acetic acid ammonium salt (0.00649 mol) was stirred in acetone (q.s.) for 2 hours at room temperature, then the solvent was evaporated. The residue was purified by reversed phase chromatography. The product fractions were collected and the aqueous layer was evaporated to fifty percent less of the initial volume. The resulting concentrate was extracted with CH$_2$Cl$_2$, then the organic layer was separated, dried (MgSO$_4$), filtered and the solvent was evaporated. Yield: 0.27 g of compound 9.

b. Preparation of Compound 10

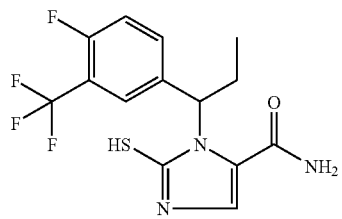

A solution of 3-[1-(4-fluoro-3-trifluoromethyl-phenyl) propyl]-2-mercapto-3H-imidazole-4-carbonyl chloride (prepared according to A5) (0.0003 mol) in THF (p.a., dried on molecular sieves) (1 ml) was added in one portion to stirring NH$_3$ (1 ml) and the reaction mixture was stirred overnight. H$_2$O was added and the mixture was extracted with CH$_2$Cl$_2$. The organic layer was separated, then evaporated. The residue was dissolved in acetone (5 ml) and treated with a SO$_2$-flow for 15 minutes. The solvent was evaporated and the residue was purified by reversed phase high-performance liquid chromatography. The product fractions were collected and the solvent was evaporated. CH$_2$Cl$_2$ (6 ml) and an aq. K$_2$CO$_3$ solution. (1 ml, 10%) were added, then the mixture was stirred for 5 minutes and filtered over an ISOLUTE HM-N cartridge. The filtrate was evaporated. Yield: 0.0289 g of compound 10.

EXAMPLE B6

Preparation of Compound 11

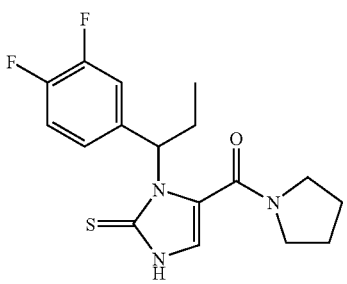

A mixture of intermediate 14 (prepared according to A5) (0.00126 mol) in pyrrolidine (0.00599 mol) was stirred in DMF (q.s.) for 4 hours at room temperature. The solvent was evaporated and the residue was stirred in acetone (50 ml), then treated with SO$_2$ for 10 minutes. The acetone was evaporated and the concentrate was purified by reversed phase chromatography. The product fractions were collected and the solvent was evaporated to fifty percent less of the initial volume. The resulting concentrate was extracted with CH$_2$Cl$_2$, then the organic layer was separated, dried (MgSO$_4$), filtered and the solvent was evaporated. Yield: 0.180 g of compound 11.

EXAMPLE B7 a. Preparation of Compound 12

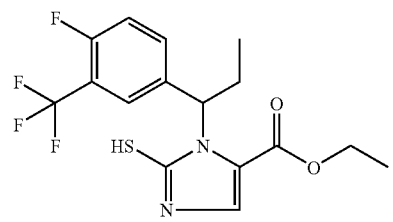

A solution of 3-[1-(4-fluoro-3-trifluoromethyl-phenyl) propyl]-2-mercapto-3H-imidazole-4-carbonyl chloride (prepared according to A5) (0.0003 mol) in THF (p.a., dried on molecular sieves) (1 ml) was added in one portion to stirring EtOH, p.a. (1 ml) and the reaction mixture was stirred overnight. The solvent was evaporated and the residue was stirred in CH$_2$Cl$_2$/H$_2$O. The organic layer was separated, then evaporated. The residue was dissolved in acetone (5 ml) and treated with a SO$_2$-flow for 15 minutes. The solvent was evaporated and the residue was purified by reversed phase high-performance liquid chromatography. The product fractions were collected and the solvent was evaporated. CH$_2$Cl$_2$ (6 ml) and an aq. K$_2$CO$_3$ solution. (1 ml, 10%) were added, then the mixture was stirred for 5 minutes and filtered over an ISOLUTE HM-N cartridge. The filtrate was evaporated. Yield: 0.0369 g of compound 12.

b. Preparation of Compound 61

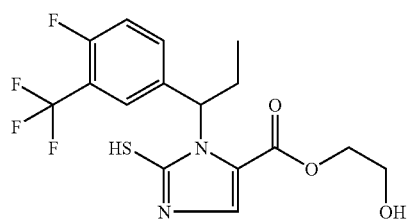

A solution of 3-[1-(4-fluoro-3-trifluoromethyl-phenyl) propyl]-2-mercapto-3H-imidazole-4-carbonyl chloride (prepared according to A5) (0.0003 mol) in THF (p.a., dried on molecular sieves) (1 ml) was added in one portion to stirring 1,2-ethanediol (1 ml) and the reaction mixture was stirred overnight. H$_2$O was added and the mixture was extracted with CH$_2$Cl$_2$. The organic layer was separated, then evaporated. The residue was dissolved in acetone (5 ml) and treated with a SO$_2$-flow for 15 minutes. The solvent was evaporated and the residue was purified by reversed phase high-performance liquid chromatography. The product fractions were collected and the solvent was evaporated. CH$_2$Cl$_2$ (6 ml) and an aq. K$_2$CO$_3$ solution. (1 ml, 10%) were added, then the mixture was stirred for 5 minutes and filtered over an ISOLUTE HM-N cartridge. The filtrate was evaporated. Yield: 0.0215 g of compound 61.

EXAMPLE B8

Preparation of Compound 13

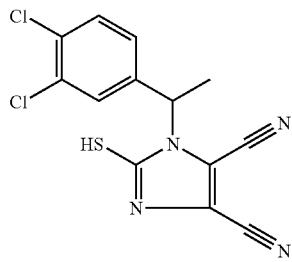

A mixture of intermediate 16 (prepared according to A6.b) (0.000356 mol) in CH$_2$Cl$_2$ p.a. (2 ml) was stirred under N$_2$-atm., carbonothioic dichloride (0.00045 mol), then N,N-diethylethanamine (0.125 ml) was added and the reaction mixture was stirred for 1.5 hour at room temperature. The mixture was quenched with H$_2$O and extracted with CH$_2$Cl$_2$. The organic layer was separated, filtered and the solvent was evaporated. The residue was purified by reversed phase high-performance liquid chromatography. The product fractions were collected and the organic solvent was evaporated. The aqueous concentrate was extracted with CH$_2$Cl$_2$, then the organic layer was separated, filtered and the solvent was evaporated. Yield: 0.0072 g of compound 13.

EXAMPLE B9

Preparation of Compound 14

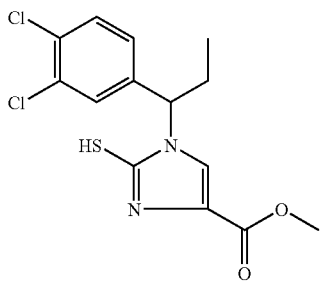

NaOMe in MeOH (0.4 ml) was added to a solution of intermediate 18 (prepared according A7.b) (0.0001 mol) in methanol, p.a. (1.5 ml) and the reaction mixture was stirred under N$_2$-flow for 18 hours at room temperature. The mixture was quenched with acidic water and extracted with CH$_2$Cl$_2$. The organic layer was separated, dried (MgSO$_4$), filtered and the solvent was evaporated. The residue was purified by filtration over a Flash Tube (eluent: CH$_2$Cl$_2$), then the product fractions were collected, taken up in CH$_2$Cl$_2$/CH$_3$OH and the solvent was evaporated. Yield: 0.0136 g of compound 14.

EXAMPLE B10

Preparation of Compounds 16 and 17

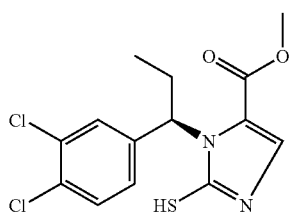
(R) compound 16

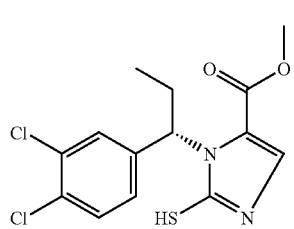
(S) compound 17

Compound 15

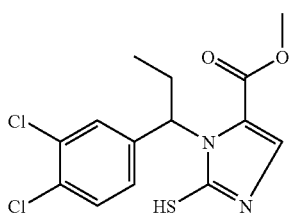

(prepared according to B1.a or B1.b) (0.001 mol) was separated and purified by chiral column chromatography over a ProChrom D.A.C. column (I.D. 5 cm; 500 g AD chiral phase; Injection: 360 mg in 1×35 ml of ethanol; eluent: Ethanol (isocratic)). Two product fraction groups were collected and their solvent was evaporated. Yield: 0.156 g of compound 16 ((A)=(+)-(R)) and 0.153 g of compound 17 ((B)=(−)-(S)).

EXAMPLE B11

Preparation of Compound 16

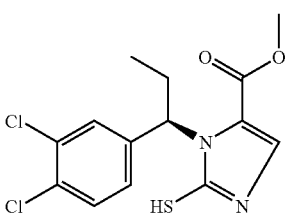
(R)

NaH, CH$_3$OH (0.005 mol) was added to a mixture of intermediate 20 (prepared according to A8.b) (0.00427 mol) and formic acid methyl ester (1 g) in THF (20 ml). The mixture was stirred for 24 hours at room temperature. The mixture was concentrated by evaporation and the concentrate was diluted with water and washed with EtO$_2$. A mixture of HCl (5 ml) and KCN (1 g) in methanol (25 ml) was added to the aqueous layer and the resulting reaction mixture was stirred and refluxed overnight. The gummy solid was separated from the water layer and taken up into CH$_2$Cl$_2$. The organic solution was dried, filtered and the solvent evaporated. The residue was purified by column chromatography over silica gel. The product fractions were collected and the solvent was evaporated. Yield: 0.50 g of compound 16 (R-isomer).

EXAMPLE B12

Preparation of Compound 18

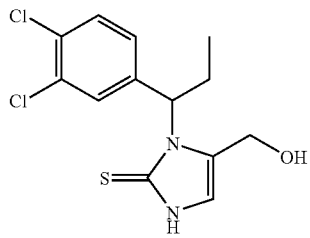

A mixture of compound 15

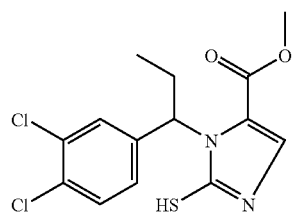

(prepared according to B1.a or B1.b) (0.00032 mol) in LiBEt$_3$, 1 M (superhydride) (2.5 ml) and THF (2 ml) was stirred for 2 hours at room temperature. Methanol was added, and then evaporated again. The residue was purified by reversed-phase HPLC (gradient elution). The product fractions were collected and the solvent was evaporated. Yield: 0.0142 g of compound 18.

EXAMPLE B13

Preparation of Compounds 19 and 20 compound 19

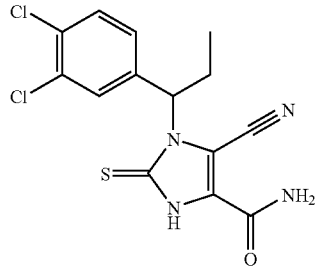

compound 20

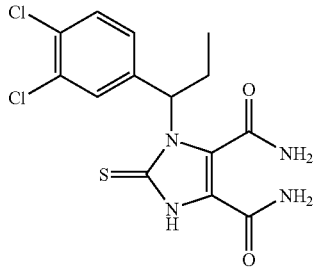

Compound 5 (prepared according to B2.c) (0.00054 mol) was reacted with NH$_4$OH (q.s.) in a closed vessel for 18 hours at 100° C., then the solvent was evaporated and the residue was purified, by reversed phase high-performance liquid chromatography. Two product fraction groups were collected and each solvent was evaporated. Yield Fraction group 1: 0.075 g of compound 19. Yield Fraction group 2: 0.080 g of compound 20.

EXAMPLE B14 a. Preparation of Compound 22

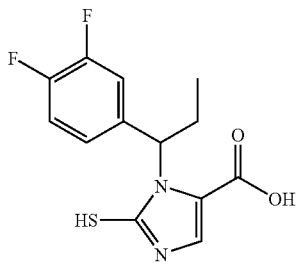

A mixture of compound 21

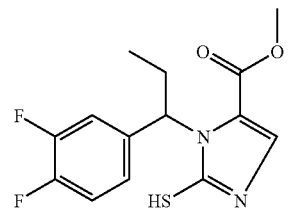

(prepared according to B1.a or B1.b) (0.0128 mol) in NaOH (25%) (50 ml) was stirred for 36 hours, then the solution was treated with HCl (conc.) at 0° C. The resulting precipitate was filtered off and dried (vac.). Yield: 3.2 g of compound 22.

b. Preparation of Compound 23

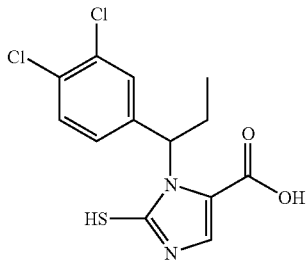

A solution of compound 15

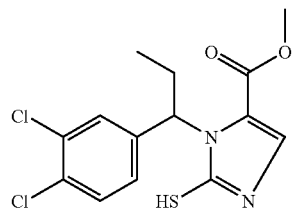

(prepared according to B1.a or B1.b) (0.004 mol) in NaOH (1N) (7.5 ml), CH₃OH, p.a. (10 ml) and THF, p.a. (20 ml), was stirred at room temperature for 20 hours, then stirred for 5 days at 75° C. Extra NaOH (1N) (7.5 ml) was added and the reaction mixture was stirred for 1 hour at 75° C., then the mixture was allowed to reach room temperature. H₂O (45 ml), then Et₂O (50 ml) was added and the reaction mixture was stirred for 30 minutes. The aqueous layer was separated, washed with EtOAc/Hexane (2×50 ml, 1/1) and acidified with HCl (1N) to pH 3. The mixture was extracted with CH₂Cl₂/CH₃OH (95/5), then the organic layer was separated, dried (MgSO₄), filtered and the solvent was evaporated. The residue was dissolved in Et₂O/Hexane/CH₂Cl₂ (1/1/1) and concentrated at 60° C. (without vacuum) until crystallisation started, then the mixture stood for 30 minutes. The precipitate was filtered off, washed with Hexane/Et₂O (3/1) and dried (vac., 50° C.), then dried with vacuum pump for 5 hours. Yield: 0.55 g of compound 23 (41.5%)

EXAMPLE B15

Preparation of Compound 69

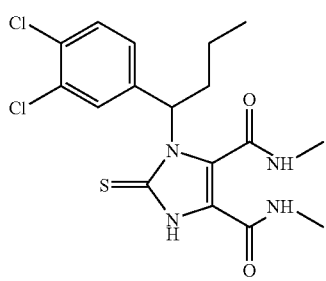

A mixture of compound 46

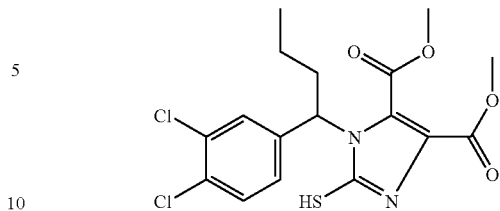

(prepared according to B2.a/B2.b) (0.00072 mol) in CH₃NH₂ (aqueous solution) (5 ml) was stirred for 18 hours at 100° C. in a closed vessel, then the reaction mixture was cooled and the solvent was evaporated under N₂-flow. The residue was purified by reversed phase high-performance liquid chromatography. The product fractions were collected and the solvent was evaporated to fifty percent less of the initial volume. The concentrate was extracted with CH₂Cl₂, the organic layer was separated, dried and the solvent was evaporated. Yield: 0.180 g of compound 69.

EXAMPLE B16

Preparation of Compound 77

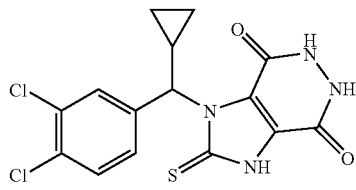

A mixture of compound 4 (0.0005 mol) in hydrazine monohydrate (1 ml) and H₂O (4 ml) was stirred in a closed vessel for 20 hours at 100° C. The solvent was evaporated and then the resulting residue was used. Yield: 0.108 g of compound 77.

EXAMPLE B17

Preparation of Compound 78

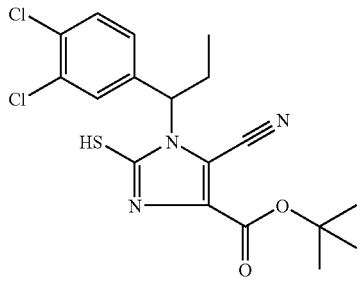

A solution of intermediate 13 (0.0158 mol) in THF p.a. dried on molecular sieves (60 ml) was stirred under N₂ and then ethanedioic acid, bis(1,1-dimethylethyl) ester (0.0238 mol) was added followed by 2-methyl-2-propanol sodium salt (0.019 mol). The reaction mixture was stirred for 4 hours at room temperature and extra 2-methyl-2-propanol sodium salt (0.4 g) was added. The mixture was stirred for 2 hours at room temperature and the solvent was evaporated. The residue was dissolved in CH$_3$OH (40 ml) and a solution of thiocyanic acid, potassium salt (0.0474 mol) in H$_2$O (20 ml) was added, then HCl 36% (2 ml) was added and the reaction mixture was stirred for 18 hours at room temperature. The mixture was further stirred at 50° C. for 24 hours, poured out into ice-water (150 ml) and extracted with CH$_2$Cl$_2$. The organic layer was separated, dried (MgSO$_4$), filtered off and the solvent was evaporated. The residue was purified by column chromatography over silica gel (eluent: CH$_2$Cl$_2$/CH$_3$OH 99.5/0.5). The product fractions were collected and the solvent was evaporated. The residue was purified by reversed phase high-performance liquid chromatography (Standard gradient). The product fractions were collected and the organic solvent was evaporated. Precipitation occurred, so the aqueous concentrate was filtered. The filtrate was extracted with CH$_2$Cl$_2$, dried (MgSO$_4$), filtered off and the solvent was evaporated. The residue was stirred in DIPE, then the resulting solids were filtered-off, washed and dried (vac.) at 50° C. Yield: 0.28 g of compound 78, melting point 172.7-175.2° C.

EXAMPLE B18

Preparation of Compound 79

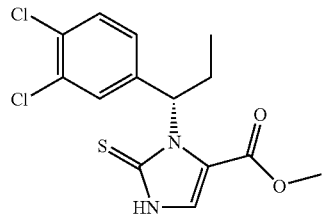
S-(-)

2-methyl-2-propanol potassium salt (0.039 mol) was added portionwise to a mixture of intermediate 29 (0.0263 mol) and formic acid, methyl ester (10 ml) in THF (150 ml), stirred at 0° C. The mixture was stirred for 30 minutes at 0° C. Thiocyanic acid, potassium salt (3 g) was added. HCl concentrated was added until the pH of the reaction mixture reached pH=1. The reaction mixture was stirred and refluxed for 48 hours, then cooled, diluted with water, and extracted with CH$_2$Cl$_2$. The separated organic layer was washed with water, dried, filtered and the solvent evaporated. The residue was purified by column chromatography over silica gel (eluent: CH$_2$Cl$_2$/CH$_3$OH 98/2). The product fractions were collected and the solvent was evaporated. Yield: 6.4 g of compound 79 (70%) (S(-)-isomer) optical rotation: [α]$_{20}^D$=-251.6° (c=0.26 CHCl$_3$).

EXAMPLE B19

Preparation of Compound 80

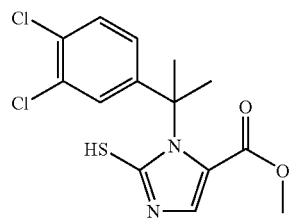

2-methyl-2-propanol sodium salt (2.5 g) was added portionwise to a mixture of intermediate 31 (0.0066 mol) in formic acid, methyl ester (5 ml) and THF (q.s.) at 0° C. and the reaction mixture was left to stand overnight at room temperature, then the mixture was diluted with ether and water. The aqueous layer was treated with thiocyanic acid, potassium salt (q.s.), HCl (q.s.) and with CH$_3$OH (q.s.) and the resulting mixture was heated for 20 hours, cooled and the solvent was evaporated. The residue was purified by reversed phase high-performance liquid chromatography. The pure fractions were collected and the solvent was evaporated. Yield compound 80.

EXAMPLE B20

Preparation of Compound 81

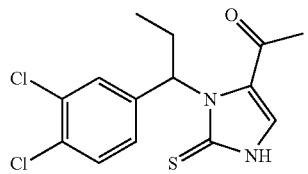

A mixture of compound 106 (prepared according to B6) (0.0008 mol) in THF (10 ml) was stirred at 0-5° C. on an ice bath and chloromethyl-magnesium 20% in THF (0.002 mol) was added dropwise, then the reaction mixture was stirred for 1 hour and extra chloromethyl-magnesium 20% in THF (0.0044 mol) was added dropwise. The mixture was stirred for 1 hour and again extra chloromethyl-magnesium 20% in THF (0.002 mol) was added dropwise, then the reaction mixture was stirred for 1 hour and 1N HCl (10 ml) was added dropwise under cooling with ice. Water was added and the mixture was extracted with CH$_2$Cl$_2$. The organic layer was separated, dried (MgSO$_4$), filtered off and the solvent was evaporated. The residue was dissolved in 2-propanone (p.a.) and a stream of SO$_2$ was passed through the solution for 20 minutes. The solvent was evaporated and the residue was purified by Flash column chromatography (eluent: EtOAc). The product fractions were collected and dissolved in CH$_2$Cl$_2$/CH$_3$OH (90/10), then the mixture was filtered and the filtrate's solvent was evaporated Yield: 0.060 g of compound 81.

EXAMPLE B21

Preparation of Compound 82

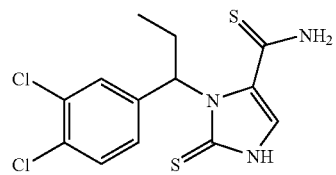

A mixture of compound-7 (0.0024 mol) and N-ethyl-N-(1-methylethyl)-2-propanamine (0.005 mol) in pyridine (25 ml) was stirred at 80° C. on an oil bath and hydrogen sulfide (gas) was passed through the solution for 90 minutes, then N$_2$ was passed through for 2 hours in order to remove the hydrogen sulfide. The solvent was evaporated and the residue was dissolved in $CH_2Cl_2$. The solution was washed with $H_2O$ and with 1N HCl. The organic layer was separated, dried ($MgSO_4$), filtered off and the solvent was evaporated. The residue was purified over silica gel (eluent: $CH_2Cl_2/CH_3OH$ 95/5). The product fractions were collected and the solvent was evaporated. The residue was stirred in DIPE, then the resulting precipitate was filtered off and dried. Yield: 0.340 g of compound 82.

EXAMPLE B22

Preparation of Compound 83

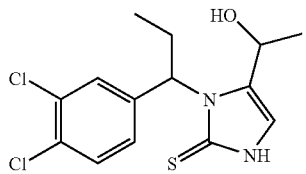

A mixture of compound 81 (0.0003 mol) in $CH_3OH$ (3 ml) was stirred at room temperature and sodium hydroborate (0.0003 mol) was added, then the reaction mixture was stirred overnight at room temperature. The resulting mixture was acidified with 1N HCl and the solvent was evaporated. The residue was dissolved in $CH_2Cl_2$ and washed with $H_2O$. The organic layer was separated, dried ($MgSO_4$), filtered off and the solvent was evaporated. The residue was purified by reversed phase ($NaHCO_3$) high-performance liquid chromatography (standard gradient). The product fractions were collected and the solvent was evaporated. Yield: compound 83.

EXAMPLE B23

Preparation of Compound 84

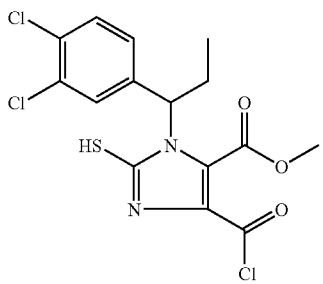

A mixture of compound 68

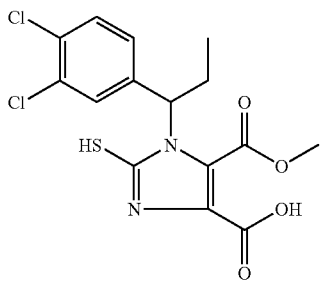

(0.000257 mol) in $SOCl_2$ (5 ml) was stirred overnight at room temperature, then the solvent was evaporated and co-evaporated with toluene (p.a.). The resulting residue was used as such in the next reaction step. Yield: compound 84.

b) Preparation of Compound 85

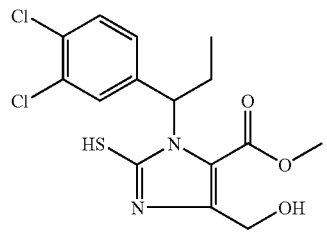

A solution of compound 84 (0.000257 mol) in THF, p.a. dried on molecular sieves (10 ml) was stirred under $N_2$ at room temperature, then sodium hydroborate (0.00077 mol) was added portionwise and the reaction mixture was stirred for 1 hour at room temperature. Water (15 ml) was added and then HCl (1N) was added (foaming) until pH: 2. The mixture was extracted with $CH_2Cl_2$ and the organic layer was separated, then dried ($MgSO_4$) and filtered. The solvent was evaporated and the residue was purified by reversed phase high-performance liquid chromatography. The product fractions were collected and the organic solvent was evaporated. The aqueous concentrate was extracted with $CH_2Cl_2$, then the organic layer was separated, dried ($MgSO_4$), filtered off and the solvent was evaporated. Yield: 0.028 g of compound 85.

EXAMPLE B24

Preparation of Compound 86

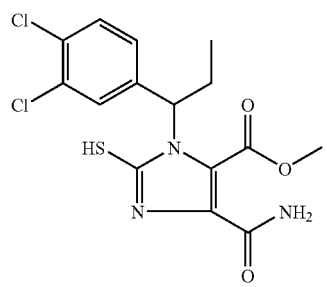

Compound 84 (0.000196 mol) was dissolved in THF, p.a. dried on molecular sieves (1 ml) under $N_2$ and the solution was added to stirring aqueous $NH_3$ solution (1 ml), then the reaction mixture was stirred for 1 hour and water (5 ml) was added. $CH_2Cl_2/CH_3OH$ (95/5, 5 ml) was added, then some crushed ice was added and concentrated HCl was added dropwise until a clear biphasic solution was obtained. The organic layer was evaporated and the residue was stirred in 2-propanone (5 ml, p.a.). The mixture was treated with $SO_2$ (gas) for 10 minutes and the solvent was evaporated. The residue was purified by reversed phase high-performance liquid chromatography. The product fractions were collected and the organic solvent was evaporated. The aqueous concentrate was extracted with $CH_2Cl_2$ and the organic layer was separated, finally the solvent was evaporated. Yield: 0.025 g of compound 86.

EXAMPLE B25

Preparation of Compound 87

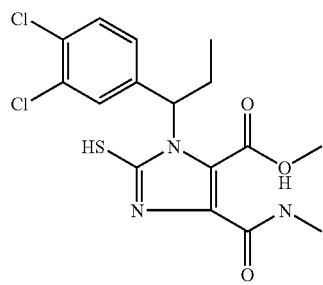

Compound 84 (0.000196 mol) was dissolved in THF, p.a. dried on molecular sieves (1 ml) under $N_2$ and the solution was added to stirring methylamine 40% (1 ml), then the reaction mixture was stirred for 1 hour and ice-water (5 ml) was added. $CH_2Cl_2/CH_3OH$ (95/5) (5 ml) was added and then concentrated HCl was added dropwise until a clear biphasic solution was obtained. The separated organic layer was evaporated and the residue was stirred in 2-propanone (5 ml). The mixture was treated with $SO_2$ (gas) for 10 minutes and the solvent was evaporated. The residue was purified by reversed phase high-performance liquid chromatography. The product fractions were combined and the organic solvent was evaporated. The aqueous concentrate was extracted with $CH_2Cl_2$ and the separated organic layer was evaporated. Yield: 0.0122 g of compound 87.

EXAMPLE B26

Preparation of Compound 88

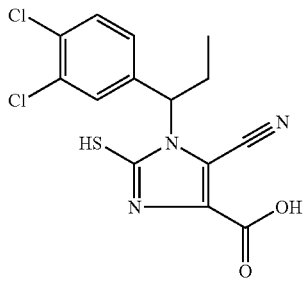

Trifluoroacetic acid (2 ml) was added to a stirring solution of compound 78 (0.0015 mol) in $CH_2Cl_2$ p.a. (25 ml), then the reaction mixture was stirred for 18 hours at room temperature (precipitation) and left to stand for 24 hours. The resulting precipitate was filtered off, washed with a small amount of $CH_2Cl_2$ and a lot of DIPE and finally dried (vacuum) at 50° C. Yield: 0.45 g of compound 88.

EXAMPLE B27

Preparation of Compound 89

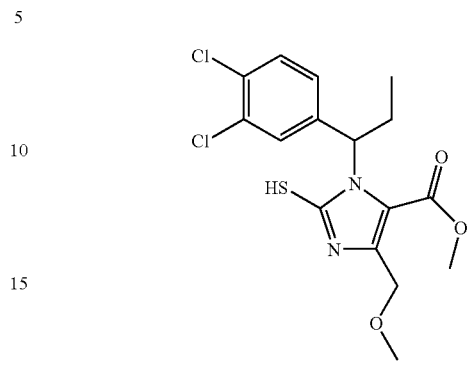

Intermediate 24 (0.003 mol) was added dropwise to a cold (−78° C.) solution of N-(1-methylethyl)-2-propanamine lithium salt (0.0036 mol) in THF (5 ml), after 30 minutes Methoxy-acetyl chloride (0.006 mol) was added to the reaction mixture and stirred for 1 hour at room temperature. The mixture was quenched with an aqueous $NH_4Cl$ solution and extracted with EtOAc. The organic layer was separated, dried ($MgSO_4$), filtered off and the solvent was evaporated. The residue was taken up in methanol (50 ml), thiocyanic acid, potassium salt (1 g) and concentrated HCl (1 ml) and the resulting mixture was heated for 18 hours at 70° C. The solvent was evaporated and the residue was extracted with $CH_2Cl_2$, then the separated organic layer was dried and the solvent was evaporated. The residue was purified by reversed phase high-performance liquid chromatography; the product fractions were collected and the solvent was evaporated. Yield: 0.250 g of compound 89.

EXAMPLE B28

Preparation of Compounds 90, 91 and 92

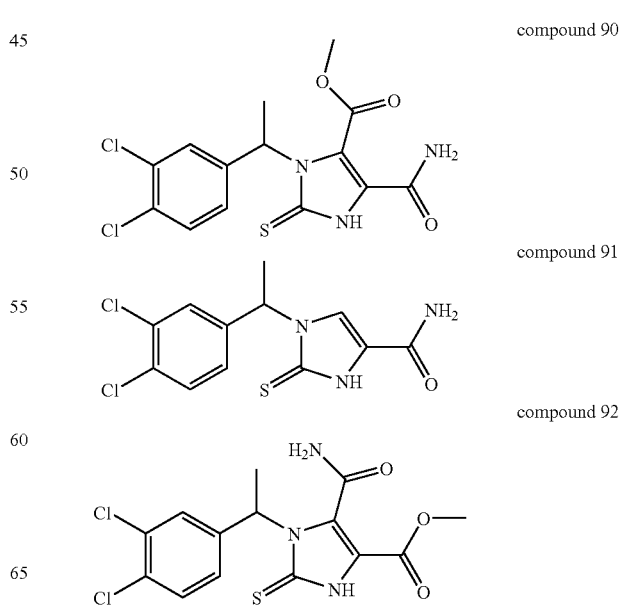

A mixture of compound 55

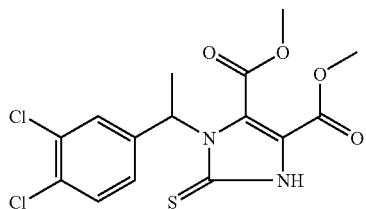

(0.0015 mol) (prepared according to B2.a/B2.b) in $NH_3/H_2O$ (12 ml) was stirred in a closed vessel at 100° C. for 18 hours and then the solvent was evaporated. The residue was stirred again in extra $NH_3/H_2O$ (12 ml) in a closed vessel at 110° C. for 18 hours. The residue (0.6 g) was purified by reversed phase high-performance liquid chromatography. The product fractions were collected and the solvent was evaporated. Yield compound 92, compound 91 and compound 90.

Table 1, 2 and 3 list the compounds of formula (I) which were prepared according to one of the above examples (Ex.No.).

In the right column headed by "Physical data", the mass value of the compounds together with the retention time is indicated. Said data were generated as described below:

The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode. Reversed phase HPLC was carried out on a Xterra MS C18 column (3.5 μn, 4.6×100 mm) (12 minutes column) with a flow rate of 1.6 ml/minutes. Three mobile phases (mobile phase A: 95% 25 mM ammoniumac-etate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minute. An injection volume of 10 μL was used.

Mass spectra were acquired by scanning from 100 to 1000 in 1 s using a dwell time of 0.1 s. The capillary needle voltage was 3 kV and the source temperature was maintained at 140° C. Nitrogen was used as the nebulizer gas. Cone voltage was 10 V for positive ionzation mode and 20 V for negative ionization mode. Data acquisition was performed with a Waters-Micromass MassLynx-Openlynx data system.

TABLE 1

| Co. no. | Ex. no. | R₁ | R₂ₐ | R₂ᵦ | R₂꜀ | R₃ | R₄ | Physical data [M⁺]* | retention time (minutes) | other |
|---|---|---|---|---|---|---|---|---|---|---|
| 24 | B1a/B1b | n-propyl | Cl | H | H | C(=O)OCH₃ | H | | | |
| 25 | B1a/B1b | n-propyl | H | Cl | H | C(=O)OCH₃ | H | | | |
| 26 | B1a/B1b | methyl | Cl | H | H | C(=O)OCH₃ | H | | | |
| 27 | B1a/B1b | methyl | CH₃ | CH₃ | H | C(=O)OCH₃ | H | | | |
| 28 | B1a/B1b | H | H | OCH₃ | H | C(=O)OCH₃ | H | | | |

TABLE 1-continued
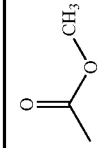
| Co. no. | Ex. no. | R1 | R2a | R2b | R2c | R3 | R4 | [M+]* | retention time (minutes) | other |
|---|---|---|---|---|---|---|---|---|---|---|
| 29 | B1a/B1b | H | Cl | H | H | | H | | | |
| 31 | B1a/B1b | methyl | H | Cl | H | | H | | | |
| 32 | B1a/B1b | methyl | Cl | Cl | H | | H | 330 | 3.76 | |
| 33 | B7 | ethyl | Cl | Cl | H | ![](isopropyl acetate) | H | 373 | 9.67** | |
| 34 | B6 | ethyl | Cl | Cl | H | | H | 344 | 3.48 | |
| 18 | B12 | ethyl | Cl | Cl | H | —CH₂OH | H | | | |

TABLE 1-continued

| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 23 | B14b | ethyl | Cl | Cl | H | COOH | H | | | |
| 35 | B1a/B1b | n-propyl | Cl | Cl | H | COOCH₃ | H | 358 | 4.26 | |
| 21 | B1a/B1b | ethyl | F | F | H | COOCH₃ | H | 313 | 8.14** | |
| 16 | B1a/B1b | ethyl | Cl | Cl | H | COOCH₃ | H | 344 | 9.10 | +229.9[e1] |
| 17 | B10 | ethyl | Cl | Cl | H | COOCH₃ | H | 344 | 9.10 | −211.7[e2] |
| 15 | B1a/B1b | ethyl | Cl | Cl | H | COOCH₃ | H | | | mp. 166° C. |

TABLE 1-continued
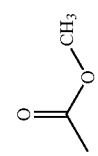
| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 76 | B1a/B1b | ethyl | Br | Br | H | -o-ch3) | H | | | |
| 22 | B14a | ethyl | F | F | H | -oh) | H | 298 | 4.55 | |
| 36 | B6 | ethyl | F | F | H | -nh-ch3) | H | 311 | 6.99 | |
| 6 | B3 | ethyl | Cl | Cl | H | -o-ch3) | CH₃ | 358 | 9.27** | |
| 37 | B2a/B2d | ethyl | Cl | Cl | H | -o-ch3) | -o-ch3) | 403 | 4.55 | |

TABLE 1-continued

| Co. no. | Ex. no. | $R_1$ | $R_{2a}$ | $R_{2b}$ | $R_{2c}$ | $R_3$ | $R_4$ | [M+]* | retention time (minutes) | other |
|---|---|---|---|---|---|---|---|---|---|---|
| 74 | B14a | ethyl | Br | Br | H | –C(O)–CH₂–OH | H | 419 | 6.26 | |
| 7 | B4 | ethyl | Cl | Cl | H | –C≡N | H | 312 | 5.71 | |
| 38 | B6 | ethyl | Cl | Cl | H | –C(O)–N(H)(CH₃) | CH₃ | 357 | 7.76 | |
| 75 | B3 | ethyl | Cl | Cl | H | –C(O)–O–CH₂CH₃ | CH₃ | | | |
| 8 | B4 | ethyl | Cl | Cl | H | –C(O)–NH₂ | H | 330 | 4.94 | |
| 39 | B2a/B2b | ethyl | F | F | H | –C(O)–O–CH₃ | –C(O)–O–CH₃ | 370 | 4.96 | |

TABLE 1-continued
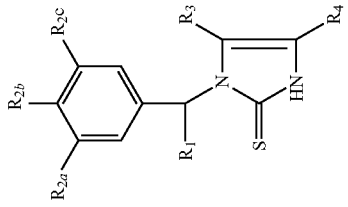
| Co. no. | Ex. no. | $R_1$ | $R_{2a}$ | $R_{2b}$ | $R_{2c}$ | $R_3$ | $R_4$ | Physical data [M+]* | retention time (minutes) | other |
|---|---|---|---|---|---|---|---|---|---|---|
| 40 | B14a | ethyl | Cl | Cl | H | –C(O)OH | –C(O)OH | 374 | 4.4 | |
| 1 | B1a/B1b | ethyl | CF$_3$ | F | H | –C(O)OCH$_3$ | H | 363 | 5.7 | |
| 3 | B2a/B2b | ethyl | CF$_3$ | F | H | –C(O)OCH$_3$ | –C(O)OCH$_3$ | 421 | 5.35 | |
| 9 | B5a | ethyl | F | F | H | –C(O)NH$_2$ | H | 297 | 4.9 | |
| 66 | B7a | ethyl | F | F | H | –C(O)OCH$_2$CH$_3$ | H | 326 | 4.95 | |

TABLE 1-continued

| Co. no. | Ex. no. | $R_1$ | $R_{2a}$ | $R_{2b}$ | $R_{2c}$ | $R_3$ | $R_4$ | [M+]* | retention time (minutes) | other |
|---|---|---|---|---|---|---|---|---|---|---|
| 30 | B6 | ethyl | F | F | H | ![piperidine acetyl] | H | | | |
| 41 | B6 | ethyl | F | F | H | ![morpholine acetyl] | H | 367 | 4.8 | |
| 42 | B6 | ethyl | F | F | H | ![piperidine acetyl] | H | 365 | 5.44 | |
| 43 | B1a/B1b | ethyl | F | CF$_3$ | H | ![methyl acetate] | H | 363 | 5.76 | |

TABLE 1-continued
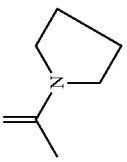
| Co. no. | Ex. no. | R₁ | R₂ₐ | R₂ᵦ | R₂c | R₃ | R₄ | [M+]* | retention time (minutes) | other |
|---|---|---|---|---|---|---|---|---|---|---|
| 11 | B6 | ethyl | F | F | H | (1-acetylpyrrolidine) | H | 351 | 5.02 | |
| 44 | B6 | ethyl | F | F | H | -C(=O)NH-(CH₂)₃-CH₃ | H | 353 | 5.59 | |
| 45 | B6 | ethyl | F | F | H | -C(=O)NH-CH₂-CH(CH₃)-CH₃ | H | 353 | 5.57 | |
| 46 | B2a/B2b | n-propyl | Cl | Cl | H | -C(=O)-O-CH₃ | -C(=O)-O-CH₃ | 384 | 4.77 | |
| 47 | B2a/B2b | H | Cl | Cl | H | -C(=O)-O-CH₃ | -C(=O)-O-CH₃ | 375 | 5.12 | |

TABLE 1-continued
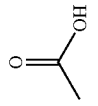
| Co. no. | Ex. no. | $R_1$ | $R_{2a}$ | $R_{2b}$ | $R_{2c}$ | $R_3$ | $R_4$ | Physical data [M+]* | retention time (minutes) | other |
|---|---|---|---|---|---|---|---|---|---|---|
| 67 | B14a | ethyl | $CF_3$ | F | H | 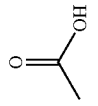 | H | 349 | 3.63 | |
| 14 | B9 | ethyl | Cl | Cl | H | H | 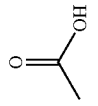 | 345 | 5.73 | |
| 5 | B2c | ethyl | Cl | Cl | H | —C≡N | 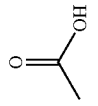 | 370 | 5.05 | |
| 48 | B2a/B2b | ethyl | F | $CF_3$ | H | 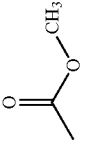 | 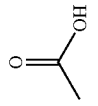 | 421 | 5.52 | |
| 12 | B7 | ethyl | $CF_3$ | F | H | 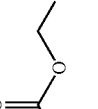 | H | 378 | 5.79 | |

TABLE 1-continued
| Co. no. | Ex. no. | R$_1$ | R$_{2a}$ | R$_{2b}$ | R$_{2c}$ | R$_3$ | R$_4$ | [M$^+$]* | retention time (minutes) | other |
|---|---|---|---|---|---|---|---|---|---|---|
| 61 | B7b | ethyl | CF$_3$ | F | H | 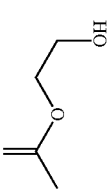 | H | 393 | 5.13 | |
| 49 | B6 | ethyl | CF$_3$ | F | H | 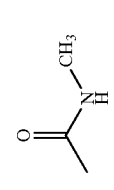 | H | 362 | 4.92 | |
| 10 | B5b | ethyl | CF$_3$ | F | H | 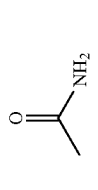 | H | 348 | 4.66 | |
| 62 | B7b | ethyl | CF$_3$ | F | H | 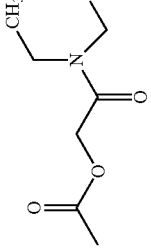 | H | 462 | 5.68 | |

TABLE 1-continued

| Co. no. | Ex. no. | $R_1$ | $R_{2a}$ | $R_{2b}$ | $R_{2c}$ | $R_3$ | $R_4$ | [M+]* | retention time (minutes) | other |
|---|---|---|---|---|---|---|---|---|---|---|
| 19 | B13 | ethyl | Cl | Cl | H | —C≡N | C(=O)NH₂ | 355 | 4.29 | |
| 20 | B13 | ethyl | Cl | Cl | H | C(=O)NH₂ | C(=O)NH₂ | 373 | 4.45 | |
| 71 | B14a | ethyl | Cl | Cl | H | H | C(=O)OH | 331 | 4.43 | |
| 64 | B7a | ethyl | Cl | Cl | H | H | C(=O)OCH(CH₃)₂ | 373 | 6.05 | |
| 50 | B2a/B2b | ethyl | Br | Br | H | C(=O)OCH₃ | C(=O)OCH₃ | 492 | 5.36 | |

TABLE 1-continued
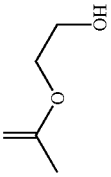
| Co. no. | Ex. no. | $R_1$ | $R_{2a}$ | $R_{2b}$ | $R_{2c}$ | $R_3$ | $R_4$ | [M+]* | retention time (minutes) | other |
|---|---|---|---|---|---|---|---|---|---|---|
| 63 | B7b | ethyl | Cl | Cl | H | H | 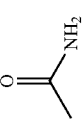 | 375 | 5.17 | |
| 51 | B5a | ethyl | Cl | Cl | H | H | 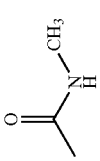 | 330 | 4.86 | |
| 52 | B6 | ethyl | Cl | Cl | H | H | 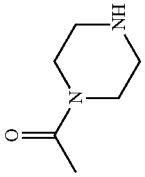 | 344 | 4.99 | |
| 53 | B6 | ethyl | Cl | Cl | H | H | 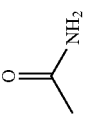 | 399 | 4.61 | |
| 54 | B5a | methyl | Cl | Cl | H |  | H | 315 | 4.65 | |

TABLE 1-continued
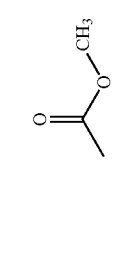
| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 55 | B2a/B2b | methyl | Cl | Cl | H | OC(O)CH₃ | OC(O)CH₃ | 388 | 5.43 | |
| 65 | B7a | ethyl | CF₃ | F | H | OC(O)C(CH₃)₃ | H | | | |
| 56 | B2a/B2b | phenyl | Cl | Cl | H | OC(O)CH₃ | OC(O)CH₃ | 450 | 5.93 | |
| 69 | B15 | n-propyl | Cl | Cl | H | NHC(O)CH₃ | NHC(O)CH₃ | 458 | 5.1 | |
| 57 | B13 | ethyl | Br | Br | H | C(O)NH₂ | C(O)NH₂ | 460 | 5.4 | |

TABLE 1-continued
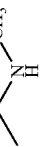
| Co. no. | Ex. no. | R₁ | R₂ₐ | R₂ᵦ | R₂ᵧ | R₃ | R₄ | [M⁺]* | retention time (minutes) | other |
|---|---|---|---|---|---|---|---|---|---|---|
| 70 | B15 | ethyl | Cl | Cl | H | —C≡N | 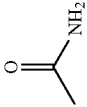 | 368 | 4.26 | |
| 58 | B10/B11 | ethyl | Cl | Cl | H | C(=O)NH₂ | H | 329 | 5.02 | A-isomer; +210.5°[3] |
| 59 | B10/B11 | ethyl | Cl | Cl | H | C(=O)NH₂ | H | 329 | 5.02 | B-isomer; −202.17°[4] |
| 60 | B2a/B2b | n-propyl | Cl | Cl | H | C(=O)OCH₃ | 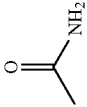 | | | |
| 72 | B1a/B1b |  | Cl | Cl | H | C(=O)OCH₃ | H | 398 | 6.82 | |

TABLE 1-continued
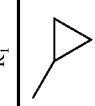
| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 2 | B1a/B1b | cyclopropyl | Cl | Cl | H | -C(=O)-O-CH₃ | H | 356 | 5.99 | |
| 68 | B2d | ethyl | Cl | Cl | H | -C(=O)-O-CH₃ | -C(=O)-OH | | 5.81 | |
| 4 | B2a/B2b | cyclopropyl | Cl | Cl | H | -C(=O)-O-CH₃ | -C(=O)-O-CH₃ | 414 | | |
| 73 | B2a/B2b | cyclohexyl | Cl | Cl | H | -C(=O)-O-CH₃ | -C(=O)-O-CH₃ | 456 | 6.64 | |
| 79 | B18 | ethyl | Cl | Cl | H | -C(=O)-O-CH₃ | H | 345 | 5.94 | S-(-) |
| 13 | B8 | methyl | Cl | Cl | H | -C≡N | -C≡N | | | |

TABLE 1-continued
| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 93 | B1a/B1b | N(CH₃)(CH₂CH₃) | Cl | Cl | H | -C(O)-O-CH₃ | H | 374 | 5.67 | |
| 94 | B1a/B1b | -O-CH₂CH₃ with CH₃ | Cl | Cl | H | -C(O)-O-CH₃ | H | 361 | 5.49 | |
| 95 | B6 | ethyl | Cl | Cl | H | -C(O)-NH-NH₂ | H | 343 (−) | 4.65 | |
| 84 | B23a | ethyl | Cl | Cl | H | -C(O)-O-CH₃ | -C(O)-Cl | | | |
| 96 | B6 | ethyl | Cl | Cl | H | -C(O)-O-CH₃ | -C(O)-NH-N(C(O)CH₃)-NH-C(O)CH₃ | 445 | 4.53 | |

TABLE 1-continued
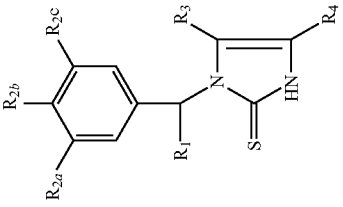
| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 97 | B1a/B1b | ethyl | CH₃ | CH₃ | H | O=C(OCH₃)CH₂- | H | 305 | 5.40 | |
| 98 | B13 | methyl | Cl | Cl | H | O=C(NH₂)CH₂- | O=C(OCH₃)CH₂- | 359 | 3.69 | |
| 92 | B28 | methyl | Cl | Cl | H | O=C(NH₂)CH₂- | O=C(NH₂)CH₂- | 374 | 3.82 | |
| 91 | B28 | methyl | Cl | Cl | H | H | O=C(NH₂)CH₂- | 316 | 4.39 | |
| 90 | B28 | methyl | Cl | Cl | H | O=C(OCH₃)CH₂- | O=C(NH₂)CH₂- | 374 | 4.53 | |
| 99 | B2a/B2d | ethyl | CH₃ | CH₃ | H | O=C(OCH₃)CH₂- | O=C(OCH₃)CH₂- | 363 | 5.28 | |

TABLE 1-continued
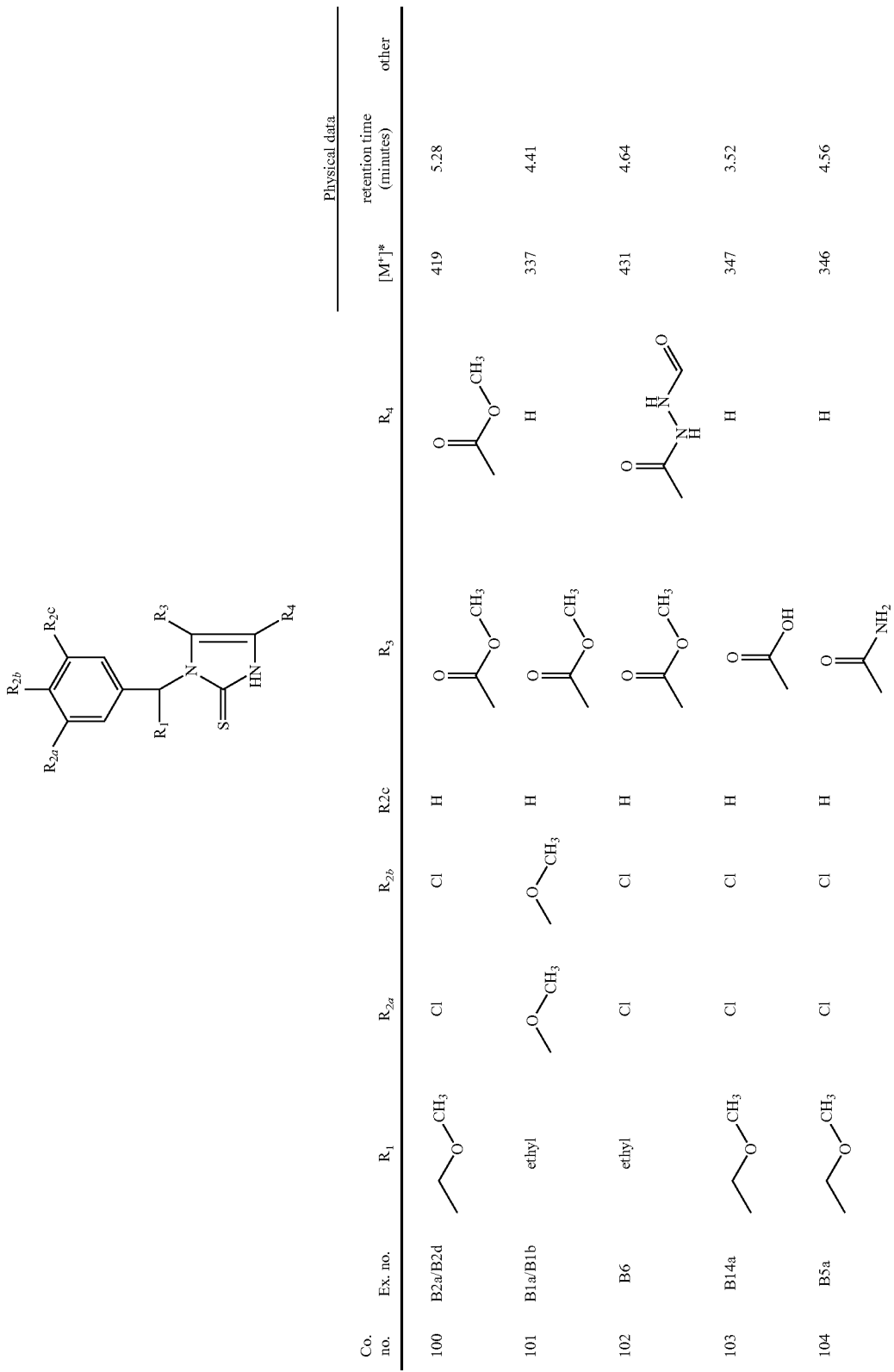
| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 100 | B2a/B2d | −CH₂OCH₃ | Cl | Cl | H | −C(=O)OCH₃ | −C(=O)OCH₃ | 419 | 5.28 | |
| 101 | B1a/B1b | ethyl | −OCH₃ | −OCH₃ | H | −C(=O)OCH₃ | H | 337 | 4.41 | |
| 102 | B6 | ethyl | Cl | Cl | H | −C(=O)OCH₃ | −C(=O)NHNHCHO | 431 | 4.64 | |
| 103 | B14a | −CH₂OCH₃ | Cl | Cl | H | −C(=O)OH | H | 347 | 3.52 | |
| 104 | B5a | −CH₂OCH₃ | Cl | Cl | H | −C(=O)NH₂ | H | 346 | 4.56 | |

TABLE 1-continued
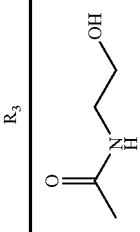
| Co. no. | Ex. no. | R₁ | R₂ₐ | R₂ᵦ | R₂꜀ | R₃ | R₄ | [M⁺]* | retention time (minutes) | other |
|---|---|---|---|---|---|---|---|---|---|---|
| 105 | B6 | ethyl | Cl | Cl | H | 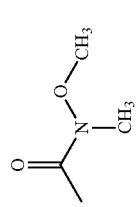 | H | 374 | 4.81 | |
| 106 | B6 | ethyl | Cl | Cl | H | 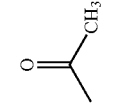 | H | 374 | 5.58 | |
| 81 | B20 | ethyl | Cl | Cl | H | 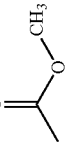 | H | 329 | 5.69 | |
| 85 | B23b | ethyl | Cl | Cl | H |  | OH | 375 | 5.30 | |
| 86 | B24 | ethyl | Cl | Cl | H |  | NH₂ | 386 (−) | 4.96 | |

TABLE 1-continued
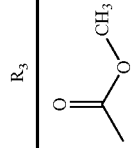
| Co. no. | Ex. no. | $R_1$ | $R_{2a}$ | $R_{2b}$ | $R_{2c}$ | $R_3$ | $R_4$ | [M+]* | retention time (minutes) | other |
|---|---|---|---|---|---|---|---|---|---|---|
| 87 | B25 | ethyl | Cl | Cl | H | 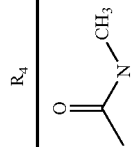 | 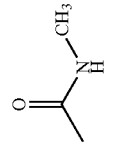 | 402 | 5.09 | |
| 107 | B15 | ethyl | Cl | Cl | H | 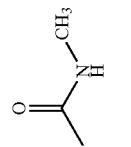 | 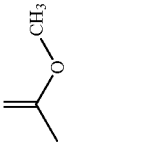 | 401 | 4.60 | |
| 108 | B6 | ethyl | Cl | Cl | H | 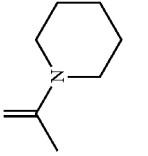 | 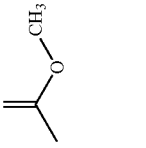 | 456 | 5.51 | |
| 109 | B6 | ethyl | Cl | Cl | H | 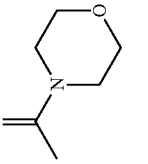 | | 458 | 4.89 | |

TABLE 1-continued

| Co. no. | Ex. no. | $R_1$ | $R_{2a}$ | $R_{2b}$ | $R_{2c}$ | $R_3$ | $R_4$ | [M+]* | retention time (minutes) | other |
|---|---|---|---|---|---|---|---|---|---|---|
| 110 | B6 | ethyl | Cl | Cl | H | —C(=O)—O—CH₃ (methyl ester via CH₂) | —C(=O)—NH—CH₂CH₂—OH | 432 | 4.85 | |
| 89 | B27 | ethyl | Cl | Cl | H | —C(=O)—O—CH₃ | —O—CH₂CH₃ | 389 | 6.06 | |
| 111 | B6 | ethyl | F | F | H | —C(=O)—N(OCH₃)(CH₃) | H | 342 | 4.56 | |
| 112 | B6 | ethyl | F | F | H | —C(=O)—NH—CH₂CH₂—OH | H | 342 | 3.89 | |
| 113 | B6 | ethyl | Cl | Cl | H | —C(=O)—NH₂ | —O—CH₂CH₃ | 374 | 4.80 | |

TABLE 1-continued
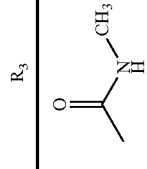
| Co. no. | Ex. no. | $R_1$ | $R_{2a}$ | $R_{2b}$ | $R_{2c}$ | $R_3$ | $R_4$ | Physical data [M+]* | retention time (minutes) | other |
|---|---|---|---|---|---|---|---|---|---|---|
| 114 | B6 | ethyl | Cl | Cl | H |  |  | 388 | 5.12 | |
| 115 | B6 | ethyl | Cl | Cl | H |  | 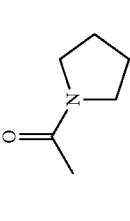 | 418 | 4.74 | |
| 116 | B6 | ethyl | Cl | Cl | H |  | 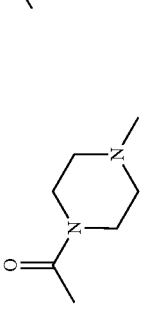 | 428 | 5.55 | |
| 117 | B6 | ethyl | Cl | Cl | H |  | | 457 | 5.33 | |

TABLE 1-continued
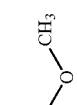
| Co. no. | Ex. no. | $R_1$ | $R_{2a}$ | $R_{2b}$ | $R_{2c}$ | $R_3$ | $R_4$ | Physical data [M+]* | retention time (minutes) | other |
|---|---|---|---|---|---|---|---|---|---|---|
| 118 | B1a/B1b | ethyl | F | H | F | ![](methyl ester) | H | | | mp. 187-189° C. |
| 119 | B6 | ethyl | Cl | Cl | H | acetylhydrazide with N-acetyl | H | 387 | 4.74 | |
| 120 | B6 | ethyl | Cl | Cl | H | acetylhydrazide with N-formyl | H | 373 | 4.69 | |
| 121 | A5 | ethyl | Cl | Cl | H | acetyl chloride | H | | | |
| 122 | B2d | ethyl | Cl | Cl | H | methyl ester | tert-butyl ester | 445 | 6.44 | |

TABLE 1-continued

| Co. no. | Ex. no. | R₁ | R₂ₐ | R₂ᵦ | R₂ᵧ | R₃ | R₄ | [M⁺]* | retention time (minutes) | other |
|---|---|---|---|---|---|---|---|---|---|---|
| 123 | B1a/B1b | ethyl | H | Cl | H | methyl acetate (—O—C(=O)—CH₃) | H | 311 | 5.31 | |
| 124 | B2a | ethyl | F | H | F | methyl acetate (—O—C(=O)—CH₃) | methyl acetate (—O—C(=O)—CH₃) | 371 | 5.37 | |
| 125 | B20 | ethyl | F | F | H | —C(=O)—CH₃ | H | 295*** | 5.08 | |
| 126 | B6 | ethyl | F | H | F | —C(=O)—NH₂ | H | 298 | 4.22 | |
| 127 | B6 | ethyl | F | H | F | —C(=O)—NH—CH₂CH₂OH | H | 342 | 4.18 | |

TABLE 1-continued
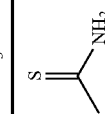
| Co. no. | Ex. no. | $R_1$ | $R_{2a}$ | $R_{2b}$ | $R_{2c}$ | $R_3$ | $R_4$ | [M+]* | retention time (minutes) | other |
|---|---|---|---|---|---|---|---|---|---|---|
| 82 | B21 | ethyl | Cl | Cl | H | -nh2) | H | 346 | 5.45 | |
| 128 | B1a/B1b | ethyl | Cl | H | Cl | OCH3) | H | | | mp. 159-163° C. |
| 129 | B1a/B1b | ethyl | CF3 | H | CF3 | OCH3) | H | | | mp. 151-155° C. |
| 130 | B2a | ethyl | Cl | H | Cl | OCH3) | OCH3) | | | mp. 160-165° C. |
| 131 | B6 | ethyl | CF3 | H | CF3 | NH2) | H | 396*** | 4.65 | |
| 132 | B2a | ethyl | CF3 | H | CF3 | OCH3) | OCH3) | | | mp. 107-109° C. |

TABLE 1-continued
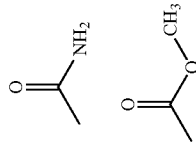
| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 133 | B6 | ethyl | Cl | H | Cl |  | H | 328*** | 4.25 | |
| 134 | B1a/B1b | ethyl |  (OMe-phenyl) | H | H | 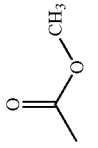 | H | 369 | 5.06 | |
| 135 | B1a/B1b | ethyl | F | F | F | 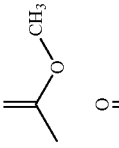 | H | 329*** | 4.68 | |
| 136 | B2a/B2b | ethyl |  (OMe-phenyl) | H | H | 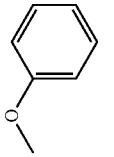 | 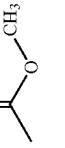 | 427 | 5.58 | |
| 137 | B2d | ethyl | F | F | H | 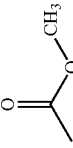 |  | 413 | 5.61 | |

TABLE 1-continued
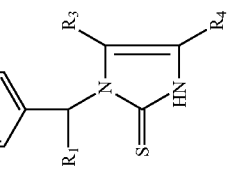
| Co. no. | Ex. no. | R₁ | R₂ₐ | R₂ᵦ | R₂c | R₃ | R₄ | Physical data [M⁺]* | retention time (minutes) | other |
|---|---|---|---|---|---|---|---|---|---|---|
| 138 | B6 | ethyl | Br | Br | H | | H | | | mp. 128° C. |
| 139 | B6 | ethyl | (3-methoxyphenyl) | H | H | | H | 325 | 5.28 | |
| 140 | B1a/B1b | (3,4-dichlorophenyl) | Cl | Cl | H | ![](methyl ester) | H | | | mp. 222-226° C. |
| 141 | B14a | (3,4-dichlorophenyl) | Cl | Cl | H | ![](carboxylic acid) | H | | | mp. 236-242° C. |
| 142 | B6 | ethyl | F | F | H | ![](methyl ester) | | 356 | 4.23 | |

TABLE 1-continued

| Co. no. | Ex. no. | R₁ | R₂ₐ | R₂ᵦ | R₂ᵧ | R₃ | R₄ | [M⁺]* | retention time (minutes) | other |
|---|---|---|---|---|---|---|---|---|---|---|
| 143 | B6 | ethyl | F | F | F | C(=O)NH₂ | H | 316 | 4.26 | |
| 144 | B2d | propyl | Cl | Cl | H | C(=O)OC(CH₃)₃ | C(=O)OC(CH₃)₃ | | | |
| 145 | B2d | propyl | Cl | Cl | H | C(=O)OC(CH₃)₃ | C(=O)OH | | | |
| 146 | B2d | propyl | Cl | Cl | H | C(=O)OCH₃ | C(=O)OC(CH₃)₃ | 459 | 7.01 | |
| 147 | B1a/B1b | 2-thienyl | Cl | Cl | H | C(=O)OCH₃ | H | 399 | 6.12 | |
| 148 | B2d | ethyl | F | F | F | C(=O)OCH₃ | C(=O)OCH₃ | 389 | 5.14 | |

TABLE 1-continued
| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 149 | B6 | propyl | Cl | Cl | H |  |  | 402 | 5.39 | |
| 83 | B22 | ethyl | Cl | Cl | H |  | H | 331 | 5.01 | |
| 150 | B2a | 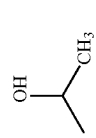 | Cl | Cl | H | 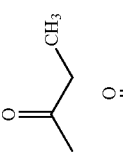 |  | 521 | 5.96 | |
| 151 | B20 | ethyl | Cl | Cl | H |  | H | 343 | 5.96 | |
| 152 | B14a | ethyl | Cl | Cl | H |  |  | 376 | 3.65 | |

TABLE 1-continued
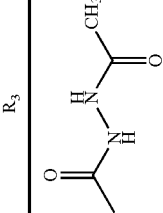
| Co. no. | Ex. no. | R₁ | R₂ₐ | R₂ᵦ | R₂c | R₃ | R₄ | [M⁺]* | retention time (minutes) | other |
|---|---|---|---|---|---|---|---|---|---|---|
| 153 | B6 | ethyl | F | H | F | 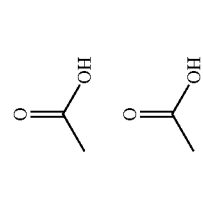 | H | | | |
| 154 | B14a | ethyl | F | H | F | 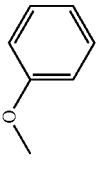 | H | | | |
| 155 | B14a | ethyl |  | H | H | 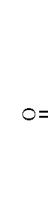 | H | 355 | 3.89 | |
| 156 | B6 | ethyl | F | H | F | 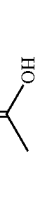 | H | | | |
| 157 | B14a | ethyl | F | F | F | | H | 315*** | 2.87 | |

TABLE 1-continued

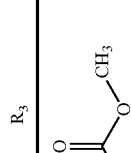

| Co. no. | Ex. no. | $R_1$ | $R_{2a}$ | $R_{2b}$ | $R_{2c}$ | $R_3$ | $R_4$ | Physical data [M+]* | retention time (minutes) | other |
|---|---|---|---|---|---|---|---|---|---|---|
| 158 | B2d | ethyl | F | F | H | ![](methyl acetate) | ![](acetic acid) | 355*** | 4.31 | |
| 159 | B6 | ethyl | Cl | Cl | H | ![](diacetyl hydrazide) | H | 388 | 3.69 | |
| 88 | B26 | ethyl | Cl | Cl | H | —C≡N | ![](acetic acid) | 354*** | 5.22 | |
| 78 | B17 | ethyl | Cl | Cl | H | —C≡N | ![](tert-butyl acetate) | 412 | 4.70 | |

*[M+] defines the mass of the compound
**retention time obtained on a 18 minutes column.
***Mass −1, only response in negative mode.
[1] $[\alpha]_{20}^D$ at concentration of 2.40 g/100 ml in $CHCl_3$;
[2] $[\alpha]_{20}^D$ at concentration of 3.42 g/100 ml in $CHCl_3$;
[3] $[\alpha]_{20}^D$ at concentration of 0.2152 g/100 ml in $CH_3OH$;
[4] $[\alpha]_{20}^D$ at concentration of 0.2216 g/100 ml in $CHCl_3$ TABLE 2
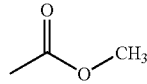
| Co. no. | Ex. no. | $R_1$ | $R_{2a}$ | $R_{2b}$ | $R_3$ | $R_4$ | $R_5$ | [M+]* | retention time (minutes) | other |
|---|---|---|---|---|---|---|---|---|---|---|
| 80 | B19 | $CH_3$ | Cl | Cl | (acetate-O-CH3 group) | H | $CH_3$ | 343*** | 4.81 | |
*[M+] defines the mass of the compound
TABLE 3
| Co. no. | Ex. no. | $R_1$ | $R_{2a}$ | $R_{2b}$ | $R_{2c}$ | [M+]* | retention time (minutes) | other |
|---|---|---|---|---|---|---|---|---|
| 77 | B16 | cyclopropyl | Cl | Cl | H | 383 | 4.65 | |
| 160 | B16 | $CH_3$ | | Cl | Cl | H | 383 | 3.84 |
| 161 | B16 | phenyl | Cl | Cl | H | 417 | 4.68 | |
| 162 | B16 | cyclohexyl | Cl | Cl | H | 423 | 5.34 | |
| 163 | B16 | ethyl | Cl | H | Cl | 373 | 4.24 | |
| 164 | B16 | ethyl | Cl | Cl | H | 371 | 4.38 | |
| 165 | B16 | ethyl | F | F | H | 339 | 3.69 | |
*[M+] defines the mass of the compound C. Pharmacological Example Inhibition of MCP-1 Induced Ca-flux in Human THP-1 Cells MCP-1 binding to the CCR2 receptor induces a rapid and transient intracellular release of $Ca^{2+}$ (secondary messenger) in several cell lines (Charo et al, PNAS 1994). Free $Ca^{2+}$ levels can be measured using a $Ca^{2+}$ sensitive dye. When the CCR2 receptor is blocked with a CCR2 receptor antagonist, the MCP-1 induced release of $Ca^{2+}$ is inhibited.

Human THP-1 cells (monocytic cell line, ATCC TIB-202) were cultured in RPMI 1640 medium supplemented with 10% fetal calf serum (FCS), 1% L-Glutamine, penicillin (50 U/ml) and streptomycin (50 µg/ml) (all GIBCO BRL, Gent). After centrifugation, cells were loaded for 30 minutes with the $Ca^{2+}$ sensitive fluorescent dye Fluo-3 AM (Molecular Probes, Leiden, Netherlands) (2 million cells/ml in RPMI medium containing 4 µM Fluo-3 AM, 20 mM HEPES, 0.1% Bovine Serum Albumin (BSA) and 5 mM probenecid). Excess dye was removed by 3-fold washing with buffer (5 mM HEPES, 140 mM NaCl, 1 mM $MgCl_2$, 5 mM KCl, 10 mM glucose, 2.5 mM probenecid, 1.25 mM $CaCl_2$, 0.1% BSA; all further incubations were done in this buffer). Cells were plated at a density of 150 000 cells/well in dark-wall 96-well plates (Costar, Cambridge, Mass.) and sedimented by centrifugation (1 minute). The cells were pre-incubated for 20 minutes with test compound. Then, $10^{-7}$ M hMCP-1 (Bachem, Bubendorf, Switserland) was added. Changes in intracellular free $Ca^{2+}$ concentration were measured using the Fluorescent Imaging Plate Reader (FLIPR, Molecular Devices, Munchen, Germany). Fluorescence was recorded every second from 10 seconds before the addition of the MCP-1 till 2 minutes after the addition (first minute: 60 records with 1 second intervals, second minute 20 records with 3 second intervals).

The maximal fluorescence obtained during this time frame was used for further calculations.

Table 4 reports $pIC_{50}$ values obtained in the above-described test for compounds of formula (I). $pIC_{50}$ defines $-\log IC_{50}$ wherein $IC_{50}$ is the molar concentration of the test compound which inhibits 50% of specific MCP-1 induced $Ca^{2+}$ flux.

TABLE 4

| CoNo | pIC50 |
| --- | --- |
| 24 | 6.05 |
| 25 | 5.45 |
| 31 | 5.43 |
| 32 | 6.59 |
| 33 | 6.58 |
| 34 | 6.66 |
| 23 | 5.48 |
| 35 | 6.86 |
| 21 | 5.99 |
| 16 | 5.99 |
| 17 | 7.06 |
| 15 | 6.72 |
| 76 | 6.59 |
| 36 | 5.65 |
| 6 | 6.58 |
| 37 | 8.014 |
| 74 | 5.47 |
| 7 | 6.155 |
| 75 | 6.58 |
| 8 | 7.456 |
| 39 | 8.14 |
| 40 | 5.86 |
| 1 | 6.03 |
| 3 | 7.76 |
| 9 | 6.333 |
| 66 | 6.125 |
| 43 | 5.7 |
| 44 | 5.505 |
| 45 | 5.605 |
| 46 | 8.005 |
| 47 | 7.45 |
| 67 | 5.63 |
| 14 | 6.45 |
| 5 | 7.4 |
| 48 | 7.05 |
| 12 | 6.46 |
| 61 | 6.64 |
| 49 | 5.64 |
| 10 | 6.69 |
| 62 | 5.99 |
| 19 | 6.92 |
| 20 | 7.245 |
| 50 | 7.53 |
| 63 | 5.99 |
| 51 | 5.75 |
| 52 | 5.09 |
| 54 | 5.96 |
| 55 | 7.9 |
| 56 | 6.693 |
| 69 | 6.405 |
| 57 | 6.775 |
| 70 | 6.59 |
| 59 | 7.363 |
| 60 | 5.61 |
| 2 | 5.67 |
| 68 | 6.075 |
| 73 | 6.357 |
| 4 | 7.555 |
| 94 | 6.515 |
| 77 | 6.48 |
| 160 | 6.16 |
| 161 | 5.19 |
| 162 | 5.55 |
| 95 | 6.61 |
| 96 | 6.73 |
| 98 | 5.69 |
| 91 | 5.09 |
| 90 | 6.877 |
| 99 | 6.465 |
| 100 | 7.49 |
| 104 | 7.067 |
| 105 | 6.887 |
| 106 | 5.75 |
| 81 | 6.88 |
| 85 | 6.815 |
| 86 | 7.302 |
| 87 | 7.48 |
| 107 | 6.45 |
| 108 | 6.95 |
| 109 | 5.94 |
| 110 | 6.95 |
| 89 | 6.97 |
| 113 | 6.62 |
| 114 | 5.75 |
| 115 | 5.92 |
| 118 | 5.08 |
| 119 | 6.06 |
| 120 | 5.98 |
| 123 | 5.33 |
| 124 | 7.19 |
| 80 | 5.32 |
| 130 | 5.78 |
| 135 | 5.37 |
| 137 | 5.6 |
| 138 | 6.755 |
| 142 | 7.23 |
| 143 | 6.78 |
| 148 | 7.475 |
| 164 | 6.28 |
| 165 | 6.145 |
| 149 | 7.49 |
| 150 | 6.33 |
| 151 | 6.525 |

TABLE 4-continued

| CoNo | pIC50 |
|---|---|
| 159 | 5.78 |
| 88 | 6.76 |
| 78 | 6.09 |

The invention claimed is:

1. A compound of formula (I)

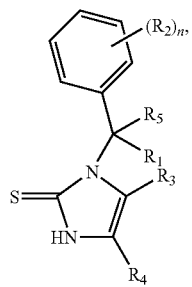

a N—oxide, a pharmaceutically acceptable addition salt, a quaternary amine and a stereochemically isomeric form thereof, wherein $R_1$ represents hydrogen, $C_{1-6}$alkyl, $C_{3-7}$cycloalkyl, $C_{1-6}$alkyloxy$C_{1-6}$alkyl, di($C_{1-6}$alkyl)amino$C_{1-6}$alkyl, aryl or heteroaryl;

each $R_2$ independently represents halo, $C_{1-6}$alkyl, $C_{1-6}$alkyloxy, $C_{1-6}$alkylthio, polyhalo$C_{1-6}$alkyl, polyhalo$C_{1-6}$alkyloxy, cyano, aminocarbonyl, amino, mono- or di($C_{1-4}$alkyl)amino, aryl or aryloxy;

$R_3$ represents hydrogen, cyano, $C_{1-6}$alkyl optionally substituted with hydroxy or $C_{1-6}$alkyloxy, C(=O)—O—$R_6$, C(=O)—$NR_{7a}R_{7b}$, C(=S)$NR_{7a}R_{7b}$, S(=O)$_2$—$NR_{7a}R_{7b}$ or C(=O)—$R_8$;

$R_4$ represents hydrogen, cyano, $C_{1-6}$alkyl optionally substituted with hydroxy or $C_{1-6}$alkyloxy, C(=O)—O—$R_6$, C(=O)—$NR_{7a}R_{7b}$, C(=S)—$NR_{7a}R_{7b}$, S(=O)$_2$—$NR_{7a}R_{7b}$ or C(=O)—$R_8$;

or $R_3$ and $R_4$ taken together may form a bivalent radical of formula —C(=O)—NH—NH—C(=O)—;

$R_6$ represents hydrogen, $C_{1-6}$alkyl, hydroxy$C_{1-6}$alkyl, $C_{2-6}$alkenyl, $C_{2-6}$alkynyl, polyhalo$C_{1-6}$alkyl, $C_{1-6}$alkyloxy$C_{1-6}$alkyl, amino$C_{1-6}$alkyl, mono- or di($C_{1-4}$alkyl)amino$C_{1-6}$alkyl, aminocarbonyl$C_{1-6}$alkyl, mono- or di($C_{1-4}$alkyl)aminocarbonyl$C_{1-6}$alkyl, aryl, pyrrolidinyl, imidazolidinyl, pyrazolidinyl, piperidinyl, piperazinyl, morpholinyl or thiomorpholinyl; wherein pyrrolidinyl, imidazolidinyl, pyrazolidinyl, piperidinyl, piperazinyl, morpholinyl or thiomorpholinyl may optionally be substituted with $C_{1-4}$alkyl;

$R_{7a}$ and $R_{7b}$ each independently represent hydrogen, $C_{1-6}$alkyl, amino, mono- or di($C_{1-4}$alkyl)amino, arylNH—, amino$C_{1-6}$alkyl, mono- or di($C_{1-4}$alkyl)amino $C_{1-6}$alkyl, $C_{1-6}$alkylcarbonylamino, aminocarbonylamino, $C_{1-6}$alkyloxy, —NH—C(O)—H or hydroxy$C_{1-6}$alkyl; or $R_{7a}$ and $R_{7b}$ taken together with the nitrogen to which they are attached form pyrrolidinyl, imidazolidinyl, pyrazolidinyl, piperidinyl, piperazinyl, morpholinyl or thiomorpholinyl;

$R_8$ represents hydrogen, $C_{1-6}$alkyl, hydroxy$C_{1-6}$alkyl, $C_{2-6}$alkenyl, $C_{2-6}$alkynyl, polyhalo$C_{1-6}$alkyl, $C_{1-6}$alkyloxy$C_{1-6}$alkyl, amino$C_{1-6}$alkyl, mono- or di($C_{1-4}$alkyl)amino$C_{1-6}$alkyl, aminocarbonyl$C_{1-6}$alkyl, mono- or di($C_{1-4}$alkyl)aminocarbonyl$C_{1-6}$alkyl or aryl;

$R_5$ represents hydrogen or $C_{1-6}$alkyl; n is 1, 2, 3, 4 or 5;

aryl represents phenyl or phenyl substituted with one, two, three, four or five substituents each independently selected from halo, $C_{1-6}$alkyl, $C_{1-6}$alkyloxy, polyhalo$C_{1-6}$alkyl, polyhalo$C_{1-6}$alkyloxy, cyano, aminocarbonyl, mono- or di($C_{1-4}$alkyl)aminocarbonyl, amino, mono -or di($C_{1-4}$alkyl)amino, phenyloxy or nitro;

heteroaryl represents furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, each of said heterocycles optionally being substituted with one or two substituents each independently selected from halo, $C_{1-6}$alkyl, $C_{1-6}$alkyloxy, polyhalo$C_{1-6}$alkyl, polyhalo$C_{1-6}$alkyloxy, cyano, aminocarbonyl, mono- or di($C_{1-4}$ alkyl)aminocarbonyl, amino, mono- or di($C_{1-4}$ alkyl)amino or nitro;

provided that at least one of $R_3$ or $R_4$ is other than hydrogen; and that if $R_3$ represents C(=O)—OH, C(=O)—O—$C_{1-6}$ alkyl or C(=O)—O—$C_{2-6}$alkenyl, then $R_4$ is other than hydrogen; and that if $R_3$ represents $CH_2OH$ and $R_1$ and $R_5$ represents hydrogen, then $R_4$ is other than hydrogen; and that if $R_3$ represents C(=O)—NH—$C_{1-4}$alkyl—$NH_2$ and $R_1$ and $R_5$ represent hydrogen, then $R_4$ is other than hydrogen; that if $R_3$ represents

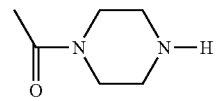

and $R_1$ and $R_5$ represent hydrogen, then $R_4$ is other than hydrogen.

2. A compound according to claim 1 wherein $R_1$ represents hydrogen, $C_{1-6}$alkyl, $C_{3-7}$cycloalkyl, aryl or heteroaryl; $R_3$ represents hydrogen, cyano, $C_{1-6}$alkyl optionally substituted with hydroxy, C(=O)—O—$R_6$, C(=O)—$NR_{7a}R_{7b}$, S(=O)$_2$—$NR_{7a}R_{7b}$, C(=O)—$R_8$; $R_4$ represents hydrogen, cyano, $C_{1-6}$alkyl optionally substituted with hydroxy, C(=O)—O—$R_6$, C(=O)—$NR_{7a}R_{7b}$, S(=O)$_2$—$NR_{7a}R_{7b}$, C(=O)—$R_8$; $R_{7a}$ and $R_{7b}$ each independently represent hydrogen, $C_{1-6}$alkyl, amino, mono- or di($C_{1-4}$alkyl)amino, arylNH—, amino$C_{1-6}$alkyl or mono- or di($C_{1-4}$alkyl)amino$C_{1-6}$alkyl; or $R_{7a}$ and $R_{7b}$ taken together with the nitrogen to which they are attached form pyrrolidinyl, imidazolidinyl, pyrazolidinyl, piperidinyl, piperazinyl, morpholinyl or thiomorpholinyl; and $R_5$ represents hydrogen.

3. A compound according to claim 1 wherein each $R_2$ independently represents halo, $C_{1-6}$alkyl, $C_{1-6}$alkyloxy or polyhalo$C_{1-6}$alkyl; $R_3$ represents hydrogen, cyano, $C_{1-6}$alkyl substituted with hydroxy, C(=O)—O—$R_6$, C(=O)—$NR_{7a}R_{7b}$, C(=S)—$NR_{7a}R_{7b}$ or C(=O)—$R_8$; $R_4$ represents hydrogen, cyano, $C_{1-6}$alkyl optionally substituted with hydroxy or $C_{1-6}$alkyloxy, C(=O)—O—$R_6$ or C(=O)—$NR_{7a}R_{7b}$; $R_3$ and $R_4$ taken together may form a bivalent radical of formula —C(=O)—NH—NH—C(=O)—; $R_6$ represents hydrogen, $C_{1-6}$alkyl, hydroxy$C_{1-6}$alkyl or mono- or di($C_{1-4}$alkyl)aminocarbonyl$C_{1-6}$alkyl; $R_{7a}$ and $R_{7b}$ each independently represent hydrogen, $C_{1-6}$alkyl, amino, $C_{1-6}$alkylcarbonylamino, aminocarbonylamino, $C_{1-6}$alkyloxy, —NH—C(O)—H or hydroxy$C_{1-6}$alkyl; or $R_{7a}$ and $R_{7b}$ taken together with the nitrogen to which they are attached form pyrrolidinyl, piperidinyl, piperazinyl, morpholinyl or piperazinyl substituted with $C_{1-6}$alkyl; $R_8$ represents $C_{1-6}$alkyl; and n is 1, 2 or 3.

4. A compound according to claim 1 wherein $R_1$ represents hydrogen, $C_{1-6}$alkyl, $C_{3-7}$cycloalkyl, aryl or heteroaryl; each $R_2$ independently represents halo, $C_{1-6}$alkyl, $C_{1-6}$alkyloxy or polyhalo$C_{1-6}$alkyl; $R_3$ represents hydrogen, cyano, $C_{1-6}$alkyl substituted with hydroxy, C(=O)—O—$R_6$, C(=O)—$NR_{7a}R_{7b}$ or C(=O)—$R_8$; $R_4$ represents hydrogen, cyano, $C_{1-6}$alkyl optionally substituted with hydroxy, C(=O)—O—$R_6$ or C(=O)—$NR_{7a}R_{7b}$; $R_6$ represents hydrogen, $C_{1-6}$alkyl, hydroxy$C_{1-6}$alkyl or mono- or di($C_{1-4}$alkyl)aminocarbonyl$C_{1-6}$alkyl; $R_{7a}$ and $R_{7b}$ each independently represent hydrogen, $C_{1-6}$alkyl, amino; or $R_{7a}$ and $R_{7b}$ taken together with the nitrogen to which they are attached form pyrrolidinyl, piperidinyl, piperazinyl or morpholinyl; $R_8$ represents $C_{1-6}$alkyl; n is 1, 2 or 3; and $R_5$ represents hydrogen.

5. A compound according to claim 1 wherein $R_1$ represents hydrogen, $C_{1-6}$alkyl, cyclopropyl, cyclohexyl, $C_{1-6}$alkyloxy$C_{1-6}$alkyl, di($C_{1-6}$alkyl)amino$C_{1-6}$alkyl, phenyl or phenyl substituted with two substituents each independently selected from halo; n is 1, 2 and 3; each $R_2$ independently represents halo or polyhalo$C_{1-6}$alkyl; $R_3$ represents hydrogen, cyano, C(=O)—O—$R_6$, C(=O)—$NR_{7a}R_{7b}$ or C(=O)—$R_8$; $R_4$ represents hydrogen, cyano, $C_{1-6}$alkyl optionally substituted with hydroxy or $C_{1-6}$alkyloxy, C(=O)—O—$R_6$ or C(=O)—$NR_{7a}R_{7b}$; $R_3$ and $R_4$ taken together may form a bivalent radical of formula —C(=O)—NH—NH—C(=O)—; $R_6$ represents hydrogen, $C_{1-6}$alkyl or hydroxy$C_{1-6}$alkyl; $R_{7a}$ represent hydrogen or $C_{1-6}$alkyl; and $R_{7b}$ represents hydrogen, $C_{1-6}$alkyl, amino, $C_{1-6}$alkylcarbonylamino, $C_{1-6}$alkyloxy or hydroxy$C_{1-6}$alkyl; or $R_{7a}$ and $R_{7b}$ taken together with the nitrogen to which they are attached form piperidinyl; $R_8$ represents $C_{1-6}$alkyl; and $R_5$ represents hydrogen.

6. A compound according to claim 1 wherein $R_1$ represents hydrogen, $C_{1-6}$alkyl, cyclopropyl, cyclohexyl, phenyl or phenyl substituted with two substituents each independently selected from halo; n is 1, 2 and 3; $R_3$ represents hydrogen, cyano, C(=O)—O—$R_6$, C(=O)—$NR_{7a}R_{7b}$ or C(=O)—$R_8$; $R_4$ represents hydrogen, cyano, $C_{1-6}$alkyl optionally substituted with hydroxy, C(=O)—O—$R_6$ or C(=O)—$NR_{7a}R_{7b}$; $R_6$ represents hydrogen, $C_{1-6}$alkyl or hydroxy$C_{1-6}$alkyl; $R_{7a}$ represent hydrogen or $C_{1-6}$alkyl; and $R_{7b}$ represents hydrogen, $C_{1-6}$alkyl or amino; or $R_{7a}$ and $R_{7b}$ taken together with the nitrogen to which they are attached form piperidinyl; $R_8$ represents $C_{1-6}$alkyl and $R_5$ represents hydrogen.

7. A compound according to claim 1 wherein $R_1$ represents $C_{1-6}$alkyl; n is 2; each $R_2$ independently represents halo; $R_3$ represents C(=O)—O—$R_6$; $R_6$ represents $C_{1-6}$alkyl; and $R_5$ represents hydrogen.

8. A pharmaceutical composition comprising a pharmaceutically acceptable carrier, and as active ingredient a therapeutically effective amount of a compound as claimed in claim 1.

9. A process of preparing a compound as defined in claim 1 characterized by a) reacting an intermediate of formula (II) with HC(=O)—O—$CH_3$ in the presence of a suitable base, followed by treatment with a suitable acid and KSCN and a suitable solvent

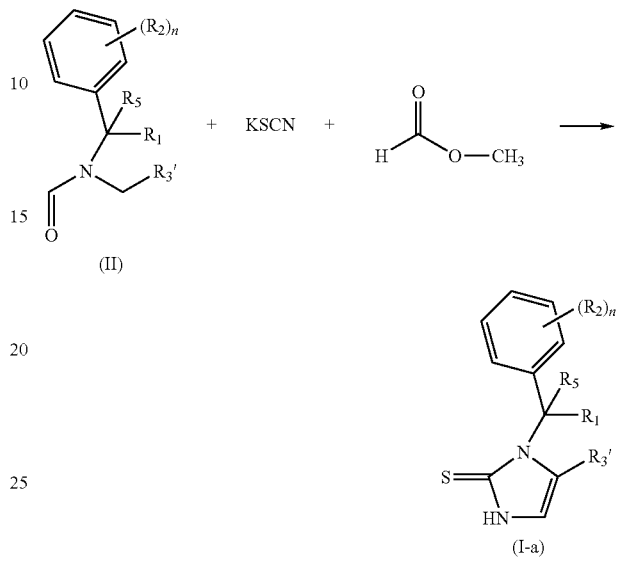

wherein $R_1$, $R_2$, $R_5$ and n are defined as in claim 1 and wherein $R_{3'}$ represents $R_3$ as defined in claim 1 but other than hydrogen;

b) reacting an intermediate of formula (II-a) with HC(=O)—O—$CH_3$ in the presence of a suitable base, followed by treatment with a suitable acid and KSCN in the presence of a suitable solvent

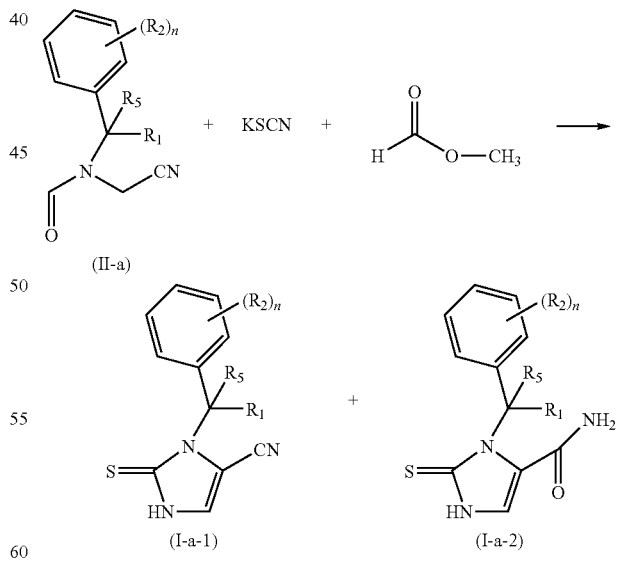

wherein $R_1$, $R_2$, $R_5$ and n are defined as in claim 1;

c) reacting an intermediate of formula (II) with an intermediate of formula (III) in the presence of a suitable base, followed by treatment with a suitable acid and KSCN in the presence of a suitable solvent

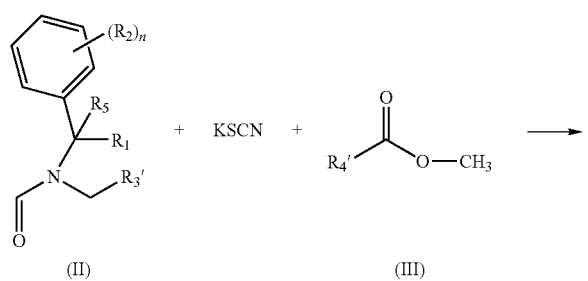

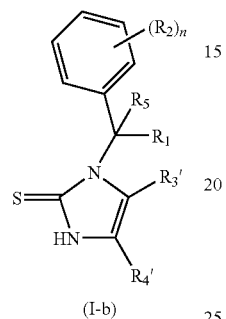

wherein $R_1$, $R_2$, $R_5$ and n are defined as in claim 1 and wherein $R_{3'}$ and $R_{4'}$ represent $R_3$ respectively $R_4$ as defined in claim 1 but other than hydrogen;

d) reacting an intermediate of formula (II-b) with an intermediate of formula (III-b) in the presence of a suitable base, followed by treatment with a suitable acid and KSCN in the presence of a suitable solvent

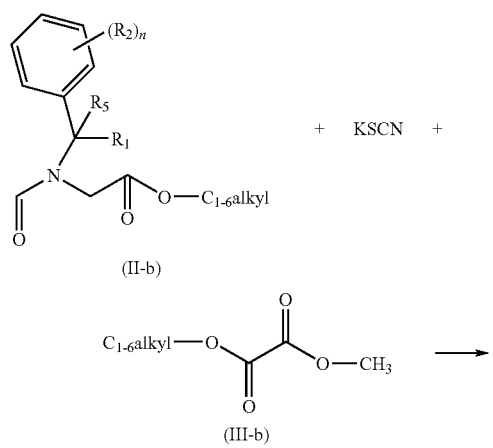

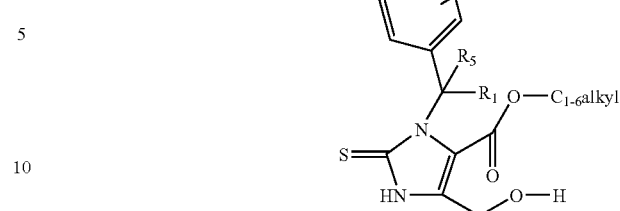

wherein $R_1$, $R_2$, $R_5$ and n are defined as in claim 1;

e) reacting an intermediate of formula (IV) with KSCN in the presence of a suitable acid and a suitable solvent

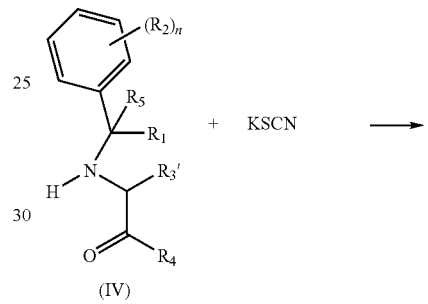

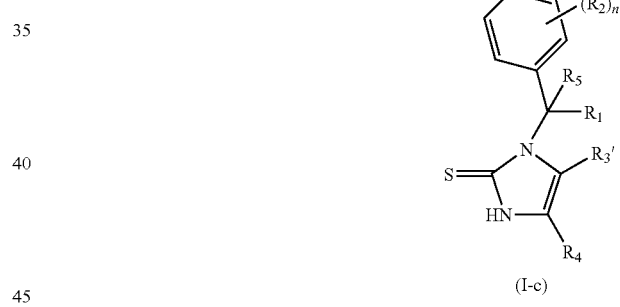

wherein $R_1$, $R_2$, $R_4$, $R_5$ and n are defined as in claim 1 and wherein $R_{3'}$ represents $R_3$ as defined in claim 1 but other than hydrogen;

f) reacting an intermediate of formula (V) with Cl—C(=S)—Cl in the presence of a suitable base and a suitable solvent

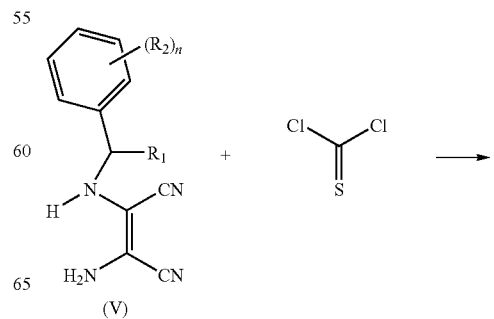

-continued

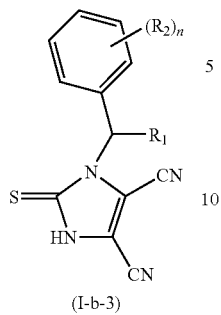

(I-b-3)

wherein R₁, R₂ and n are defined as in claim 1;

g) reacting an intermediate of formula (VI) wherein W₁ represents a suitable leaving group, with an intermediate of formula (VII) in the presence of a suitable solvent

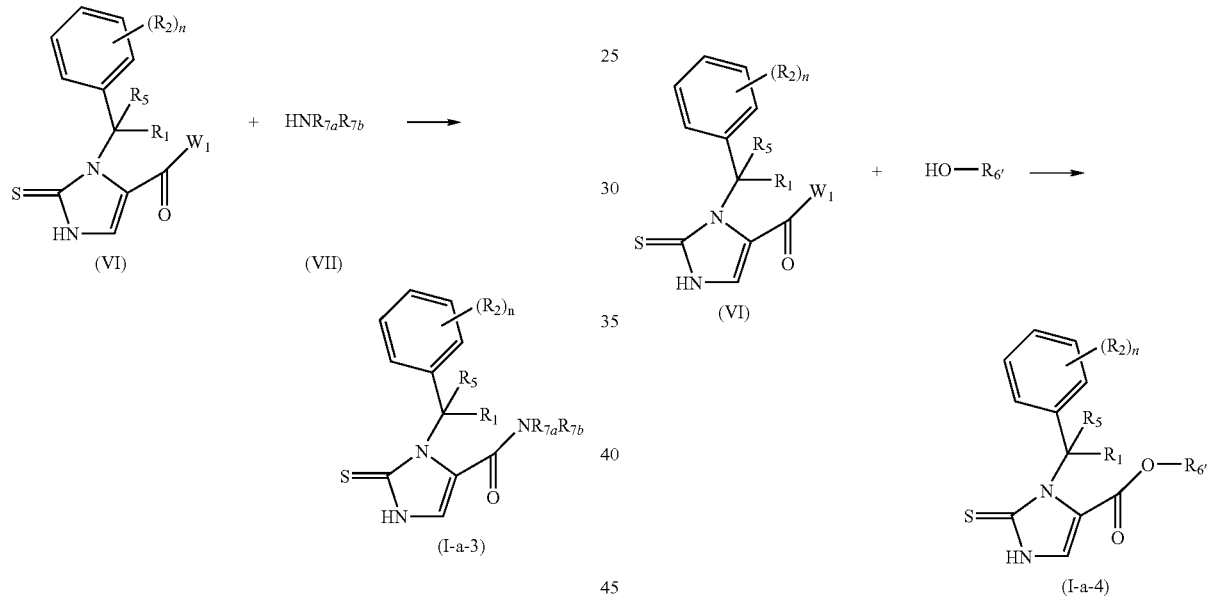

wherein R₁, R₂, R₅, C(=O)—NR₇ₐR₇ᵦ and n are defined as in claim 1;

h) reacting an intermediate of formula (XX) with an intermediate of formula (VII), in the presence of a suitable solvent

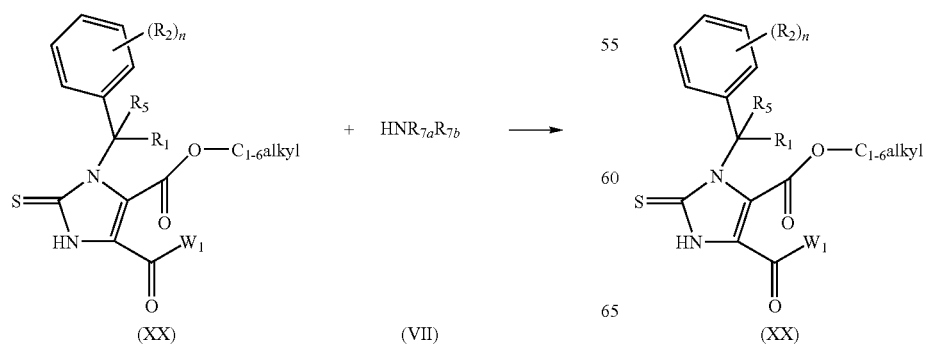

-continued (I-b-4)

wherein R₁, R₂, R₅, C(=O)—NR₇ₐR₇ᵦ and n are defined as in claim 1;

i) reacting an intermediate of formula (VI) with an appropriate alcohol of formula HO—R₆′ in the presence of a suitable solvent (I-a-4)

wherein R₁, R₂, R₅ and n are defined as in claim 1 and wherein R₆′ represents C₁₋₆alkyl or hydroxyC₁₋₆alkyl;

j) reacting an intermediate of formula (XX) with a suitable reducing agent in the presence of a suitable solvent -continued

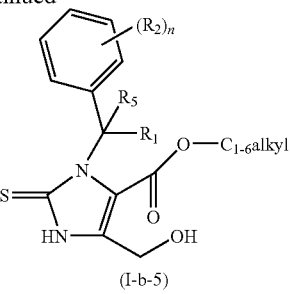

(I-b-5)

wherein $R_1$, $R_2$, $R_5$ and n are defined as in claim 1 k) reacting an intermediate of formula (VIII) wherein $W_2$ represents a suitable leaving group, with an alcoholate base, such as for example $NaOC_{1-6}alkyl$, in the presence of the corresponding alcohol $C_{1-6}alkyl$-OH:

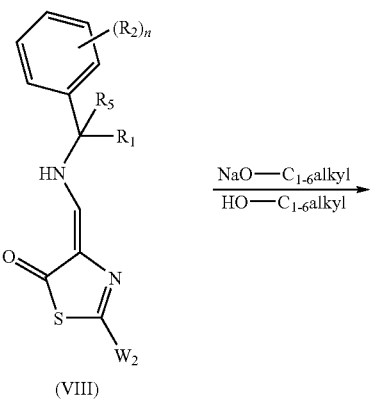 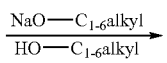

(VIII)

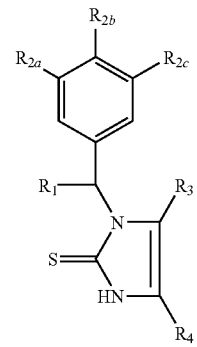

(I-d)

wherein $R_1$, $R_2$, $R_5$ and n are defined as in claim 1;

and, if desired, converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms, quaternary amines or N-oxide forms thereof.

10. A compound according to claim 1 of the formula:

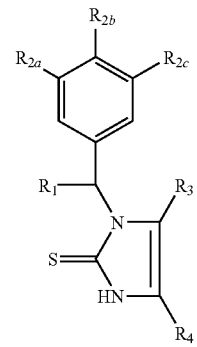

wherein $R_1$ is ethyl, $R_{2a}$ is Cl, $R_{2b}$ is Cl, $R_{2c}$ is H, $R_3$ is —C(O)OCH$_3$ and $R_4$ is —C(O)OCH$_3$.

11. A compound according to claim 1 of the formula:

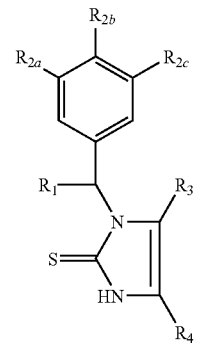

wherein $R_1$ is ethyl, $R_{2a}$ is F, $R_{2b}$ is F, $R_{2c}$ is H, $R_3$ is —C(O)OCH$_3$ and $R_4$ is —C(O)OCH$_3$.

12. A compound according to claim 1 of the formula:

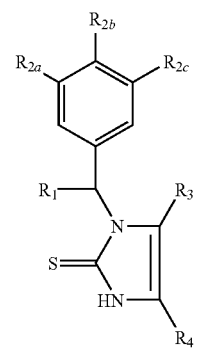

wherein $R_1$ is n-propyl, $R_{2a}$ is Cl, $R_{2b}$ is Cl, $R_{2c}$ is H, $R_3$ is —C(O)OCH$_3$ and $R_4$ is —C(O)OCH$_3$.

* * * * *